US011395831B2

(12) United States Patent
Shah et al.

(10) Patent No.: US 11,395,831 B2
(45) Date of Patent: *Jul. 26, 2022

(54) COMBINATION PRODUCTS OF TOBRAMYCIN COMPOUNDS AND DEXAMETHASONE COMPOUNDS

(71) Applicant: Somerset Therapeutics, LLC, Hollywood, FL (US)

(72) Inventors: Mandar V Shah, Rockaway, NJ (US); Veerappan Subramanian, Warren, NJ (US); Ilango Subramanian, Warren, NJ (US); Ojas Prakashbhai Doshi, Somerville, NJ (US)

(73) Assignee: SOMERSET THERAPEUTICS, LLC., Hollywood, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/327,703

(22) Filed: May 22, 2021

(65) Prior Publication Data

US 2021/0361687 A1    Nov. 25, 2021

Related U.S. Application Data

(60) Provisional application No. 63/029,313, filed on May 22, 2020.

(51) Int. Cl.
| | |
|---|---|
| *A61K 31/7036* | (2006.01) |
| *A61K 9/00* | (2006.01) |
| *A61K 47/18* | (2017.01) |
| *A61K 47/54* | (2017.01) |
| *A61P 27/02* | (2006.01) |
| *A61P 31/04* | (2006.01) |
| *A61K 31/573* | (2006.01) |
| *A61K 47/34* | (2017.01) |
| *A61K 47/60* | (2017.01) |
| *A61K 45/06* | (2006.01) |

(52) U.S. Cl.
CPC ........ *A61K 31/7036* (2013.01); *A61K 9/0048* (2013.01); *A61K 31/573* (2013.01); *A61K 45/06* (2013.01); *A61K 47/183* (2013.01); *A61K 47/34* (2013.01); *A61K 47/545* (2017.08); *A61K 47/60* (2017.08); *A61P 27/02* (2018.01); *A61P 31/04* (2018.01)

(58) Field of Classification Search
None
See application file for complete search history.

(56) References Cited

U.S. PATENT DOCUMENTS 5,149,694 A    9/1992  Cagle et al.
5,811,446 A *  9/1998  Thomas ................. A61K 45/06
                                              514/399

OTHER PUBLICATIONS

Agrahari, et al., "A Comprehensive Insight on Ocular Pharmacokinetics", Drug Deliv Transl Res. Dec. 2016, 6(6):735-754.
Herzog, et al., "Design of Membrane Targeting Tobramycin-based Cationic Amphiphiles with Reduced Hemolytic Activity", MedChemComm, 2013, 4, 120.
Kernt et. al. titled, "A Clinical Comparison of Two Formulations of Tobramycin 0.3% Eyedrops in the Treatment of Acute Bacterial Conjunctivitis.", Eur J Ophthalmol, Sep.-Oct. 2005; 15(5): 541-9—Abstract Only.
Novartis Pharmaceuticals Canada Inc., Product Monograph Inducing Patent Medication Information for Tobradex®, Feb. 12, 2020.
Okada, et al., "Ocular Inflammatory Disease in the New Millennium", Arch Ophthalmol, vol. 118, Jan. 2000.
Souto, et al., "Advanced Formulation Approaches for Ocular Drug Delivery: State-of-the-Art and Recent Patents", Pharmaceutics 2019, 11, 460.
Tejpal, et al., "Microspheres as an Ocular Drug Delivery System—A Review", Journal of Drug Delivery & Therapeutics; 2013, 3(1), 114-123.
Alcon Laboratories, Inc. Tobrex® label, Revised Jun. 2012.
Bauch & Lomb Incorporated, Zylet® label, Jan. 2006.
Tobradex® ST label, Revised Feb. 2009.
Puris et al, "L-type Amino Acid Transporter I as a target for Drug Delivery," 37:88 (17 pages); published online May 6, 2020 (Year 2020).
Notice of Allowance related to U.S. Appl. No. 17/327,701 dated Sep. 22, 2021.
Non-Final Office action related to U.S. Appl. No. 17/327,702 dated Dec. 7, 2021.

* cited by examiner

*Primary Examiner* — Katherine Peebles
(74) *Attorney, Agent, or Firm* — Transformative Legal, LLC; Len S. Smith; Denise M. Brown

(57) ABSTRACT

Disclosed herein are new compositions comprising (1) an antibacterial component comprising (a) a complex comprising (i) an active pharmaceutical ingredient (API) wherein the active pharmaceutical ingredient is tobramycin, a similar compound, or a derivative of either thereof and (ii) a complexing agent, or (b) a derivative of tobramycin or a similar compound comprising one or more conjugates/derivatizing groups, wherein the complexing agent or conjugate(s) cause a detectable increase in API permeation of corneal cells, retention in corneal cells, or both, as compared to the non-complexed or non-derivatized API, and (2) an effective amount of an anti-inflammatory agent, such as dexamethasone or another dexamethasone compound. This disclosure also describes new methods of using such compositions, producing such compositions, and the like.

10 Claims, 11 Drawing Sheets

COMBINATION PRODUCTS OF TOBRAMYCIN COMPOUNDS AND DEXAMETHASONE COMPOUNDS

CROSS REFERENCE TO RELATED APPLICATIONS

This patent application claims priority to U.S. Provisional Patent Application No. 63/029,313 filed May 22, 2020, entitled "Tobramycin Compound Compositions for Ophthalmic Delivery and Associated Methods of Production and Use." This application claims the benefit of priority to, and incorporates by reference the entirety of, this above-referenced priority application.

FIELD OF THE INVENTION

This invention relates to new ophthalmological compositions, processes of preparing such compositions, and new methods of treating conditions of the eye, as well as other additional aspects and features described further herein.

BACKGROUND OF THE INVENTION

A high value is placed on vision and eye health. As such, considerable time and resources are spent on ophthalmic product development. Such products can be divided into two categories by the location within the eye they aim to target: the anterior and posterior segments. The anterior portion comprises about one-third of the eye and consists of anatomy including the conjunctiva, cornea. The posterior portion comprises anatomy all residing behind the lens. Products targeting differing portions of the eye require different considerations, as the challenges presented by the biological environments, barriers, and natural ocular defenses vary between the two.

Common broadly categorized disorders of the anterior portion of the eye include cataracts, infection, and inflammation, inflammation sometimes resulting from infection and other times present independent from infection, resulting from other etiologies such as allergy. Such afflictions, especially infection and inflammation, can vary and can affect humans of all ages (e.g., from infants to the very young and the elderly) as well as other species. The efficacy of topical applications such as those attempting to treat eye conditions such as conjunctivitis (inflammation of the conjunctiva), or other external ocular infections often hinge on their ability to maintain contact with the afflicted eye anatomy or be retained by the eye, e.g., permeate and be held within, the cornea.

Tobramycin is an aminoglycoside that has been used in ophthalmological and other settings as an antibiotic. Several other aminoglycosides are known, and several such antibiotics have been shown to be useful in ophthalmological treatments. However, aminoglycosides can vary significantly in terms of their structure, effectiveness in different settings, and other attributes. Tobramycin, for example, is unique among major aminoglycoside antibiotics in binding the 50 s ribosome in addition to the 30 s ribosome typically only bound by other aminoglycosides.

Not long after the patenting of tobramycin in the mid-1960s and the receipt of approval of tobramycin for medical use in 1974, Novartis, a leading global pharmaceutical company ranked as one of the top five global pharmaceutical innovators, developed the first ophthalmological tobramycin product, TOBREX®, receiving FDA approval for the product in late 1980. The specific approved indication for TOBREX® is the treatment of external infections of the eye and its adnexa by susceptible bacteria. TOBREX® tobramycin ophthalmic solution provides tobramycin in a 0.3% w/v concentration. Due to the many sensitivities of the eye, for example relating to pH and tonicity, concerns related to irritation made delivering higher concentrations of tobramycin challenging and products having higher concentrations of tobramycin have not been approved to date. Due to the limited concentration, as well as tobramycin's low corneal permeability and hence limited ability to be effectively taken up by corneal cells (e.g., before being swept away by natural eye defense mechanisms such as nasolacrimal flushing), frequent, repeated dosing of the product is required. In fact, recommended dosing of TOBREX® in adults and children above the age of one year is the application of one-two drops into the affected eye(s) every four hours (at least six times a day). In severe infections, recommended dosing of TOBREX® in adults and children above the age of one year is the application of two drops into the affected eye(s) hourly.

The introduction of TOBRADEX® by Novartis followed in 1988. TOBRADEX® further incorporates the steroid dexamethasone with tobramycin in an effort to address the inflammation commonly associated with ocular infections and use of products such as TOBREX®. Unfortunately, the introduction of the steroid to the formulation also introduced new concerns, specifically an increased risk of increased intraocular pressure and glaucoma, with associated risk of damage to the optic nerve and defects in visual acuity and fields of vision. Further warnings related to cataract development, delayed post-surgical healing, secondary infection due to suppressed host response, exacerbation of viral infections, development of fungal infection, and use by pregnant and nursing women as they relate to fetal anomalies and mortality are provided on the TOBRADEX® label. At the same time as introducing new safety concerns, the concentration of tobramycin remained the same at 0.3% w/v. As such, the dosing regimen remained essentially unchanged, with administration prescribed as one drop administered every 4-6 hours, optionally the initial 24-48-hour dosing being increased to one drop every 2 hours.

It took nearly another 20 years before another product comprising tobramycin was introduced into the market. Specifically, in 2004, Bausch & Lomb launched a product like TOBRADEX® called Zylet®, a formulation of tobramycin at a concentration of 0.3% and a steroid, in this case the corticosteroid loteprednol etabonate, at a concentration of 0.5%.

Over the course of the following decade and a half, many more attempts were made by formulators to develop tobramycin products and other ophthalmic interventions utilizing a variety of technologies to address the well-known drug availability and/or bioavailability limitations, e.g., drug permeability and retention limitations, and intervention side effect vulnerabilities presented by the eye.

For example, an attempt to develop a twice-a-day tobramycin formulation reportedly used viscosity enhancers, as exemplified in the 2005 European Journal of Ophthalmology paper by Kernt et. al. titled, "A Clinical Comparison of Two Formulations of Tobramycin 0.3% Eyedrops in the Treatment of Acute Bacterial Conjunctivitis." This work reflected results from a large, multi-center clinical trial. However, despite such significant use of resources, this study and other, similar efforts led to no new marketed product. While the fate of such efforts is difficult to ascertain from public records, given the effort and the outcome, such facts suggest that such product candidates may have been associated with an issue or shortcoming in terms of product efficacy, safety, or both.

In 2009, a modified TOBRADEX® formulation, TOBRADEX ST®, was introduced. TOBRADEX ST® comprises tobramycin at the previously marketed concentration of 0.3% w/v (as present in both TOBREX® and TOBRADEX®) and maintains the presence of the steroid dexamethasone (as in TOBRADEX®); however, the formulation is modified such that the concentration of dexamethasone is decreased from 0.1% in TOBRADEX® to 0.05% in TOBRADEX ST®. While reducing the steroid exposure and hence attempting to address the risks associated with such steroid use, the concentration of the antimicrobial tobramycin in the new formulation remained unchanged as compared to earlier products, with dosing remaining at a regimen of 1 drop every 4-6 hours and optionally a drop every 2 hours during the initial 24-48-hour treatment period.

Despite significant investigation in these and a multitude of formulation approaches reported in the art, and the proposed development of tobramycin derivatives with allegedly improved properties reported several times in patent documents and scientific literature, no tobramycin or tobramycin derivative product addressing the limitations associated with on-market tobramycin products, such as dosing and dosage amount, has yet materialized. As a result, earlier developed formulations continue to dominate the market and the most significant recent introductions are primarily targeted at reducing the side effects associated with such formulations. In fact, in the nearly forty years since the approval of TOBREX®, no approved product has adequately addressed the limitations associated with tobramycin products. The disappointing progress of tobramycin product research and development demonstrates that inventiveness is required to make tobramycin products that can effectively address the limitations associated with current on-market products.

Perhaps one factor complicating such research efforts is the numerous options available for seeking to develop improved ophthalmological products. For example, mucoadhesive formulations, ocular/conjunctival inserts, the use of aqueous gels, dendrimers, liposomes, and nanotechnology, among others have been used for developing ophthalmological products. These approaches have been combined with numerous types of formulations including solutions, emulsions, suspensions, ointments, and the like. Means of addressing drug transport via, e.g., solute carriers and ATP-binding cassettes have been introduced; use of prodrugs, iontophoresis, and cyclodextrins have each been subjects of research and development efforts. These and numerous other approaches available to the development of such products are described in, e.g., Souto, in "Advanced Formulation Approaches for Ocular Drug Delivery: State-Of-The-Art and Recent Patents," published in *Pharmaceutics* in 2019 which provides a review of the numerous techniques available for developing ocular formulations. The number of available options, and the complexities of making suitable products for treating conditions of the eye given its sensitive and unique physiological nature, further reflects that an inventive approach is required to develop a tobramycin composition addressing limitations of currently marketed tobramycin ophthalmological products which have reflected the state of the art for four decades.

SUMMARY

Certain aspects of the invention described in this Summary refer to aspects described in other paragraphs, incorporating all of the elements of any such one or more referenced paragraphs. To facilitate such referencing, a paragraph number is provided at the end of each paragraph in this section.

The invention described here provides new pharmaceutical compositions comprising a combination of (a) a compound that is either (i) a complex formed between (A) an active pharmaceutical ingredient that is either tobramycin or a tobramycin-like compound (e.g., an analog, derivative, or alternative form of tobramycin) and (B) an ophthalmologically suitable lipophilic and amphoteric complexing agent, wherein the complexing agent promotes the uptake of the composition by corneal cells, the retention of the complex by corneal cells or both as compared to the free compound, or (ii) a derivative of tobramycin having similar corneal cell uptake properties to such a conjugate, similar corneal cell retention properties to such a conjugate, or both a similar corneal cell uptake and retention properties to such a conjugate and (b) an effective amount of dexamethasone or another dexamethasone compound (e.g., an analog or alternative form of dexamethasone or a derivative of any such analog, alternative form, or dexamethasone) (Summary paragraph 2).

The compositions provided herein address a failure of the current art to provide an effective therapeutic antimicrobial treatment for infections of the eye, wherein the active contained therein is successfully able to permeate the cornea, be retained by the cornea sufficiently to allow for a reduced dosing schedule, or both, and the presence of one or more additional active agents in compositions comprising compounds or complexed compounds described provides further treatment of either the primary indication of the composition, such as microbial infection of the eye or its adnexa, or to related indications such as, for example, inflammation which can accompany such a primary indication. Through the modification of tobramycin (developing derivatives thereof and/or complexing tobramycin or a tobramycin derivative with a complexing agent) and by supplying tobramycin or tobramycin derivative (the primary active) and at least one additional active agent such as dexamethasone or a dexamethasone compound in a composition or formulation having certain properties, a product can be obtained having the ability of tobramycin to be taken up by and delivered across the cornea more rapidly than tobramycin in conventional formulations and/or, further, to facilitate the formation of a depot of the primary active within the cornea for extended release, reduced dosing frequencies and the resulting benefits of the same can be achieved. The invention described herein is presented to address a failure of the current art to provide an effective therapeutic antimicrobial treatment for infections of the eye, wherein the active contained therein is successfully able to permeate the cornea and be retained by the cornea sufficiently to allow for a reduced dosing schedule. In embodiments, the invention described herein in comprising an anti-inflammatory agent such as dexamethasone or a dexamethasone compound is further capable of alleviating one or more additional indications, such as a secondary indication related to a microbial infection, e.g., a detectable or significant reduction of inflammation accompanying an ocular infection (Summary paragraph 3).

The modification of 4,6-disubstituted deoxystreptamine structures, such as in some aspects creating specific derivatives of tobramycin, combining such structures with one or more delivery agents, or both, can result in the ability of the resulting composition to permeate and be retained by the cornea more successfully (rapidly and longer, respectively)

than tobramycin in conventional formulations, such as in TOBREX®, and/or, further, to facilitate the formation of a depot of the active within the cornea. Such physiological differences in the compositions of the invention can, in some aspects, result in different pharmacological conditions of such, such as, e.g., extended release, reduced dosing frequencies, and other benefits described herein (Summary paragraph 4).

According to certain aspects, the invention provides compositions comprising a pharmaceutical composition comprising an antimicrobial active pharmaceutical ingredient comprising an effective amount of a compound having a structure according to the formula

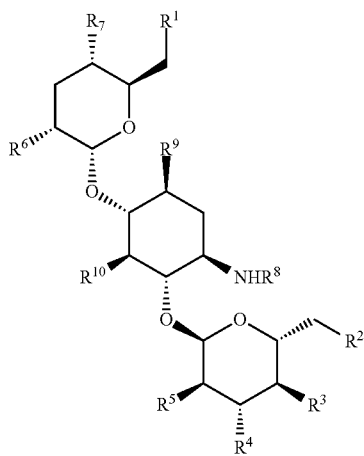

wherein (1) $R^1$ is —CH—$NH_2$ (i.e., methyl-$NH_2$ or Me—$NH_2$) or an optionally substituted alkyl, an optionally substituted aryl, an optionally substituted aralkyl, an optionally substituted cycloalkyl, an optionally substituted cycloalkylalkyl, an optionally substituted heterocyclyl, an optionally substituted heterocyclylalkyl, an optionally substituted heteroaryl, or an optionally substituted heteroarylalkyl; (2) $R^4$, $R^6$, $R^8$, and $R^9$ are —$NH_2$ or an optionally substituted alkyl, an optionally substituted aryl, an optionally substituted aralkyl, an optionally substituted cycloalkyl, an optionally substituted cycloalkylalkyl, an optionally substituted heterocyclyl, an optionally substituted heterocyclylalkyl, an optionally substituted heteroaryl, or an optionally substituted heteroarylalkyl; (3) $R^2$ is —Me—OH or an optionally substituted alkyl, an optionally substituted aryl, an optionally substituted aralkyl, an optionally substituted cycloalkyl, an optionally substituted cycloalkylalkyl, an optionally substituted heterocyclyl, an optionally substituted heterocyclylalkyl, an optionally substituted heteroaryl, or an optionally substituted heteroarylalkyl; and (4) $R^3$, $R^5$, $R^7$ and $R^{10}$ are —OH or an optionally substituted aryl, an optionally substituted aralkyl, an optionally substituted cycloalkyl, an optionally substituted cycloalkylalkyl, an optionally substituted heterocyclyl, an optionally substituted heterocyclylalkyl, an optionally substituted heteroaryl, or an optionally substituted heteroarylalkyl (Formula I), optionally complexed with a lipophilic and amphoteric complexing agent, wherein the composition further comprises one or more additional active agents which target(s) the primary indication or a related indication, and further wherein the composition is ophthalmologically safe and the complexing agent, when present, detectably promotes the uptake of the composition by corneal cells, the retention of the complex by corneal cells, or both, as compared to the free compound. In one aspect, the group of such compounds can include tobramycin. In one aspect, such a group of compounds excludes tobramycin. In one aspect, the one or more additional active agents is an anti-inflammatory agent. In one aspect, the one or more additional active agents is dexamethasone or a dexamethasone compound (Summary paragraph 5).

In aspects, no more than three of $R^1$, $R^2$, $R^3$, $R^4$, $R^5$, $R^6$, $R^7$, $R^8$, $R^9$, and $R^{10}$ of Formula I differ in composition from the corresponding position in tobramycin, such as no more than two or no more than one of $R^1$, $R^2$, $R^3$, $R^4$, $R^5$, $R^6$, $R^7$, $R^8$, $R^9$, and $R^{10}$ differ in composition from the corresponding position in tobramycin (Summary paragraph 6).

In certain aspects, the pharmaceutical composition complexed with the above-described complexing agent more specifically comprises an ophthalmologically suitable antibiotic compound that has a structure according to the formula:

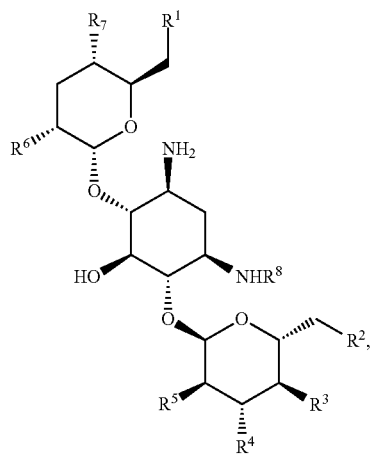

wherein $R^1$-$R^8$ have the characteristics of the following paragraph (Formula II) (Summary paragraph 7).

In certain aspects, the invention provides such a composition wherein no more than three of $R^1$, $R^2$, $R^3$, $R^4$, $R^5$, $R^6$, $R^7$, and $R^8$ differ from the corresponding position in tobramycin, such as no more than two or no more than one of $R^1$, $R^2$, $R^3$, $R^4$, $R^5$, $R^6$, $R^7$, and $R^8$ differ from the corresponding position in tobramycin. In certain further aspects, $R^2$, $R^7$, or both are the same as the corresponding positions in tobramycin. Still further, in some facets $R^2$ is a —Me—Oh and $R^7$ is an —OH (i.e., these positions have the same composition as the corresponding positions in tobramycin) (Summary paragraph 8).

In certain aspects, a compound of Formula II has a structure according to the formula:

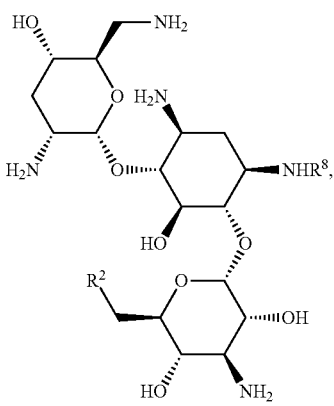

wherein R groups are described in the following paragraph (Formula III). In certain aspects, the compound of Formula III is tobramycin (Summary paragraph 9).

In some facets, the invention provides a pharmaceutical composition described in Summary paragraphs 2-9, wherein any R group that differs from tobramycin includes an optionally derivatized 2-20 atom backbone alkyl or heteroalkyl group (an alkyl group comprising one or more intervening heteroatoms), optionally attached through an ester or amide bond at a position corresponding to an —OH or —NH$_2$ group in tobramycin. In certain facets, the alkyl or heteroalkyl group primarily comprises, generally consists of, or consists of a linear alkyl or heteroalkyl compound (comprising a linear backbone and typically comprising side chains of only 1-4, 1-3, 1-2, or only a single atom/group, e.g., —NH$_2$ or =O). In some aspects, the group is or generally consists of a fatty acid, fatty acid derivative, short fatty acid, or short fatty acid derivative. In certain further aspects, the group is or generally consists of an acetic acid or palmitic acid group (skilled readers will understand that such groups may be modified from their original chemical composition in order to facilitate bonding to the backbone, e.g., through the formation of an amide bond, ester bond, or the like). In certain aspects where the alkyl or heteroalkyl group is a linear alkyl or heteroalkyl compound, the alkyl or heteroalkyl group comprises one or more —C=O or —NH$_2$ groups bound to the backbone. In some facets, the group comprises at least one —C=O group and at least one —NH$_2$ group bound to the backbone. In some alternative aspects where the alkyl or heteroalkyl group is a linear alkyl or heteroalkyl compound, the group comprises no —C=O groups. In certain aspects wherein where the alkyl or heteroalkyl group is a linear alkyl or heteroalkyl compound and the group may or may not comprise at least on —C=O group, the group can comprise at least two —NH$_2$ groups bound to the backbone. As noted, a backbone AOA can comprise such groups or other heteroatom groups as part of the backbone itself (Summary paragraph 10).

In some aspects, the invention provides a composition described in Summary paragraph 10, wherein the backbone of the group is a heteroalkyl structure comprising at least one nitrogen, at least one thiol/sulfur, or both. In certain further aspects, the invention provides any such molecule wherein at least about 90% of the atoms of the backbone are carbons. In further aspects, the backbone comprises or is bound to an optionally derivatized 3-9-membered cycloalkyl or heterocycloalkyl ring. In certain facets, the backbone comprises or is bound to a 3-6 membered ring wherein the ring comprises one or more nitro groups, is bound to one or more nitro groups, or is bound to one or more side chains bound to one or more nitro groups. In some compositions wherein the backbone comprises, or is directly or indirectly bound to, an optionally derivatized 3- to 9-membered cycloalkyl, heterocycloalkyl, aromatic, or heteroaryl/heteroaromatic ring, or a 3-6 membered heterocycloalkyl or heteroaryl wherein the ring comprises one or more nitro groups, is bound to one or more nitro groups, or is bound to one or more side chains bound to one or more nitro groups, wherein the group comprises only one ring (Summary paragraph 11).

In certain aspects, the invention provides a composition described in any of Summary paragraphs 5-11, wherein the compound is a tobramycin derivative. In some facets, the tobramycin derivative itself exhibits detectably faster penetration of corneal cells than tobramycin, exhibits detectably better (increased) uptake or retention in corneal cells than tobramycin, or both. Thus, in such aspects, both the complexing agent when present, and the derivatization of the API with or without a complexing agent, are each contributing to faster corneal cell penetration, increased uptake or retention by corneal cells, or a combination thereof (Summary paragraph 12).

Thus, in some aspects the ophthalmic tobramycin compositions described herein can exhibit an important advantage over conventional formulations and are able to increase the availability of tobramycin, extending contact time of the same with the cornea, increasing the penetration through the complex anatomical structure of the eye, and providing controlled release of active into the eye tissues, thus allowing for a reduction in dosing frequency as will be described below; such compositions further addressing in certain aspects the primary indication (e.g., microbial infection of the eye or its adnexa) or a related indication, such as, e.g., a symptom related to infection such as inflammation by the presence of one or more additional active agents. In aspects, the one or more additional active agents is an anti-inflammatory agent, e.g., a steroid such as dexamethasone or a dexamethasone compound (Summary paragraph 13).

According to some aspects, the invention provides a pharmaceutical composition of any one of (e.g., any one or more of) the preceding paragraphs, wherein a complexing agent is present and the complexing agent is a heterocyclic (e.g., a heteroaromatic) compound comprising at least one three to seven, typically five-to-seven-member nitrogenous ring comprising an attached group comprising a chain/backbone of at least three carbons and at least one carboxylic acid group. In one aspect, the heterocyclic ring comprises at least one nitrogen group in the ring structure. In one aspect, the heterocyclic ring is an imidazole ring. In certain aspects, the complexing agent is an amino acid, e.g., histidine or an ophthalmologically acceptable derivative of histidine. In one aspect, the ring is a caprolactam ring. In some aspects where the complexing agent is a heterocyclic compound comprising at least one five-to-seven-member nitrogenous ring comprising an attached chain of at least three (3) carbons and at least one carboxylic acid group, the complexing agent is an ophthalmologically safe copolymer such as polyvinyl caprolactam-polyvinyl acetate-polyethylene glycol graft co-polymer (PCL-PVAc-PEG) or a derivative of PCL-PVAc-PEG (Summary paragraph 14).

According to certain aspects, the invention provides a pharmaceutical composition described in any of the preceding paragraphs, wherein the concentration of the compound or complexed compound within the composition, or when the composition is present within a formulation (e.g., the compositions described above are present with one or more excipients), the concentration of the compound or complexed compound within the formulation, is between about 0.1-about 10% w/v, such as between about 0.3-about 5% w/v, between about 0.6-about 5% w/v, or between about 1 and about 3% w/v, e.g., approximately 2.5% w/v. In some facets, the compositions described in this paragraph comprise a complexing agent present within the formulation at a concentration of between about 0.1% and about 10% w/v, between about 0.3-5% w/v, between about 0.6-5% w/v, or between about 1-3%, e.g., approximately 2.5 w/v %. According to aspects, the compositions described in this paragraph comprise dexamethasone or a dexamethasone compound as a second active agent, wherein the dexamethasone or a dexamethasone compound is present within the composition, or also or alternatively, when the composition is present within a formulation, the dexamethasone or a dexamethasone compound is present within the formulation, at a concentration of between about 0.01%-about 1%, such as between about 0.02%-about 0.8%, between about 0.04%-about 0.6%, between about 0.06%-about 0.4%, between about 0.08%-about 0.2%, or, e.g., at a concentration of about 0.1% (Summary paragraph 15).

According to some aspects, the invention provides a pharmaceutical composition described in any aspect, facet, or combination thereof of any preceding paragraph, wherein the rate of cornea cell permeation is detectably or significantly faster for the compound in complexed form than the non-complexed compound, or, also or alternatively, the rate of cornea cell permeation is detectably or significantly faster for the derivatized compound than tobramycin, such that the amount of compound in the cornea is increased by at least about 15% or more after a period of 60 minutes from administration (significantly in this and other contexts means that the described effect is shown to be significantly different in a sufficiently powered test/study using an appropriate test, such as a p<0.1 or p<0.05 test). In some aspects, the concentration of compound permeating the surface of the cornea is at least about 17%, in some aspects at least about 20% greater, in some aspects at least about 25% greater, in some aspects at least 40% greater, and in some aspects at least 45% greater when in complexed form than in non-complexed form or as a derivative of tobramycin than tobramycin, when measured at about 360 minutes in a corneal permeability assay (such as in an assay known in the art or the type of which is exemplified in the Examples provided herein). In some such aspects, the concentration of compound permeating the surface of the cornea is at least about 15% or greater after about 15 minutes from application than a corresponding amount of the API in TOBREX®. In certain aspects, wherein the amount of compound in the cornea is increased by at least 15%, such as at least 17%, and wherein the concentration of compound permeating the surface of the cornea is at least about 15% or greater after 15 minutes from application than a corresponding amount of the API in TOBREX®, the compound is either a derivative of tobramycin or the compound is a complexed compound and the complexing agent is histidine. In certain alternative aspects, wherein the amount of compound in the cornea is increased by at least 15%, such as at least 17%, at least 20%, at least 25%, at least 40%, or at least 45%, and wherein the concentration of compound permeating the surface of the cornea is at least about 15% or greater after 15 minutes from application than a corresponding amount of the API in TOBREX®, the compound is either a derivative of tobramycin or a complexed compound and the complexing agent is PCL-PVAc-PEG. In aspects, compositions of this paragraph are targeted to a primary indication of an eye disease, such as a microbial infection of the eye or its adnexa, and such activity of the complexed compounds of this paragraph is accompanied by a detectable or significant reduction in an indication related to the primary indication to which the composition is targeted, such as inflammation of the eye or its adnexa, attributable to the presence of, e.g., dexamethasone or a dexamethasone compound (Summary paragraph 16).

According to some aspects, the invention provides a pharmaceutical composition described in any aspect, facet, or combination thereof of any of Summary paragraphs 5-16, wherein the level of retention of the compound or complexed compound in the cornea retained after 6 hours from administration when measured by a corneal retention assay. In certain aspects, a composition of any of Summary paragraphs 5-16 and in some facets further wherein the level of retention of the compound or complexed compound in the cornea is retained after 6 hours from administration when measured by a corneal retention assay, the retention of the compound (a derivatized tobramycin compound) or the complexed compound within the cornea is at least 15% higher, such as at least 20%, such as at least 25%, or such as at least 30%, higher than the retention of the non-derivatized tobramycin or the non-complexed compound when measured at 360 minutes as measured by a standard corneal retention assay. In some further aspects, the compound or complexed compound is retained in at least about 15% or greater amount in corneal cells after 15 minutes than a corresponding amount of the API in TOBREX®. In some such facets, when the compound is present in complexed form, the complexing agent is histidine (Summary paragraph 17).

In some aspects, the invention provides a pharmaceutical composition described in any of Summary paragraphs 5-17, wherein the concentration of compound or complexed compound permeating the surface of the cornea, a collection of corneal cells, or both is at least about 17% greater, such as about 20% greater in complexed form than non-complexed form, or as a derivative of tobramycin than tobramycin, when measured at 360 minutes in a corneal permeability assay. In some aspects the concentration of compound permeating the cornea or collection of corneal cells is AOA at least about 15% or greater after 15 minutes from application than a corresponding amount of the API in TOBREX® (Summary paragraph 18).

In certain facets, the invention provides a pharmaceutical composition described in any aspect or facet of Summary paragraphs 5-18, wherein the rate of cornea cell permeation is detectably faster for the compound in complexed form than the non-complexed compound, or also or alternatively the rate of cornea cell permeation is detectably faster for a derivative of tobramycin than tobramycin, such that the amount of compound in the cornea is increased by at least about 15% or more after a period of 60 minutes from administration, and further wherein in some aspects, the concentration of compound permeating the surface of the cornea, a collection of corneal cells, or both is at least 17% greater, in some aspects at least 20% greater, in still some further aspects at least 25% greater, such as at least 40% greater, and in further aspects at least 45% greater when in complexed form than in non-complexed form or as a derivative of tobramycin than tobramycin, when measured at 360 minutes of a corneal permeability assay. In some such aspects, the concentration of compound permeating the surface of the cornea is at least about 15% or greater after 15 minutes from application than a corresponding amount of the API in TOBREX® and when complexed the complexing agent is an ophthalmologically safe derivative of PCL-PVAc-PEG having both a lipophilic and amphoteric nature (Summary paragraph 19).

According to certain aspects, the invention provides a composition comprising an effective amount of an active pharmaceutical ingredient having a structure according to Formula I, wherein the compound is not tobramycin and wherein the compound is lipophilic and amphoteric in nature and further wherein the composition is ophthalmologically safe and wherein the presence of any of the R groups of (1)-(4) promotes the uptake of the composition by corneal cells, the retention of the composition by corneal cells, or both, as compared to tobramycin, and the composition further comprises dexamethasone or a dexamethasone compound. In one aspect, the compound having the structure of Formula I in the composition, the API, is a derivative of tobramycin. In one aspect, the group of such compounds does not include tobramycin. In one aspect, the amount of API is at least 150% that of the concentration in TOBREX®, such as at least about 200%, at least about 250%, or at least about 300% the amount of tobramycin in TOBREX® (Summary paragraph 20).

According to one aspect the invention provides the composition of Summary paragraph 20, wherein the compound is a derivative of tobramycin, the derivatization of tobramycin occurs by (alternatively stated, any R group that differs from tobramycin is different from tobramycin by) substituting a 2-20 atom backbone alkyl or heteroalkyl group, through an ester or amide bond at a position corresponding to an —OH or —NH$_2$ group in tobramycin. In aspects, the alkyl or heteroalkyl group is a linear alkyl or heteroalkyl compound. Further, in aspects the group generally consists of a fatty acid, a fatty acid derivative, a short fatty acid, or a short fatty acid derivative. Still further, in aspects the group generally consist of acetic acid, an acetic acid derivative, palmitic acid, or a palmitic acid derivative. In aspects wherein the alkyl or heteroalkyl group is a linear alkyl or heteroalkyl compound, the alkyl or heteroalkyl group comprises one or more —C═O or —NH$_2$ derivative groups bound to the backbone. In certain aspects, the group comprises at least one —C═O group and at least one —NH$_2$ group bound to the backbone. In aspects wherein the alkyl or heteroalkyl group is a linear alkyl or heteroalkyl compound, the group comprises no —C═O groups (Summary paragraph 21).

In aspects, compositions of Summary paragraph 21, wherein the alkyl or heteroalkyl group comprises 1 or more —C═O or —NH$_2$ groups bound to the backbone, and where the group comprises no —C═O groups, the group comprises at least 2 —NH$_2$ groups bound to the backbone (Summary paragraph 22).

In facets, the invention provides a method according to any facet or aspect of Summary paragraph 21 or Summary paragraph 22, wherein the backbone of the group is a heteroalkyl structure comprising at least one nitrogen, at least one thiol/sulfur, or both. In certain aspects, at least about 90% of the atoms of the backbone are carbons (bound to either hydrogen, oxygen, or other atoms as well as the other backbone atoms). In further facets, the backbone comprises or is bound to an optionally derivatized 3-9-membered cycloalkyl or heterocycloalkyl (e.g., heteroaryl) ring. In certain such embodiments, in some aspects the backbone comprises or is bound to a 3-6 membered ring, such as a heterocycloalkyl or heteroaryl ring, wherein the ring comprises one or more nitro groups, is bound to one or more nitro groups, is bound to one or more side chains bound to or comprising one or more nitro groups, or both (Summary paragraph 23).

According to some aspects, as described in, e.g., Summary paragraph 23 the backbone of the group/structure comprises or is bound to an optionally derivatized 3-9 membered cycloalkyl or heterocycloalkyl ring, such as a heteroaryl ring, and more specifically the backbone comprises or is bound to a 3-6 membered ring wherein the ring comprises one or more nitro groups, is bound to one or more nitro groups, or is bound to one or more side chains bound to or comprising one or more nitro groups, and the group/structure comprises only one ring. In some aspects, such tobramycin derivatives exhibit detectably faster penetration of corneal cells than tobramycin, detectably better retention in corneal cells than tobramycin, or both (Summary paragraph 24).

In one aspect, the invention provides a method according to any composition disclosed in Summary paragraphs 20-24, wherein the compound is complexed with a lipophilic an amphoteric complexing agent. In some aspects, the complexing agent detectably increases the permeability, retention, or both permeability and retention of the compound across and/or within corneal cells. In some facets, any composition described in this paragraph comprises a complexing agent which is a heterocyclic compound comprising at least one five to seven-member nitrogenous ring comprising an attached chain of at least 3 carbons and at least one carboxylic acid group. In some aspects, such a complexing agent is an amino acid such as histidine or an ophthalmologically acceptable derivative of histidine having both a lipophilic and amphoteric nature. In some alternative aspects, the complexing agent is a copolymer such as PCL-PVAc-PEG or an ophthalmologically safe derivative of PCL-PVAc-PEG having both a lipophilic and amphoteric nature (Summary paragraph 25).

In certain facets, the invention provides any method described in Summary paragraphs 20-25, wherein the compound is present within the formulation in a concentration of between about 0.1-about 10% w/v, such as in some aspects between about 0.3-about 6% w/v, such as in some aspects between about 0.6-about 6% w/v, as in in some aspects between about 1% and about 3% w/v (or about 1-3.5% or 1.5%-3.5% w/v), as in for example in some aspects approximately 2.5% w/v. According to any such facet, in some aspects if the formulation comprises a complexing agent, the complexing agent AOA is present in the formulation in a concentration ranging from 0.1-10% w/v, such as in any of the above-described ranges. In one aspect, the ratio of complexing agent to API is AOA about 0.5:1 to about 2:1 by weight or w/v, such as about 0.75:1 to about 1.25:1 w/v, such as about 0.9:1 to about 1.1:1 w/v or about 1:1 w/v. According to aspects, the compositions described in this paragraph comprise dexamethasone or a dexamethasone compound as a second active agent, wherein the dexamethasone or a dexamethasone compound is present within the composition, or also or alternatively, when the composition is present within a formulation, the dexamethasone or a dexamethasone compound is present within the formulation, at a concentration of between about 0.01%-about 1%, such as between about 0.02%-about 0.8%, between about 0.04%-about 0.6%, between about 0.06%-about 0.4%, between about 0.08%-about 0.2%, or, e.g., at a concentration of about 0.1%. In aspects, the ratio of the amount of compound to the amount of dexamethasone or a dexamethasone compound is about 50:1, such as about 40:1, 30:1, about 20:1, or about 10:1, such as between about 15-30:1, as in, e.g., about 25:1 (Summary paragraph 26).

In some aspects, the invention provides a composition described in any of Summary paragraphs 20-26, wherein the rate of cornea cell penetration of the compound is detectably faster or significantly faster than that of tobramycin, a current formulation of tobramycin, or both. In one such aspect, the amount of the tobramycin derivative compound in the cornea is increased by at least about 15% or more after a period of 360 minutes from administration as compared to a substantially identical composition comprising a substantially identical amount of tobramycin. In certain aspects, the concentration of compound permeating the surface of the cornea or collection of corneal cells in a test method/standard is at least about 17% greater, in some facets at least about 20% greater, in some facets at least about 25% greater, in some aspects at least about 40% greater, and in some aspects at least about 45% greater than tobramycin when measured at 360 minutes in a corneal permeability assay (Summary paragraph 27).

In some aspects, the invention provides a composition described in any of Summary paragraphs 20-27, wherein the level of retention of the compound (or compound complex if a complexing agent is present) within the cornea after 6 hours from administration when measured at 360 minutes in a standard corneal retention assay is significantly greater than the level of tobramycin when administered in a substantially identical formulation in a substantially identical amount. The phrase substantially identical is used in this and other contexts to reflect that tests that would be considered substantially identical by those of skill in the art can be acceptable for assessing/defining such an aspect. It will be appreciated that the phrase "substantially identical" in such contexts comprises the use of identical amounts, identical formulations, and identical conditions in other respects (Summary paragraph 28).

In some aspects, the invention provides a composition described in any of Summary paragraphs 20-26, wherein the compound (or compound complex if a complexing agent is present) is retained in at least about 15% or greater amount in the cornea or corneal cells after 15 minutes than a corresponding amount of the API in TOBREX® when similarly administered. In certain aspects, the retention of the compound within the cornea or corneal cells as measured by a standard corneal retention assay is at least about 15% higher, such as in some aspects about 17% higher, as in in some aspects about 20% higher, as in in certain facets at least about 25% higher, such as in certain facets about 30% higher, or such as in some aspects at least about 32% higher than the retention of tobramycin in the same assay (Summary paragraph 29).

In some aspects, the invention provides a pharmaceutical formulation comprising an active pharmaceutical agent according to any one of (e.g., any one or more of) the preceding paragraphs, wherein the formulation comprises an effective amount of one or additional delivery agents selected from one or more liposome(s), microsphere(s), or both, which is amphoteric, lipophilic, and suitable for ophthalmologic applications, wherein the compound (or compound complex if a complexing agent is present) is retained in at least about 15% greater amount in corneal cells after 15 minutes than a corresponding amount of the compound when no additional delivery agent is present. In certain facets, the presence of the one or more additional delivery agents detectably or significantly enhances the permeation, retention, or both permeation of retention of the compound across and/or within corneal cells compared to a similar formulation comprising no such additional delivery agents. In some facets, such formulations further comprise one or more excipients, such as for example one or more excipients is selected from the group comprising one or more of a viscosity-enhancer, osmotic modification agent, surfactant, chelating agent, tonicity agent, buffer, pH-adjusting agent, a preservative, or water. In certain facets, at least one excipient is a viscosity enhancing excipient and in certain aspects the viscosity of the formulation is between about 10 cps and about 400 cps, such as for example a viscosity of about 25 cps to about 300 cps. In certain aspects, the viscosity is at least 5% higher than the viscosity of a similar composition which does not comprise a viscosity enhancing agent. Further, such compositions comprise a one or more additional active agents, such as an anti-inflammatory agent, e.g., a steroid such as dexamethasone or a dexamethasone compound (Summary paragraph 30).

In some aspects, the invention provides a formulation described in any aspect or facet or combination thereof of Summary paragraph 29, wherein the compound or compound complex is present in the formulation in a concentration of between about 0.1-about 10% w/v, such as for example in some aspects between about 0.3-about 5% w/v, such as in some aspects between about 0.6-about 5% w/v, as in in some facets between about 1 and about 3% w/v, such as in some facets approximately 2.5% w/v. According to some aspects, the complexing agent is present within the formulation in a concentration of between about 0.1-about 10% w/v, such as for example in some aspects between about 0.3-5% w/v, such as for example in some aspects between about 1-5% w/v, as in in some aspects approximately 2.5% w/v. In aspects a dexamethasone compound is present in the formulation in an amount of between about 0.01%-about 1%, such as between about 0.02%-about 0.8%, between about 0.04%-about 0.6%, between about 0.06%-about 0.4%, between about 0.08%-about 0.2%, or, e.g., in an amount of about 0.1% (Summary paragraph 31).

According to some facets, the invention provides a pharmaceutical formulation comprising a composition comprising a pharmaceutically active ingredient comprising a compound having a structure according to Formula I, wherein the compound is not tobramycin; wherein the compound is lipophilic and amphoteric in nature; wherein the composition is ophthalmologically safe; wherein the presence of any of the R groups of (1)-(4) promotes the uptake of the composition by corneal cells, the retention of the composition by corneal cells, or both, as compared to tobramycin; wherein the formulation comprises an effective amount of one or additional delivery agents selected from a liposome(s), a microsphere(s), or both, which is amphoteric, lipophilic, and suitable for ophthalmologic applications; wherein the compound is retained in at least about 15% greater amount in corneal cells after 15 minutes than a corresponding amount of the compound when no additional delivery agent is present; and, further, wherein the formulation comprises one or more additional active agents such as an anti-inflammatory agent, such as a steroid, e.g., a dexamethasone compound. In certain aspects, the primary compound is a derivative of tobramycin. In some aspects, the group of primary compounds so defined in this paragraph does not include tobramycin, and in other aspects it includes tobramycin (Summary paragraph 32).

According to some aspects, the invention provides a pharmaceutical formulation of Summary paragraph 32, wherein the derivatization of tobramycin occurs by (alternatively stated, any R group that differs from tobramycin is different from tobramycin by) substituting a 2-20 atom backbone alkyl or heteroalkyl group, e.g., through an ester or amide bond, at a position corresponding to an —OH or —NH$_2$ group in tobramycin. In some aspects, the alkyl or heteroalkyl group comprises, primarily comprises, generally consists of, or consists of a linear alkyl or heteroalkyl compound. In some further aspects, the group generally consists of a fatty acid (e.g., a $C_{12}$-$C_{18}$ fatty acid), a fatty acid derivative, a short fatty acid (e.g., a $C_2$-$C_4$ fatty acid), or a short fatty acid derivative. In some still further facets, the group generally consist of acetic acid, an acetic acid derivative, palmitic acid, or a palmitic acid derivative (Summary paragraph 33).

In aspects, the invention provides a formulation of Summary paragraph 33, wherein the alkyl or heteroalkyl group is a linear alkyl or heteroalkyl compound wherein the alkyl or heteroalkyl group comprises one or more —C=O or —NH$_2$ groups bound to the backbone. In certain facets, the group comprises at least one —C=O group and at least one —NH$_2$ group bound to the backbone. In some aspects wherein the alkyl or heteroalkyl group is a linear alkyl or heteroalkyl compound wherein the alkyl or heteroalkyl group comprises one or more —C=O or —NH$_2$ derivative groups bound to the backbone, the group comprises no —C=O groups. In some aspects, the invention provides a compound having such a formula wherein the group comprises at least two —NH$_2$ groups bound to the backbone. In some further aspects, the backbone of the group is a heteroalkyl structure comprising at least one nitrogen, at least one thiol/sulfur, or both. In some still further facets, at least about 90% of the atoms of the backbone are carbons. According to some yet further aspects, the backbone comprises or is bound to an optionally derivatized 3-9-membered cycloalkyl or heterocycloalkyl ring (e.g., a heteroaryl ring, such as a heteroaryl ring comprising one or more nitrogen groups, such as 1-4 nitrogen groups). In such cases, in some facets, the backbone comprises or is bound to a 3-6 membered ring wherein the ring comprises one or more nitro groups, is bound to one or more nitro groups, is bound to one or more side chains bound to one or more nitro groups, or comprises a combination of any or all thereof. In certain related aspects, the group(s) bound to the backbone comprise(s) only one ring. In some aspects, the described formulations provide a tobramycin derivative which exhibits detectably faster penetration of corneal cells than tobramycin, detectably better retention in corneal cells than tobramycin, or both (Summary paragraph 34).

In some aspects, the invention provides a formulation described in Summary paragraphs 32-34, wherein the compound is complexed with a lipophilic and amphoteric, complexing agent. In certain aspects, the complexing agent detectably increases the permeability, retention, or both permeability and retention of the compound across and/or within corneal cells, and further the formulation comprises dexamethasone or a dexamethasone compound (Summary paragraph 35).

In some facets, the invention provides a formulation described in Summary paragraph 33, wherein the complexing agent is a heterocyclic compound comprising at least one five-to-seven-member nitrogenous ring comprising an attached chain of at least 3 carbons and at least one carboxylic acid group. In certain facets, the complexing agent is an amino acid, such as, e.g., histidine or an ophthalmologically acceptable derivative of histidine having both a lipophilic and amphoteric nature. In certain facets, the complexing agent is a copolymer, such as PCL-PVAc-PEG or an ophthalmologically safe derivative of PCL-PVAc-PEG having both a lipophilic and amphoteric nature (Summary paragraph 36).

In some aspects, the invention provides a formulation described in any of Summary paragraphs 32-36, wherein the presence of the one or more additional delivery agents significantly enhances the permeation, retention, or both permeation and retention of the compound across and/or within corneal cells compared to a similar formulation comprising no additional delivery agents. In certain facets, such formulations further comprise one or more excipients, such as e.g., one or more excipients selected from the group comprising one or more of a viscosity-enhancer, osmotic modification agent, surfactant, chelating agent, tonicity agent, buffer, pH-adjusting agent, a preservative, or water. In certain facets at least one excipient is a viscosity enhancing excipient, and, in some facets, the viscosity of the formulation is between about 10 cps and about 400 cps, such as for example in some facets about 25 cps to about 300 cps. In some facets, the viscosity is at least 5% higher than the viscosity of a similar composition which does not comprise a viscosity enhancing agent. In aspects, the formulation comprises dexamethasone or a dexamethasone compound as one of one or more additional active agents (Summary paragraph 37).

In some aspects, the invention provides a formulation described in any of Summary paragraphs 32-37, wherein the compound (or as applicable the complexed compound) is present in the formulation in a concentration of between about 0.1-about 10% w/v, such as in some aspects between about 0.3-about 5% w/v, such as in some aspects between about 0.6-about 5% w/v, as in in some facets between about 1 and about 3% w/v, such as in some aspects approximately 2.5% w/v. In certain such formulations, in some aspects the complexing agent, when present, is present in the formulation in a concentration of between about 0.1-10% w/v. In aspects, such formulations further comprise dexamethasone or a dexamethasone compound in an amount of between about 0.01-1% w/v (Summary paragraph 38).

According to some aspects, the invention provides a pharmaceutical formulation comprising an antimicrobial active pharmaceutical ingredient comprising an effective amount of a compound having a structure according to Formula I and an effective amount of a liposome or microsphere delivery agent, which is amphoteric, lipophilic, and suitable for ophthalmologic applications, wherein the compound is retained in at least about 15% greater amount in corneal cells after 15 minutes than a corresponding amount of the compound when not present with the liposome or microsphere delivery agent, and wherein the compound is not tobramycin. In some aspects, the compound is present in a composition in an amount that is at least about 150%, at least about 200%, at least about 250%, or at least about 300% of the current concentration of tobramycin in TOBREX®. Further, such formulations can comprise dexamethasone or a dexamethasone compound in an amount wherein the ratio of the primary compound or compound complex to dexamethasone or dexamethasone compound is between about 50:1-about 1:1, such as between about 40:1-about 10:1, between about 30:1-about 20:1, or in a ratio of about 25:1 (Summary paragraph 39).

According to some aspects, the invention provides a formulation as described in Summary paragraph 39, wherein the primary compound/API is complexed with a complexing agent comprising a heterocyclic (e.g., heteroaryl) compound comprising at least one five to seven member nitrogenous ring comprising an attached chain of at least 3 carbons and at least one carboxylic acid group. In some aspects, the complexing agent is an amino acid such as histidine or an ophthalmologically acceptable derivative of histidine having both a lipophilic and amphoteric nature, and that detectably or significantly enhances the speed of uptake of the complex by corneal cells, the uptake/retention of the complex by corneal cells, or both. In certain alternative aspects, the complexing agent is a copolymer, such as PCL-PVAc-PEG or an ophthalmologically safe derivative of PCL-PVAc-PEG having both a lipophilic and amphoteric nature and that detectably or significantly enhances the speed of uptake of the complex by corneal cells, the uptake/retention of the complex by corneal cells, or both. In certain facets, the presence of the complexing agent significantly enhances the permeation, retention, or both permeation and retention of the compound across, within, or both across and/or within corneal cells compared to a similar formulation comprising no complexing agent (Summary paragraph 40).

In certain aspects, the invention provides a formulation described in any of Summary paragraphs 39-40, wherein the formulation further comprises one or more excipients that provide one or more properties to the formulation, such as a preservative function, a buffering function, and the like. In one aspect, the one or more excipients is selected from the group comprising one or more of a viscosity-enhancer, osmotic modification agent, surfactant, chelating agent, tonicity agent, buffer, pH-adjusting agent, a preservative, or water. In some facets, at least one excipient is a viscosity enhancing excipient. According to some aspects, the viscosity of the formulation is between about 10 cps and about 400 cps, such as for example a viscosity of about 25 cps to about 300 cps. In certain facets, the viscosity is at least about 5% higher (e.g., at least about 7% higher, at least about 10% higher, or at least about 15% higher) than the viscosity of a similar composition which does not comprise the viscosity enhancing agent or any viscosity enhancing agent. Further, such formulations comprise dexamethasone or a dexamethasone compound as one of one or more additional active agents (Summary paragraph 41).

According to some facets, the invention provides a formulation described in any of Summary paragraphs 39-41, wherein the primary compound or compound complex is present in the formulation in a concentration of between about 0.1-about 10% w/v, such as in some aspects between about 0.3-about 5% w/v, such as in some aspects between about 0.6-about 5% w/v, as in in some facets between about 1 and about 3% w/v, such as in some aspects approximately 2.5% w/v, in certain facets, the complexing agent, when present, is present in the formulation in a concentration of between about 0.1-10% w/v (e.g., about 0.05-0.25% w/v or about 0.9-9% w/v or about 1.2-7.2% w/v), and in aspects dexamethasone is present in the formulation in an amount of between about 0.01-1% (e.g., between about 0.05-0.5%) (Summary paragraph 42).

According to certain aspects, the invention provides a formulation described in any facet, aspect, or combination thereof described in any of Summary paragraphs 30-42, wherein the compound is retained in at least about a 15% greater amount in corneal cells after 15 minutes than the API in TOBREX® as measured by a corneal cell retention assay. In some aspects, any of the formulations described in any of the above paragraphs is/are delivered as a solution, emulsion, dispersion, or suspension. In some facets, the formulation is delivered as a solution, and in further facets, can be administered via drops to the eye. In certain alternative aspects, the formulation is delivered as an ointment, and in further aspects, can be administered by applying a strip of the ointment to the eye. In certain embodiments, any of the formulations described by this paragraph maintain the compound in contact with the ocular surface (mucous membrane) of the eye for at least 2 hours after application, such as in some aspects for at least approximately 4 hours after application, such as in some aspects for at least approximately 8 hours after application, as in in some facets for at least approximately 16 hours after application, as in in some aspects for at least approximately 20 hours after application, or such as in certain aspects for at least approximately 24 hours after application (Summary paragraph 43).

According to some aspects, the invention provides a formulation described by any aspect, facet, or combination of aspects and facets described in Summary paragraphs 30-43, wherein the formulation comprises one or more additional active pharmaceutical ingredients (APIs). In aspects, the API is an anti-inflammatory. In certain further facets, the additional active AOA is a steroid, such as, e.g., dexamethasone. In still another aspect, the additional active AOA includes at least one additional antibiotic. In one aspect, a composition is provided and methods are provided wherein two different compounds according to Formula I, Formula II, or Formula III are administered in association or are co-formulated and/or co-administered Summary paragraph 44).

In this and in other respects, the ophthalmic tobramycin compositions described herein can exhibit important advantages and differences over conventional ophthalmologic tobramycin products and formulations, such as, in some aspects, being able to increase the availability of tobramycin or a tobramycin derivative, extending residence time of such APIs with the cornea, increasing the penetration through the cornea, or providing controlled release of active into the eye tissues, leading to different or improved properties and applications. These and other properties of the compositions of the invention and methods of using such compositions are described below in the Detailed Description of the Invention part of this disclosure (Summary paragraph 45).

BRIEF DESCRIPTION OF THE DRAWINGS/FIGURES

The drawings/figures provided here, and the associated following brief description of figures, are intended to exemplify certain aspects and principles of the invention, without limiting the scope of either thereof.

(FIG. 4C).

DETAILED DESCRIPTION OF THE INVENTION

Construction, Definitions, & Acronyms

Figure 1A:
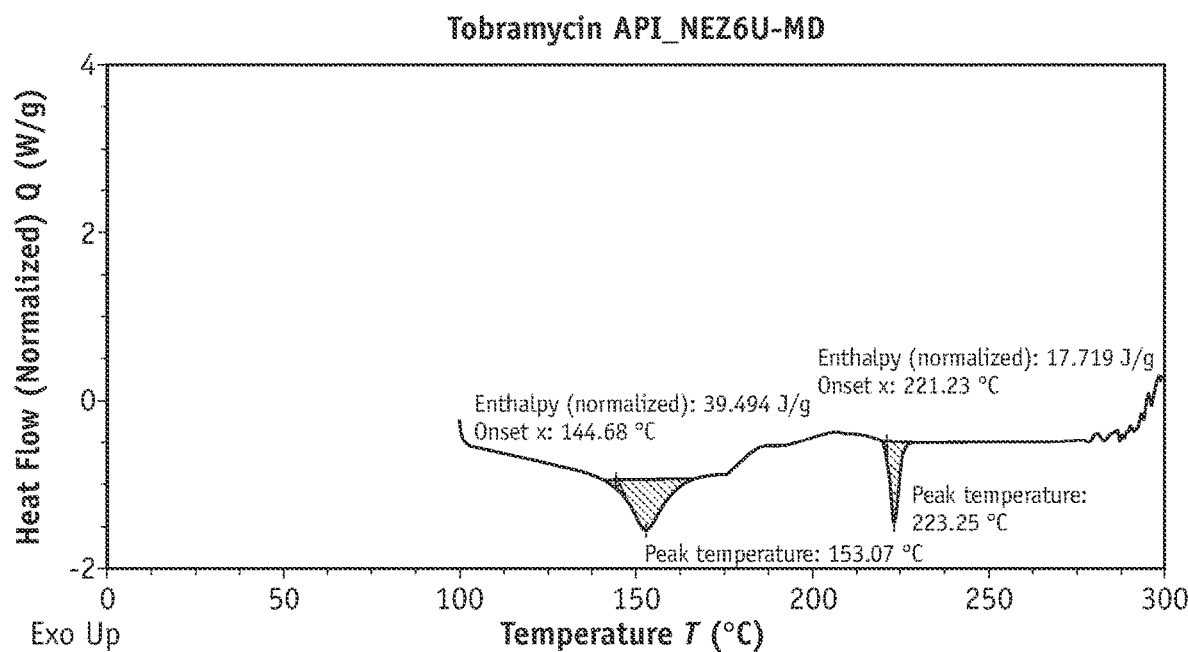
FIGS. 1A-1D are differential Scanning Colorimetry (DSC) spectra of tobramycin (FIG. 1A), histidine (FIG. 1B), a tobramycin+histidine physical mixture (FIG. 1C), and a tobramycin+histidine complex according to one aspect of the invention (FIG. 1D).
Figure 1B:
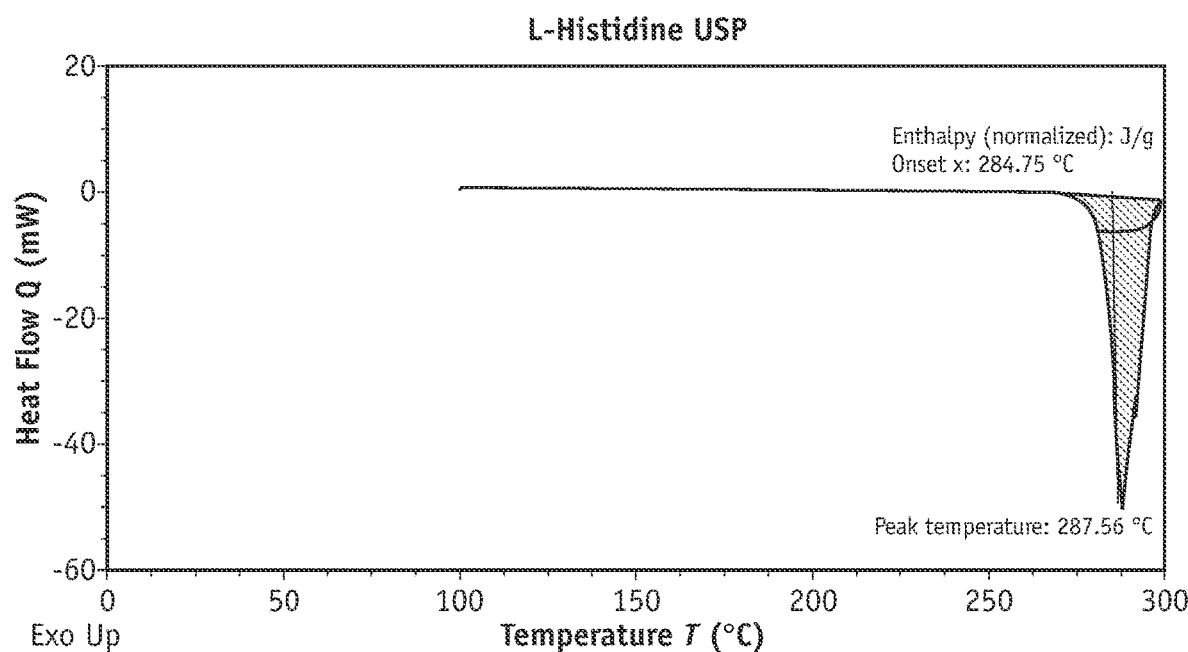

To aid in the understanding of the disclosure provided herein, the following principles should be considered.

"Uncontradicted" means not contradicted explicitly, clearly by context, or by inoperability/impossibility.

Terms such as "here" & "herein" means "in this disclosure." Except where otherwise specified, any part if this disclosure is applicable to any other suitable part of the disclosure.

The invention described here includes several aspects. Uncontradicted, "aspects," means "aspects of this invention." The "invention" encompasses all aspects herein, individually & collectively (methods and devices/systems/compositions).

Heading(s) here are used for convenience only. Except where clearly otherwise indicated, aspects under a heading can be combined with other aspects described in any section of the disclosure. Heading(s) do not limit the scope of any aspect.

Uncontradicted, "a," "an," "the," and similar referents indicate both the singular and the plural of any associated element. Uncontradicted, terms in the singular implicitly convey the plural and vice versa here (e.g., a passage referring to use of an "element" implicitly discloses use of corresponding "elements"). Uncontradicted, "also" means "also or alternatively." The "I" symbol is sometimes used to indicate an "or" relationship between elements (e.g., "A/B" means "A or B"). A slash symbol can also indicate an element with two names. Terms like "combination," "and combinations," or "or any combinations" regarding listed elements mean "a combination of any or all of such elements."

Uncontradicted, each member of each list of elements reflects an independent aspect (often having distinct/nonobvious properties with respect to the other listed elements/aspects or features).

Ranges here concisely refer to values within the range within an order of magnitude of the smallest endpoint. E.g., readers should interpret "1-2" as implicitly disclosing each of 1.0, 1.1, 1.2, 1.3, 1.4, 1.5, 1.6, 1.7, 1.8, 1.9, & 2.0, "5-20" as implicitly disclosing each of 5, 5.1, 5.2, . . . , 6, 6.1, 6.2, . . . 19, 19.1, . . . , 19.9, and 20, and "10-20" is to be interpreted as implicitly providing support for each of 10, 11, 12, 13, . . . , 19, & 20. Ranges here include end points, regardless of how the range is described (e.g., a range "between" 1 and 5 will include 1 and 5 in addition to 2, 2.1, . . . , 3, 3.1, . . . , 4, 4.1, . . . , and 4.9), unless the exclusion of such endpoints is clearly indicated, regardless of the terminology used to describe the range. Uncontradicted, applying a modifier to 1 or 2 endpoints does not change the range's value (e.g., "about 10-20" means "about 10-about 20").

Terms of approximation, e.g., "about" or "approximately" (or ~) here refer to a range of closely related values, value(s) difficult/impossible to precisely measure, or both, and, thus, include the precise value as an aspect of the disclosure (e.g., "10" is an aspect of a disclosure of "about 10"). Similarly, precise values provided here support approximately similar ranges unless contradicted. The scope of an approximate value depends on the value, context, and technology (e.g., criticality or operability, other evidence, statistical significance, or general understanding). In the absence of guidance here or in the art, terms of approximation such as "about" or "approximately" mean+/−10% of the indicated value(s).

Uncontradicted, "or" means "and/or" here. The occasional explicit use of "and/or" herein has no effect on this interpretation of "or." Uncontradicted, the scope of "or" meaning "and/or" in a phrase such as "A, B, and/or C" or "A, B, and C" implicitly supports each of the following embodiments: A, B, and C; A, B, or C; A or C; A or B; B or C; A and C; A and B; B and C; A (alone); B (alone); and C (alone). Uncontradicted, methods described here be performed in any suitable order. Uncontradicted, devices/compositions can be assembled/generated in any suitable manner by any suitable method. Uncontradicted, any combination of elements, steps, components, or features of aspects and apparent variations thereof, each constitute separate aspects of the invention.

Numerous examples of aspects, elements, or steps are provided in this disclosure to illuminate aspects. The breadth and scope of the invention should not be limited by any such exemplary elements or embodiments. No language in the specification should be construed as indicating any element is essential to the practice of the invention unless such a requirement is explicitly stated.

Although this document provides support for "means-plus-function" style interpretation of certain elements of the invention, both explicitly and implicitly, unless "means for" or "step for" are used here, no element should be given a "means-plus-function" construction. Terms like "configured to" or "adapted to" are not "means-plus-function" terms, but, rather, refer to features configured, designed, selected, or otherwise adapted to achieve a performance, characteristic, property, or the like using this disclosure and technology.

The description herein of any aspect or embodiment using terms such as "comprising", "having," "including," or "containing" with reference to an element, composition, or set of compositions or elements should be interpreted, whether explicitly stated or not, as simultaneously providing support for a similar aspect or embodiment that "consists of", "substantially comprises," "materially comprises," "predominately comprises," "largely consists of," and "substantially consists of" that particular element, unless otherwise stated or clearly contradicted by context (i.e., a composition described herein as comprising a particular element should be understood as also describing a composition consisting of that element, substantially comprising that element, predominately comprising that element, largely consisting of that element, and substantially consisting of that element, unless otherwise stated or clearly contradicted by context). Terms such as "including", "containing", and "having"

should otherwise be interpreted openly herein, e.g., as meaning "including, but not limited to", "including, without limitation", or "comprising", unless otherwise such a meaning is clearly contradicted.

The term "substantially comprises" means that at least about 1% of a composition, population, or similar collection is or is made up of/by the referenced feature, species, or element, and typically means (and should be understood as providing support for) the relevant feature makes up or represents at least about 5%, at least about 10%, or even at least about 15% of the total amount of the composition or number of the population.

"Materially comprises" means that at least about 20% of a composition, population, or similar collection is or is made up of/by the referenced feature, species, or element, and typically means (and should be understood as providing support for) the relevant feature makes up or represents at least about 25%, at least about 30%, or even at least about 40% of the total amount of the composition or number of the population.

"Predominately comprises" means accounting for more than one half (i.e., more than 50%) of a feature (e.g., a composition or a population of things). This amount and similar amounts used in respect of defined terms provided herein can be on a weight percent (weight/weight) basis, on a molecule/molecule basis, or other relevant basis used in the context of the relevant disclosure. For example, if a composition is described as "predominately comprising" element/species A, more than 50% of the composition on a molecular and/or weight basis will be made up of element/species A). Wherever this term is used it should be understood as simultaneously providing support for more than 60%, more than 70%, and more than 80% of the component or composition or collection being made up of the feature, species, or element at issue. The term "most" should also be construed similarly herein.

"Largely consists of" means that at least about 75% of the composition, population, or the like is or is made up of the referenced feature, species, or element at hand and should be understood as providing disclosure that at least 82.5%, at least 87.5%, at least 92.5%, and at least 97.5% of the composition, population, or the like is or is made up of/by the referenced feature, species, or element. Obviously, the remaining minority portion of the relevant composition, collection, and the like can be composed of other compounds, materials, or other relevant elements. The phrases "largely all" and "largely most" should be construed similarly.

"Substantially consists of" means at least ~90% of the composition, population, or the like is made up of the referenced feature, species, or element and should be understood as also providing disclosure that at least ~95%, at least ~99%, or at least ~99.9% of the composition, collection, etc., is made up of the relevant element, feature, or thing. The phrases "nearly all" and "nearly entirely" should be construed similarly.

Changes to tense or presentation of terms (e.g., using "comprises predominately" in place of "predominately comprises") do not modify the meaning of the related phrase unless indicated. "Significant" and "significantly" means results/characteristics that are statistically significant using an appropriate test in the given context (e.g., $p \leq 0.05/0.01$). "Detectable" means measurably present/different. The abbreviation "DOS" means "detectable or significant" or "detectably or significantly."

The intended audience for this disclosure ("readers") are persons having ordinary skill in the art in the practice of the technologies discussed herein ("skilled persons"). Technological aspects of elements/steps provided here are sometimes omitted in view of the knowledge of readers. The terms "technology" and "art" here refer to the knowledge of such skilled persons. In cases, citation of reference(s) adaptable to aspects are included here. All such patent documents and other publications are hereby incorporated by reference to the same extent as if each reference were individually and specifically indicated to be incorporated by reference and were set forth in its entirety herein. The disclosure of such references can be combinable with this disclosure; however, incorporation of patent documents is limited to the technical disclosure thereof and does not reflect on validity, patentability, or enforceability thereof. Moreover, in the event of any conflict between this disclosure and the teachings of such documents, the content of this disclosure will control with respect to properly understanding various aspects. Readers will also understand that some features of some cited references are not applicable to aspects.

Unless clearly indicated, the scope of any aspect or embodiment is not limited to processes, compositions, or methodologies described, as these may vary. The terminology used in the description is for the purpose of describing particular versions or embodiments only; and is not intended to limit the scope of any aspects. Unless defined otherwise, all technical and scientific terms used herein have the same meanings as commonly understood by one of ordinary skill in the art. Any methods and materials similar or equivalent to those described herein can be used in the practice or testing of embodiments of the invention, the methods, devices, and materials described herein.

The description of the specific embodiments provided herein will reveal the general nature of the invention such that others can, by applying knowledge within the skill of the art, readily modify and/or adapt for various applications such specific embodiments, without undue experimentation, without departing from the general concept of the invention. Therefore, such adaptations and modifications are intended to be within the meaning and range of equivalents of the disclosed embodiments, based on the teaching and guidance presented herein. In general, it is to be understood that the phraseology or terminology herein is for the purpose of description and not of limitation, such that the terminology or phraseology of the present specification is to be interpreted by the skilled artisan in light of the teachings and guidance.

Compounds of the Invention

Provided here are compositions comprising one or more pharmaceutically suitable and pharmaceutically active compounds which, in some facets, are or are identifiable as being closely related to compounds of the aminoglycoside 4,6-disubstituted deoxystreptamine sub-class. In aspects, such compounds comprise tobramycin or a compound similar to tobramycin. In aspects, such compounds are referred to as a "primary compound" herein, as such compounds can be present in a formulation which further comprises one or more excipients or one or more additional active pharmaceutical ingredients. In aspects, the compounds described herein are derivatized analogues of tobramycin wherein, e.g., any one or more hydroxy groups or amide groups present on the naturally occurring compound are substituted with one or more groups that are lipophilic, amphoteric, ophthalmologically acceptable, and which do not significant reduce the antibiotic properties of the compound as compared to tobramycin, or that also enhance the ability of the compound to penetrate corneal cells faster, penetrate in higher concentrations (e.g., an increased amount of the compound is capable of penetrating), or be retained in corneal cells in higher concentrations, or any or all thereof, as compared to tobramycin. Such an increase in the permeability, uptake, retention, or any combination of permeability (rate or concentration as described above), uptake, or retention of the compounds described herein by the cornea provide an opportunity for beneficial improvements in active concentration and dosing regimens over currently available tobramycin treatments, yielding further improvement in clinical outcome measures (e.g., efficacy) or patient experience (e.g., improved tolerability, compliance) as is described herein. In aspects, non-complexed, derivatized compounds of the invention can provide similar or equivalent corneal cell penetration, similar or equivalent corneal cell penetration rates, similar or equivalent corneal cell retention, or any combination thereof, to complexed compounds, such corneal cell penetration, penetration rates, and retention of such complexes described herein. In aspects, corneal cell penetration, penetration rates, and retention of non-complexed, derivatized tobramycin compounds described herein are higher than that of non-derivatized tobramycin.

The term "tobramycin" generally can be interpreted to refer to tobramycin in any suitable form, including any pharmaceutically acceptable salts, pharmaceutically acceptable solvates, pharmaceutically acceptable hydrates, and the like that one of ordinary skill would view as substitutable for another form of tobramycin. When making a comparison of the activity, efficacy, or other quality of the compositions or compositions of the invention to on-market products, such as a comparison of the compositions described herein to TOBREX® or TOBRADEX ST® or the compounds herein the to the API of TOBREX® or TOBRADEX ST®, it should be understood that such disclosure encompasses such comparison(s) to similar or equivalent on-market products, such as an equivalent generic product or a composition having a shared active ingredient for similar applications. In aspects, the tobramycin of compositions comprises a compound comprising the same basic structure of tobramycin in these compositions.

In general, the compounds disclosed herein find particular use in ophthalmological conditions. Such compounds are pharmaceutically acceptable, and effective as antibiotics in the eye. Further description of such characteristics associated with all, several, and some of the compounds of the invention are included herein.

As noted above, tobramycin (full chemical name 0-{3-amino-3-deoxy-α-D-gluco-pyranosyl-(1→4)}-0-{2,6-di-amino-2,3,6-trideoxy-α-D-ribohexo-pyranosyl-(1→6)}-2-deoxystreptamine (structure shown below) is an FDA approved aminoglycoside for the treatment of external eye infections. It is a highly water-soluble aminoglycoside, having a solubility in water of 94 mg/mL and a log partition coefficient of −5.8. It has antibiotic activity against a wide variety of gram-negative and gram-positive ophthalmic pathogens. Tobramycin has the following structure:

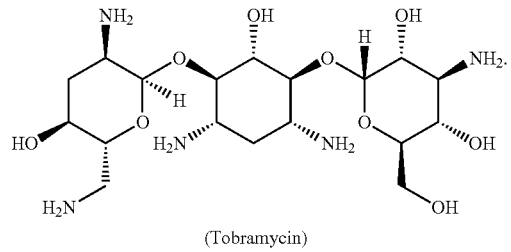 [SMILES: NC[C@H]1O[C@H](O[C@H]2[C@H](O)[C@@H](O[C@H]3O[C@H](CO)[C@@H](O)[C@H](N)[C@H]3O)[C@H](N)C[C@@H]2N)[C@H](N)C[C@@H]1O]

(Tobramycin)

The invention provides complexes that comprise a tobramycin compound, such as tobramycin, and exhibit different or improved properties as compared to noncomplexed tobramycin compounds, such as counterpart tobramycin compounds, e.g., in terms of the ability of the complexed composition to permeate corneal cells, be retained or taken up by such corneal cells, or both, and novel functional formulations that also include tobramycin and achieve similar results.

The invention also includes derivatives of tobramycin that can achieve these properties, independent of any complexing agent or formulation.

In aspects, a tobramycin derivative, such as a tobramycin derivative with such above-described properties, can be further combined with a complexing agent, functional formulation, or both, with the properties of the derivative, complexing agent, or functional formulation all contributing to an enhanced ability to permeate corneal cells, be retained or taken up by corneal cells, or both.

In one aspect, compounds that are provided herein or that can be contained in a complex or functional formulation provided herein comprise a structure according to the formula below:

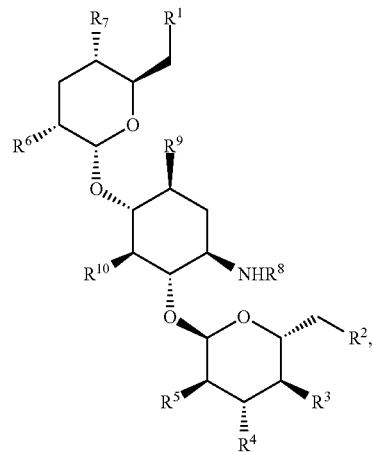

wherein $R^1$-$R^{10}$ are as described in the following paragraphs below (Formula I).

In certain aspects, position $R^1$ is —CH—$NH_2$ (i.e., Me—$NH_2$). In certain alternative aspects, position $R^1$ is substituted with a group selected from the group comprising a/an optionally substituted alkyl, aryl, aralkyl, cycloalkyl, cycloalkylalkyl, heterocyclyl, heterocyclylalkyl, heteroaryl, or heteroarylalkyl. The term optionally substituted in such a phrase is intended to apply to all members of the listed group (including, e.g., cycloalkylalkyl and heteroaryl). The use of overlapping groups/terms above and in other aspects of this disclosure is not intended to apply any exclusion. Thus, for example, although heterocyclyl and heteroaryl are both recited above and in other lists herein, it will be understood that reference to a heterocyclyl encompasses both aromatic and nonaromatic heterocyclic compounds unless otherwise stated or clearly indicated by the disclosure.

Chemical terminology, such as to describe various R groups of compounds, is well understood in the art and, as such, only general guidance is provided here to clarify the scope of certain aspects and to provide examples to better illuminate this disclosure. Where those of skill in the art would understand such terms to encompass groups not exemplified or other scope not described, such additions to the terms provided herein should be considered within the broadest scope of this disclosure as an additional facet of the described composition, method, or compound. Given the knowledge in the art not all terms used in the disclosure may be specifically described here, but such terms will nonetheless be understood by the skilled reader given ordinary practice in the art.

The term "alkyl" typically refers to a group having the general formula $C_nH_{2n+1}$, wherein the hydrocarbon chain is straight or branched containing only carbon and hydrogen atoms; simply for group definition purposes, examples include methyl $CH_3$ (derived from methane) and butyl $C_2H_5$ (derived from butane). In one aspect such alkyl groups will contain from between one and 12 carbon atoms ($C_1$-$C_{12}$ alkyl), such as, for example 1-12, 1-8, or 1-6 carbon atoms, and which is attached to the rest of the molecule by a single bond.

The term "aryl" typically refers to any functional group or substituent comprising or derived from an aromatic ring, for example an aromatic hydrocarbon; simply for group definition purposes, a simple exemplary aryl group is phenyl $C_6H_5$. In aspects, aryl groups can contain between 6-18 carbon atoms (e.g., 6-18, 10-18, 14-18, or for example 6-14, 6-12, or 6-8 carbon atoms) along with the at least one aromatic ring.

An "aralkyl" typically refers to a univalent radical derived from an alkyl radical by replacing one or more hydrogen atoms by aryl groups (an aryl-substituted alkyl radical, or alternatively stated, a radical in which an aryl group is substituted for a hydrogen atom of an alkyl group).

As used herein, "cycloalkyl" typically refers to a group having the general formula $C_nH_{2-1}$ and is derived from a cycloalkane by removal of a hydrogen atom from a ring (e.g., a univalent radical such as cyclohexyl, cyclobutyl, cyclopentyl, cycloheptyl, and cyclooctyl formed by removal of one hydrogen atom from a cycloalkane). Typically, a cycloalkyl will have between three to 15 carbon atoms, e.g., three—10 carbon atoms.

As used herein, "cycloalkylalkyl" typically refers to an alkyl radical which is substituted by a cycloalkyl radical containing from ~three-~eight (e.g., three-six) carbon atoms.

In aspects, alkyl groups and other referenced groups described herein can be optionally substituted with one or more substituents. An alkyl group or other substituted group can be, e.g., mono-substituted (having only one substituent), or 1-2 substituents, or 1-3 substituents, or 1-4 substituents, etc. The substituents can be selected from the group consisting of hydroxy, amino, alkylamino, boronyl, carboxy, nitro, thiol, and the like. When an alkyl group incorporates one or more heteroatoms, the alkyl group is referred to herein as a "heteroalkyl" group. Similar modifications apply to other optionally substituted groups described herein, which can be similarly described using "hetero" terminology (e.g., a heteroaryl group being an aryl group comprising one or more non-carbon atoms in an aromatic backbone, such as an imidazole conjugate). As noted elsewhere herein in some cases substituents are added to a backbone of a compound, are bound to a backbone of a compound, or a heterocompound comprises both substituents in the backbone and bound to the backbone of a compound.

As used herein, terms like "heterocyclyl" or sometimes called a "heterocyclic ring" typically refers to any univalent radical derived from a heterocycle by removal of an atom of hydrogen from any ring atom. For the purpose of group definition only, examples of heterocyclyl radicals include but are not limited to dioxolanyl, decahydroisoquinolyl, imidazolinyl, piperidinyl, pyrrolidinyl, and thiazolidinyl)

As used herein, the term "heterocyclylalkyl" typically refers to a radical of the formula $R_aR_e$, where $R_a$ is an alkyl radical and $R_e$ is a heterocyclyl radical, and if the heterocyclyl is a nitrogen-containing heterocyclyl, the heterocyclyl can be attached to the alkyl radical at the nitrogen atom.

As noted above, as used herein, terms such as "heteroaryl" refers to an aromatic ring (e.g., a ring of 5 or 6 members) wherein the ring is aromatic and has at least one non-carbon constituent. With respect to these compounds, in some facets, any one or more of positions $R^4$, $R^6$, $R^8$, and $R^9$ are —$NH_2$. In certain alternative facets, any one or more of positions $R^4$, $R^6$, $R^8$, and $R^9$ comprise a substitution made with a member of a group selected from the group comprising a/an optionally substituted alkyl, aryl, aralkyl, cycloalkyl, cycloalkylalkyl, heteroalkyl, heterocyclyl, heterocyclylalkyl, heteroaryl, or heteroarylalkyl.

According to some aspects, position $R^2$ is —Me—OH. According to some alternative aspects, position $R^2$ is substituted with a group selected from the group comprising a/an aryl, aralkyl, cycloalkyl, cycloalkylalkyl, heterocyclyl, heterocyclylalkyl, heteroaryl, or heteroarylalkyl.

According to certain facets, any one or more of positions $R^3$, $R^5$, $R^7$ and $R^{10}$ is —OH. In certain alternative facets, any one or more of $R^3$, $R^5$, $R^7$ and $R^{10}$ is substituted with a group selected from the group comprising a/an aryl, aralkyl, cycloalkyl, cycloalkylalkyl, heterocyclyl, heterocyclylalkyl, heteroaryl, or heteroarylalkyl.

In some specific embodiments of the invention, the compound is any compound described above wherein no more than three, such as for example no more than five, no more than three, no more than two, or no more than one of positions $R^1$, $R^2$, $R^3$, $R^4$, $R^5$, $R^6$, $R^7$, $R^8$, $R^9$, and $R^{10}$ differ in composition from the corresponding position in tobramycin.

In aspects, the compounds of the invention or compounds that are combined with a complexing agent or functional formulation of the invention comprise a structure according to the formula below:

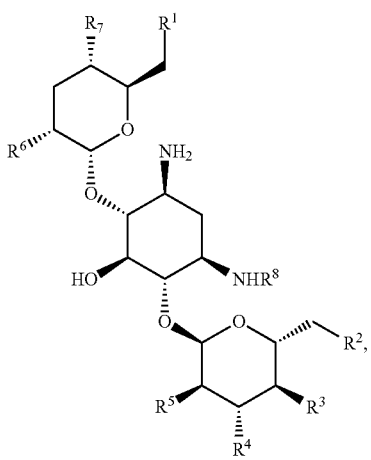

wherein $R^1$-$R^8$ are as described in the following paragraph (Formula II).

In some facets, such compounds comprise no more than four, such as no more than three, no more than two, or no more than one variation(s) at position(s) $R^1$, $R^2$, $R^3$, $R^4$, $R^5$, $R^6$, $R^7$, and $R^8$ with respect to corresponding position(s) in tobramycin (e.g., no more than three positions $R^1$-$R^8$ vary from corresponding positions in tobramycin). In aspects, any one or more of $R^1$-$R^8$ of such compounds correspond to the $R^1$-$R^8$ groups of Formula I. In aspects, the groups at positions $R^2$, $R^7$, or both $R^2$ and $R^7$ are the same as those in the corresponding positions in tobramycin. In aspects of such an embodiment, $R^2$ is a —Me—Oh and $R^7$ is an —OH; that is, these positions have the same composition as the corresponding positions in tobramycin.

According to certain aspects, the compounds of the invention or compounds that are combined with a functional formulation or complexing agent to achieve improved permeation or retention properties have a structure according to the formula below:

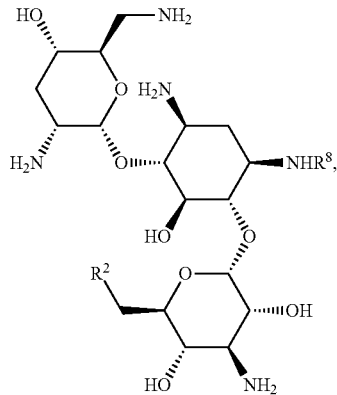

wherein R groups are as described in the following paragraph (Formula III).

In certain aspects, any R group of such compounds ($R^2$ or $R^8$) can be the same as corresponding R groups described in Formula I, Formula II, or both Formula I and Formula II. In certain facets, any R group of such compounds ($R^2$ or $R^8$ as shown) that differs from tobramycin can include an optionally derivatized 2-20 (e.g., 2-20, 2-16, 2-12, 2-8, 2-4, or for example 6-20, 10-20, 14-20, or 18-20, atom backbone alkyl or heteroalkyl group. In one aspect, the group is a heteroalkyl group. The term "backbone" in this and other contexts of the disclosure will be understood as referring to a continuous chain of atoms to which either hydrogens or other atoms or groups can be bound. Such an alkyl or heteroalkyl group can be attached by any chemically appropriate bond. In certain aspects, such a group is attached through an ester or amide bond at a position corresponding to an —OH or —$NH_2$ group in tobramycin. According to some aspects, the alkyl or heteroalkyl group primarily comprises, generally consists of, or consists of a linear alkyl or heteroalkyl compound. Such a linear alkyl or heteroalkyl compound can be any suitable linear alkyl or heteroalkyl compound which is pharmaceutically acceptable, ophthalmologically safe, preferably comprises an amphoteric, lipophilic, or both amphoteric and lipophilic nature, is capable of maintaining stability, and does not negatively alter the trans-corneal mobility or uptake/retention of the compound or its antibiotic properties. In certain aspects, such a linear alkyl or heteroalkyl compound detectably enhances, e.g., measurably increases, such as statistically improves, the corneal permeation, retention/uptake, or both the corneal permeation and retention/uptake of the compound. In certain aspects, the group generally consists of a fatty acid or fatty acid derivative that is conjugated to the core structure of the compound. According to some aspects, such a fatty acid, short fatty acid, or derivative of a fatty acid or short fatty acid can be any fatty acid suitable according to the characteristics previously described. In certain aspects, the fatty acid is acetic acid. In certain alternative aspects, the fatty acid is a derivative of acetic acid. In aspects, the fatty acid is palmitic acid. In certain alternative aspects, the fatty acid is a derivative of palmitic acid.

According to certain aspects wherein the alkyl or heteroalkyl group previously described is a linear alkyl or heteroalkyl compound, the heteroalkyl group can further comprise one or more (e.g., 1-20, 5-20, 10-20, 15-20, 1-15, 1-10, or 1-5) —C═O or $NH_2$ derivative groups bound to the group's backbone. In certain alternative aspects wherein the alkyl or heteroalkyl group previously described is a linear alkyl or heteroalkyl compound, in some aspects, the group comprises no —C═O groups. According to some facets, the group comprises at least two —$NH_2$ groups bound to the backbone, such as at least two, at least three, or sometimes more. In some further aspects, the backbone of the group is a heteroalkyl structure comprising at least one (e.g., at least one, at least two, or at least three, or sometimes more) nitrogen(s), at least one (e.g., at least one, at least two, or at least three, or sometimes more) thiol/sulfur(s), or both. In some facets, at least ~80%, at least ~85%, at least ~90% of the atoms of the backbone are carbons. For example, in some facets at least ~90%, or at least ~95%, or in some cases all the atoms of the backbone are carbons. According to some facets, the backbone comprises or is bound to an optionally derivatized 3-9-membered cycloalkyl, heterocycloalkyl, or heteroaryl ring, such as for example a 3-8 membered, 3-7 membered, or a 3-6 membered ring. In aspects, the ring can comprise one or more nitro groups, is bound to one or more nitro groups, or is bound to one or more side chains bound to one or more nitro groups, such as at least one, at least two, at least three, or sometimes more nitro groups. According to some facets, the group comprises a single (e.g., only one) ring. Examples of heterocyclic/heteroaryl rings that can be R groups or that can be bound to a group, such as an optionally substituted alkyl group (or be encompassed in such a group), include, e.g.,

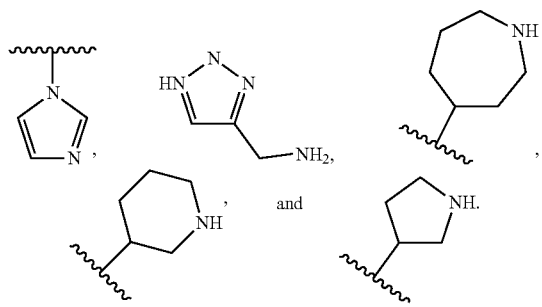

Other, similar derivatizing groups are described in the references cited here, which are incorporated by reference.

According to some aspects, the compounds described herein are tobramycin derivatives according to Formula I, Formula II, or Formula III. Thus, the term "compound" for example as used in the description of the compound of Formula I, is intended to encompass any and all acceptable tobramycin derivatives or compounds resulting from the derivatization of the compound of Formula I by the substitution of the —OH or —NH$_2$ group or a part thereof, e.g., a hydrogen thereof, with an alternative derivatizing/derivative group. In one aspect, at least one derivatizing group will be an optionally substituted/derivatized 2-20 atom backbone alkyl or heteroalkyl group as previously discussed. Such derivatizing groups will include those groups that are pharmaceutically acceptable and ophthalmologically safe and the resulting derivatized molecule will demonstrate sufficient stability to allow for formulation and delivery, which can be determined by application of routine experimentation given the guidance provided herein. Typically, the derivatizing agents also will at least substantially maintain the antimicrobial characteristics of the tobramycin molecule. In aspects the derivatizing group is amphoteric, lipophilic, or both amphoteric and lipophilic. In aspects, one or more derivatizing groups confer a detectable enhancement in trans-corneal penetration, uptake, or retention characteristics as compared to tobramycin.

In such aspects, a tobramycin derivative can exhibit detectably faster, such as for example at least 2 hours faster, at least 4 hours faster, at least 6 hours faster, at least 8 hours faster, at least 12 hours faster, at least 16 hours faster, at least 20 hours faster, or, for example at least 24 hours faster, penetration (e.g., permeation) of corneal cells than tobramycin, detectably better retention/uptake (in amount of API taken up by such cells) in corneal cells than tobramycin, or both. In certain aspects, a derivatizing/derivative group can have a more lipophilic nature than tobramycin. In certain aspects, the derivatizing/derivative group has a more lipophilic logP than tobramycin (e.g., a logP that is at least ~10%, at least ~25%, or at least ~33% greater than tobramycin). In certain aspects, a derivatized tobramycin compound has a more lipophilic nature than tobramycin and, accordingly, has a more lipophilic logP than tobramycin. In aspects, a derivatized tobramycin compound can have a lipophilicity similar (e.g., functionally equivalent) to that of tobramycin and hence a similar logP.

Tobramycin derivatives and derivatizing groups have been described in the prior art as exemplified in, for example, International Patent Publication WO 2010/132760 (by Dozzo, herein referred to as "Dozzo '760"); Fosso M Y et al, in "Differential Effects of Linkers on the Activity of Amphiphilic Tobramycin Antifungals" (Molecules. 2018; 23(4):899. Published 2018 Apr. 13. doi:10.3390/molecules23040899); and Fair in the publication titled, "Singly Modified Amikacin and Tobramycin Derivatives Show Increased rRNA A-site Binding and Higher Potency against Resistant Bacteria" (ChemMedChem. 2014 September; 9(9): 2164-2171. doi:10.1002/cmdc.201402175), and in, for example, the issued US patent U.S. Pat. No. 3,872,072 to Naito. Such compounds or compounds comprising such derivatizing groups can exhibit characteristics desirable for use in the invention described in the present application, such as, for example, the ability to exhibit detectably faster (such as, e.g., at least 2 hours faster, at least 4 hours faster, at least 6 hours faster, at least 8 hours faster, at least 12 hours faster, at least 16 hours faster, at least 20 hours faster, or, e.g., at least 24 hours faster) penetration (e.g., permeation) of, and uptake/retention by, corneal cells than tobramycin alone. The provided exemplary art demonstrates that tobramycin derivatives are known. Hence it should be understood that any such pharmaceutically acceptable, ophthalmologically safe, amphoteric, and, in aspects, preferably lipophilic derivatives described therein should be understood as being capable of being incorporated into compositions and methods of the invention described in this disclosure. The prior art does not, however, appear to describe or suggest either the limitation of such broad classes of compounds to those exhibiting the properties described above, complexing such tobramycin derivatives with a complexing agent to improve the permeation or uptake/retention properties of the API, or formulating the compound with/as a liposomal or microsphere formulation to achieve such results, or using any of the above in the particular amounts described herein (e.g., amounts that are significantly less than, such as at least ~20%, at least ~25%, at least ~33%, or at least ~50% less or more than the amounts of tobramycin used in on-market formulations, such as TOBREX®).

In certain aspects, any one or more substitutions at any one or more locations described above detectably or significantly enhance, e.g., measurably improves, such as for example statistically significantly increases, the ability of the compound to permeate the cornea or corneal cells, be retained/taken up by the cornea or corneal cells, or both permeate and be retained/taken up by the cornea or corneal cells. Such improvements are described in more detail below. In certain facets, the derivatizing groups are functional groups such that they enhance the permeation, retention, and/or permeation, and retention of the compound. According to aspects, the more R-locations of the structures described (e.g., Formula I) wherein substitutions are present, the more the trans-corneal motility is affected, such as for example when three or more, four or more, five or more, or even six or more R-locations have substitutions, the ability of the compound to permeate the cornea, be retained by the cornea, or both permeate and be retained by the cornea are higher (e.g., exhibit higher availability) than compounds in which a single, or for example only two R-positions comprise substitutions. In certain alternative aspects, derivatization does not enhance the trans-corneal transport rate or corneal retention. That is, the derivatized molecule has substantially the same mobility about the cornea as a non-derivatized molecule. In embodiments, there is a limit to the number of substitutions which confer a motility and hence an availability benefit, such that, for example, the molecule can reach a state at which no additional substitutions confer a motility or retention benefit or can, in aspects, retard the permeation and/or retention of the compound.

In certain aspects, the concentration of the active derivatized compound (or in aspects tobramycin) within a formulation can be between ~0.1-~10% w/v, such as for example between ~0.1-~8% w/v, between ~0.1-6% w/v, between ~0.1-5% w/v, or between ~0.1-2.5% w/v, such as for example between ~0.3-10% w/v, between ~0.3-8% w/v, between ~0.3-6% w/v, or for example between ~0.3-5% w/v, such as for example between ~0.1-0.3% w/v, or for example between ~0.6-10% w/v, between ~0.6-8% w/v, between ~0.6-6% w/v, or for example between ~0.6-5% w/v, as in between approximately 1-10% w/v, 1-8% w/v, 1-6% w/v, 1-4% w/v, or 1-3% w/v, for example approximately 2.5% w/v. Such amounts can also apply to tobramycin compositions of the invention that are complexed with a complexing agent or formulated in functional formulation, such as a liposome or microsphere formulation that enhances the corneal cell permeability or uptake of tobramycin in a similar manner to complexes of the invention.

In aspects, a derivatized compound or tobramycin in a tobramycin complex or functional formulation as described herein can be present in a formulation at a concentration which is at least twice the concentration of the API in TOBREX®, e.g., at least ~3 times, ~4 times, ~5 times, ~6 times, ~7 times, ~8 times, ~9 times, or at least ~10 times the concentration of the API in TOBREX®.

In aspects, derivatization of the compounds of the invention increases the rate of cornea cell penetration of the compound. According to certain aspects, the rate of cornea cell penetration of a derivatized compound of the invention can be detectably faster, such as for example at least ~2 hours faster, at least ~4 hours faster, at least ~6 hours faster, at least ~8 hours faster, at least ~12 hours faster, at least ~16 hours faster, at least ~20 hours faster, or, for example at least ~24 hours faster, than that of tobramycin such that the amount of compound in the cornea can be increased by at least ~15%, such as at least ~10%, at least ~12%, at least ~15%, at least ~17%, at least ~20%, at least ~22%, or for example at least ~25% or more after a period of 360 minutes from administration of a similar composition comprising tobramycin.

In aspects, the concentration of a derivatized compound described herein that permeates the surface of the cornea can be at least ~12%, at least ~15%, at least ~17% greater, such as at least ~20% greater, such as at least ~25% greater, as in at least ~30% greater, at least ~35% greater, at least ~40% greater, as in for example at least ~45% greater or more than tobramycin when measured at 360 minutes of an industry standard corneal permeability assay (e.g., the assay exemplified in the Examples below).

According to certain aspects, the level of retention within the cornea of a derivatized compound of the invention described herein can be retained after 6 hours from administration when measured at 360 minutes as measured by a standard corneal retention assay.

According to some facets, a derivatized compound of the invention described herein can be retained in at least ~15% or greater, such as at least ~12%, at least ~15%, at least ~17%, at least ~20%, at least ~22%, or at least ~25% amount in corneal cells after 15 minutes than a corresponding amount of the API in TOBREX®. In certain aspects, the retention of the compound within the cornea as measured by a standard corneal retention assay can be at least ~15% higher, such as at least ~12%, at least ~15%, at least ~17% higher, for example at least ~20% higher, at least ~25% higher, at least ~30% higher, or at least ~32% higher than the retention of tobramycin.

Tobramycin Compound Complexes

Another aspect of the invention relates to a composition comprising a complex formed by a complexing agent and a tobramycin compound (which is either tobramycin or a tobramycin derivative). In aspects, the complexing agent has an amphoteric nature, a lipophilic nature, or both an amphoteric and lipophilic nature. In certain facets, the delivery agents have both a lipophilic and amphiphilic nature and the resulting complex molecule also has a measurably increased lipophilic nature as compared to the API alone. In aspects, the complexing agent is capable of forming a stable complex with the tobramycin compound. In aspects, the complexing agent does not significantly impair the antibiotic properties of the tobramycin compound, does not impair the stability of the tobramycin compound, and is ophthalmologically suitable.

The complexing agent detectably improves, in aspects, the ability of the complex to permeate corneal cells, be taken up by/retained by corneal cells, or both, as compared to the API alone.

In some facets, the complexing agent can significantly facilitate the reduction of dosing frequency without a significant reduction in efficacy, improve the tolerability, improve patient compliance, reduce treatment duration, increase overall treatment efficacy of the pharmaceutically active compound, such as, for example, in the treatment of external infections of the eye and its adnexa caused by susceptible bacteria, or achieve a combination of any or all such effects.

As used herein, the term "complex" is intended to describe molecules or compounds which are chemically associated with one another but typically are not bound together by a covalent bond. For example, a complex can comprise two molecules or compounds which are bound through ionic bonding, hydrogen bonding, or other suitable types of association that allow the complex to stably remain associated and to act as a combined molecule (at least generally) in the context of a composition or method described in this disclosure. In aspects, a tobramycin derivative comprising any parts of the complexes described herein also can be covalently bound, and such covalently bound tobramycin derivative can also be incorporated in a composition of the invention or used in an invention.

According to aspects, tobramycin compounds can be complexed to a complexing agent which is a heterocyclic compound comprising at least one five-to-seven-member nitrogenous ring comprising an attached chain of at least three carbons and at least one carboxylic acid group. In aspects, the complexing agent can be an amino acid, such as for example tryptophan, histidine, or proline. According to aspects, the complexing agent is histidine. In aspects, the complexing agent can be an ophthalmologically acceptable derivative of histidine.

Exemplary histidine derivatives suitable for use in the invention herein can be found in, for example, European patent application EP131631A1 (Tanikawa) describing histidine derivatives anserine and carnosine, or in, e.g., the article, "Ophthalmic Pharmacology of N-acetylcarnosine Lubricant Eye Drops" by Babizhayev (Mark A. Babizhayev, 2006. Ophthalmic Pharmacology of N-acetylcarnosine Lubricant Eye Drops. Journal of Pharmacology and Toxicology, 1: 201-233.) The Babizhayev publication describes histidine derivatives N-acetylcarnosine and L-carnosine. It is expected that at least some of these or other histidine derivatives known in the art will exhibit properties of a complexing agent in terms of pharmaceutical acceptability, ophthalmological safety, amphoteric properties, or lipophilicity, or also the ability to DOS enhance the permeation and/or uptake/retention of the complex by corneal cells as compared to the active pharmaceutical ingredient (API) alone.

In certain alternative aspects, the complexing agent is an ophthalmologically safe copolymer. In aspects the ophthalmologically safe copolymer can be any copolymer which comprises one or more characteristics described above for a suitable complexing agent for use in the invention. In aspects, the complexing agent is Polyvinyl caprolactam-polyvinyl acetate-polyethylene glycol graft co-polymer (PCL-PVAc-PEG).

PCL-PVAc-PEG (structure provided below) originates, interestingly, from the need of formulators for a means of preparing solid solutions of poorly water-soluble drugs. The BASF polymer Soluplus® is a PCL-PVAc-PEG comprising significant amphiphilic properties and is one example well suited for use in the invention herein. The structure of such a compound is exemplified here:

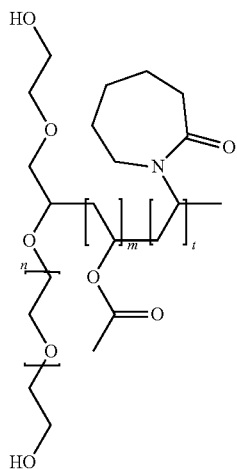

Polyvinyl Caprolactam-Polyvinyl
Acetate-Polyethylene Glycol Graft Co-Polymer

According to aspects, the complexing agent is a derivative of PCL-PVAc-PEG. Such derivatives can be any derivative and can comprise one or more characteristics desirable and suitable for incorporation into the compositions and formulations described herein, such as for example, pharmaceutical acceptability, ophthalmological safety, amphiphilicity, lipophilicity, and, in some aspects, the ability to enhance the ability of an associated compound to be permeate and/or be retained by the cornea.

In certain aspects, the concentration of the active compound within a formulation can be between ~0.1-~10% w/v, such as e.g., between ~0.1-~8% w/v, between ~0.1-6% w/v, between ~0.1-5% w/v, or between ~0.1-2.5% w/v, such as, e.g., between ~0.3-10% w/v, between ~0.3-8% w/v, between ~0.3-6% w/v, or, e.g., between ~0.3-5% w/v, such as, for example, between ~0.1-0.3% w/v, or, e.g., between ~0.6-10% w/v, between ~0.6-8% w/v, between ~0.6-6% w/v, or, e.g., between ~0.6-5% w/v, as in between about 1-10% w/v, 1-8% w/v, 1-6% w/v, 1-4% w/v, or 1-3% w/v, for example ~2.5% w/v.

In certain aspects, the concentration of the complexing agent within a formulation can be between ~0.1-~10% w/v., such as for example between ~0.1-~8% w/v, between ~0.1-6% w/v, between ~0.1-5% w/v, or between ~0.1-2.5% w/v, such as, e.g., between ~0.3-10% w/v, between ~0.3-8% w/v, between ~0.3-6% w/v, or for example between ~0.3-5% w/v, such as for example between ~0.1-0.3% w/v, or for example between ~0.6-10% w/v, between ~0.6-8% w/v, between ~0.6-6% w/v, or, e.g., between ~0.6-5% w/v, as in between approximately 1-10% w/v, between approximately 1-8% w/v, between approximately 1-6% w/v, between approximately 1-4% w/v, or between approximately 1-3% w/v, for example approximately 2.5% w/v.

In some facets, the ratio of complexing agent to API is also ~0.5:1 to ~2:1 by weight or w/v, such as ~0.75:1 to ~1.25:1 w/v, such as ~0.9:1 to ~1.1:1 w/v or ~1:1 w/v.

In aspects, a complexed compound can be present in a formulation at a concentration which is at least twice the concentration of the API in TOBREX®, for example 3 times, at last four times, times, at least six times, at least seven times, at least eight times, at least nine times, or at least ten times the concentration of the API in TOBREX®.

Figure 5:
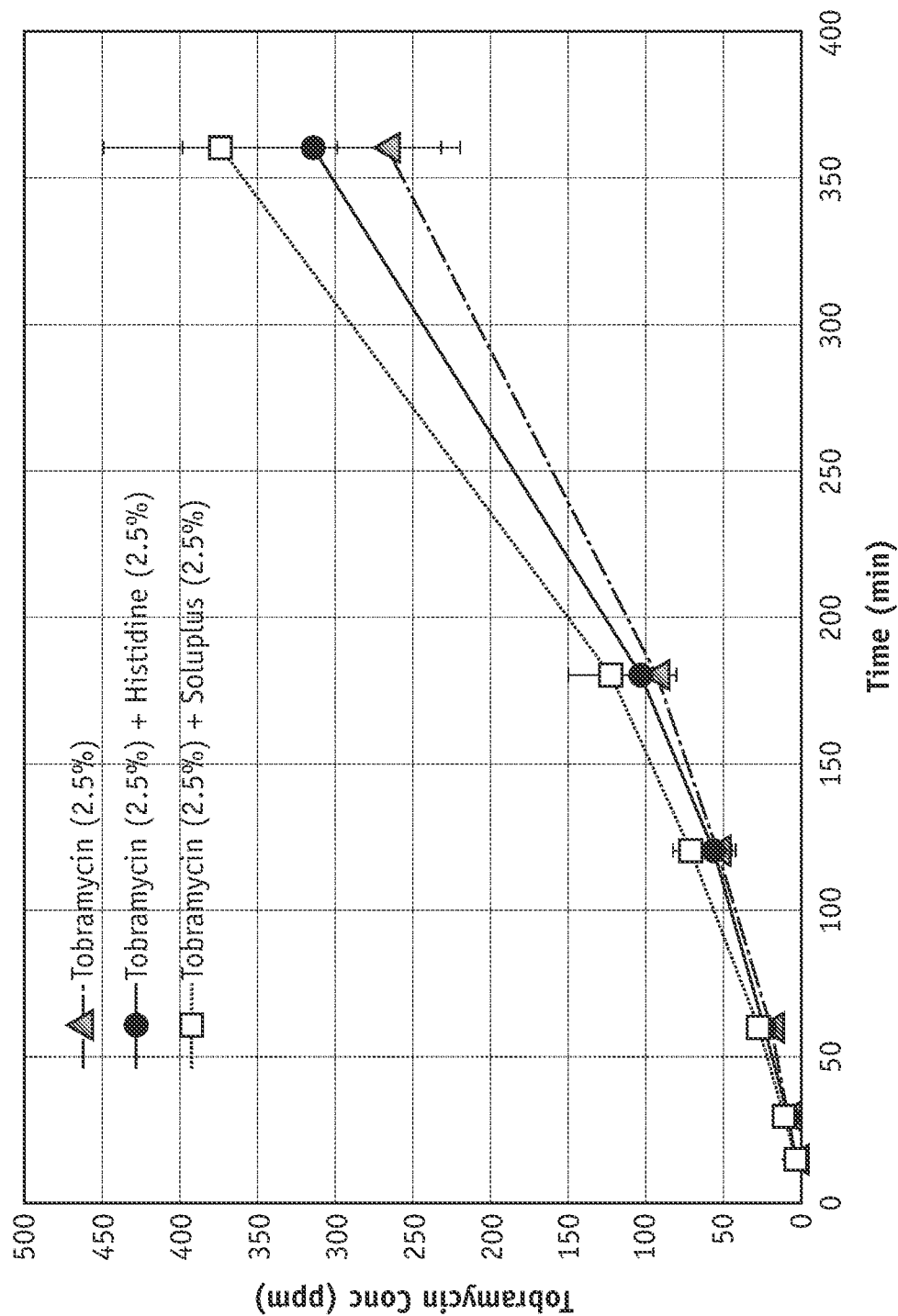
FIG. 5 is a graph showing the corneal permeability of tobramycin, tobramycin+histidine complex solution and tobramycin+Soluplus® complex solution.

According to some aspects, a compound as described herein, whether derivatized (e.g., having one or more modifications to an R-group as previously described) or non-derivatized (e.g., having no modifications to an R— group as previously described), complexed with a complexing agent, or formulated in a functional formulation of the invention, can have a rate of cornea cell permeation that is detectably faster, such as for example at least ~two hours faster, at least ~four hours faster, at least ~six hours faster, at least ~eight hours faster, at least ~12 hours faster, at least ~16 hours faster, at least ~20 hours faster, or, for example at least ~24 hours faster, than the corresponding unmodified/non-complexed compound or formulation. In another aspect, the amount of compound in corneal cells following administration of such a derivative, complex, or functional formulation exhibits an increase of at least ~15%, such as at least ~10%, at least ~12%, at least ~15%, at least ~17%, at least ~20%, at least ~22%, at least ~25% or more after a period of 60 minutes from administration as respectively compared to an unmodified compound, non-complexed compound, or compound in a non-functional formulation. FIG. 5, for example, illustrates tobramycin-histidine and tobramycin-polyvinyl caprolactam-polyvinyl acetate-polyethylene glycol graft copolymer (Soluplus®) complexes and their experimentally derived permeation rates compared to tobramycin alone. This data is further discussed in the Example section herein.

In certain aspects, the concentration of a complexed compound described herein permeating the surface of the cornea can be at least ~17% greater, such as for example at least ~12% greater, at least ~15% greater, at least ~17% greater, at least ~20% greater, at least ~25% greater, at least ~30% greater, at least ~35% greater, or for example at least ~40% greater or for example at least ~45% greater when in complexed form than in non-complexed form when measured at 360 minutes of an industry standard corneal permeability assay.

In certain aspects, the concentration of a complexed compound permeating the surface of the cornea can be at least ~15% or greater, such as at least ~10%, at least ~12%, at least ~15%, at least ~17%, at least ~20%, at least ~22%, or at least ~25% greater or more after 15 minutes from application than a corresponding amount of the API in TOBREX®.

In certain such aspects, the complexing agent is histidine. In certain alternative aspects, the complexing agent is PCL-PVAc-PEG.

According to certain facets, amount of a complexed compound retained within the cornea after ~6 hours from administration when measured by an industry standard corneal retention assay is detectably or significantly greater than the amount of a noncomplexed counterpart compound. In aspects, the amount of the complex retained is about the same as the amount of the complex compound present in the cornea when the compound is administered.

In aspects, the retention of a complexed compound of the invention described herein within the cornea can be at least ~15% higher, such as at least ~10%, at least ~12%, at least ~15%, at least ~17%, at least ~20%, at least ~22%, or at least ~25% greater or more, such as at least ~30% higher than the retention of the non-complexed compound when measured at 360 minutes as measured by standard corneal retention assay.

According to some aspects, a complexed compound of the invention can be retained in at least ~15% or greater, such as such as at least ~10%, at least ~12%, at least ~15%, at least ~17%, at least ~20%, at least ~22%, or at least ~25% greater or more, amount in corneal cells after 15 minutes than a corresponding amount of the API in TOBREX®.

Figure 6:
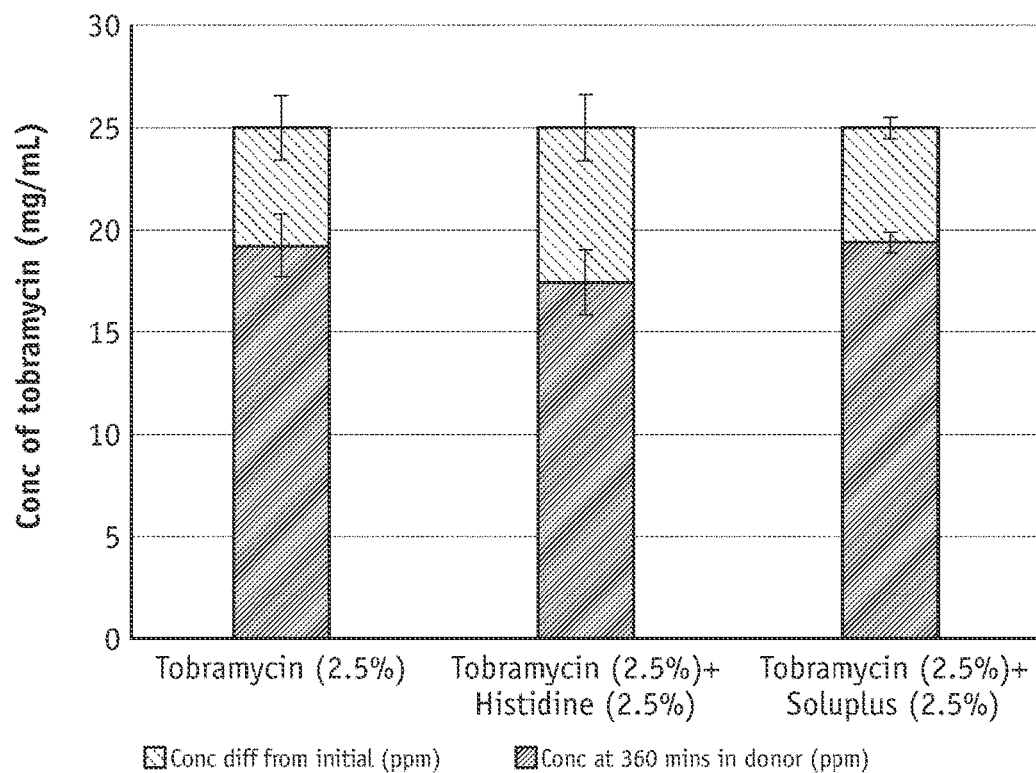
FIG. 6 is a plot showing the depletion rate of tobramycin, a tobramycin+histidine complex solution, and a tobramycin+Soluplus® complex solution, in each applicable donor chamber, in a depletion assay.

In some such aspects, the complexing agent is histidine. FIG. 6 illustrates the experimentally derived retention rates of tobramycin-histidine and tobramycin-polyvinyl caprolactam-polyvinyl acetate-polyethylene glycol graft copolymer complexes compared to tobramycin alone. This data is further discussed in the Example section included herein.

In certain aspects, both the concentration of a compound of the invention permeating the surface of the cornea can be at least about 17% greater, such as for example at least ~10%, at least ~12%, at least ~15%, at least ~17%, at least ~20%, at least ~22%, or at least ~25% greater or more when in complexed form than in non-complexed form when measured at 360 minutes of an industry standard corneal permeability assay, and the retention of the complexed compound within the cornea as measured by a standard corneal retention assay can be at least ~25% higher, such as at least ~10% higher, at least ~15% higher, at least ~20% higher, or at least ~30% higher or at least ~35% higher than the retention of the compound in non-complexed form. In certain aspects, a complexing agent capable of achieving such a result is, for example, but may not be limited to, a heterocyclic compound comprising at least one 5 to 7-member nitrogenous ring comprising an attached chain of at least 3 carbons and at least one carboxylic acid group, such as, for example, an amino acid, e.g., histidine.

Process for Preparing Complexes

According to aspects, complexes discussed herein can be manufactured for use in larger formulations, e.g., in a solution for administration to the eye. To form complexes, illustrated here as, e.g., tobramycin-histidine, solutions according to Tables 1 and 2, below, or similar formulations, can be made.

TABLE 1

Tobramycin complexed with histidine.

| Sr. No | Ingredient | Percentage (w/v) |
|---|---|---|
| 1 | Tobramycin | 1.0-10% |
| 2 | Histidine | 1.0-10% |
| 3 | Water | q.s. |

An exemplary manufacturing process for preparing such compositions is as follows: an amount representing approximately 1-10% of the total batch volume of tobramycin, and an amount representing approximately 1-10% of the total batch volume of histidine are weighed. For example, if a 100 mL batch of 2.5% tobramycin-histidine complex solution is desired, 2.5 mg of tobramycin and 2.5 mg of histidine are each weighed. The weighed quantities of each tobramycin and histidine are then dissolved in a quantity of water less than the total target batch volume. For example, if a 100 mL batch is being prepared, the weighed tobramycin and histidine can be dissolved in, for example, approximately 90 mL of water. The solution is then brought up to the final target volume with water. The solution can then be allowed to dry such that the solution becomes a dry powder. This can be accomplished by any means; in small batch sizes, pouring a small amount of the solution in a series of petri dishes can accomplish this quickly. The Examples provided within this disclosure demonstrate the efficacy of such a process to form such complexes.

The same process can be followed when preparing, as another example, tobramycin-polyvinyl caprolactam-polyvinyl acetate-polyethylene glycol graft copolymer complexes. Here, the BASF product Soluplus® is used as the polyvinyl caprolactam-polyvinyl acetate-polyethylene glycol graft copolymer.

TABLE 2

Tobramycin complexed with Soluplus ®.

| Sr. No | Ingredient | Percentage (w/v) |
|---|---|---|
| 1 | Tobramycin | 1.0-10% |
| 2 | Polyvinyl caprolactam-polyvinyl acetate-polyethylene glycol graft copolymer (Soluplus ®) | 1.0-10% |
| 3 | Water | q.s. |

An amount representing approximately 1-10% of the total batch volume of tobramycin and an amount representing approximately 1-10% of the total batch volume of polyvinyl caprolactam-polyvinyl acetate-polyethylene glycol graft copolymer (Soluplus®) are weighed. For example, if a 100 mL batch of 2.5% tobramycin-polyvinyl caprolactam-polyvinyl acetate-polyethylene glycol graft copolymer (Soluplus®) complex solution is desired, 2.5 mg of tobramycin and 2.5 mg of polyvinyl caprolactam-polyvinyl acetate-polyethylene glycol graft copolymer (Soluplus®) are each weighed. The weighed quantities of each tobramycin and polyvinyl caprolactam-polyvinyl acetate-polyethylene glycol graft copolymer (Soluplus®) are then dissolved in a quantity of water less than the total target batch volume. For example, if a 100 mL batch is being prepared, the weighed tobramycin and polyvinyl caprolactam-polyvinyl acetate-polyethylene glycol graft copolymer (Soluplus®) can be dissolved in, for example, approximately 90 mL of water. The solution is then brought up to the final target volume with water. The solution can then be allowed to dry such that the solution becomes a dry powder. This can be accomplished by any means known or standard in the art; in small batch sizes, pouring a small amount of the solution in a series of petri dishes can accomplish this quickly. The Examples provided below demonstrate the efficacy of such a process to form such complexes.

According to certain aspects, when utilizing the complex powder to prepare a final formulation, such a final formulation can be sterilized using any one or more of the methods selected from heat sterilization, gaseous sterilization, filtration sterilization or radiation sterilization. In common facets, such sterilization means do not detectably or significantly affect the potency or stability of some, most, or all the compounds of the invention described herein.

Functional Formulations

In certain aspects, other delivery agents that generate a functional formulation can be used in place of or in addition to complexing agents. A "functional formulation" in this disclosure means a formulation of a tobramycin compound (tobramycin or a tobramycin derivative) and one or more formulating agents, other than a complexing agent, that results in a formulation that exhibits detectably or significantly enhanced permeation of corneal cells, detectably or significantly enhanced uptake of API, detectably or significantly enhanced retention of API by corneal cells, or both, and that is ophthalmologically safe and does not significantly deter from the API's antibiotic properties. The formulating agent can be, and the overall formulation can be, more lipophilic than tobramycin. In one aspect, the formulating agent comprises a liposome having such properties or a microsphere having such properties. Out of the numerous types of ophthalmologic formulations available, such formulations can in aspects be particularly capable of exhibiting such properties.

In one aspect, the functional formulation is a liposome formulation. In aspects, the liposomes comprise one or more of phosphatidylcholine (PC), cholesterol and one or more of a lipid-conjugated hydrophilic polymer(s). In aspects, such polymers comprise bioadhesive and/or trans-corneal permeation-enhancing characteristics. In aspects, liposomes used in the invention are small unilamellar vesicles (SUVs), comprising a single layer of lipid such as lecithin or phosphatidylglycerol encapsulating aqueous interior core. In alternative aspects, the liposomes used in the invention are multilamellar vesicles (MLVs), comprising various layers of lipid bilayers. In specific aspects, the present liposomes can be small unilamellar vesicles (SUVs), giant unilamellar vesicles (GUVs), and large unilamellar vesicles (LUVs), or any combination thereof.

As exemplified in the 2011 Mishra review publication "Recent Applications of Liposomes in Ophthalmic Drug Delivery" (J Drug Deliv.; 2011: 863734), wherein the characteristics of liposomes and the properties which make them suitable for ophthalmological delivery are well described, among other publications and patents, multiple liposomal formulations have been investigated and subjects of publication, hence are well known in the art. In aspects, any such liposomes can comprise suitable characteristics for use in the invention including one or more of an amphoteric nature, a lipophilic nature, non-interference with the stability of the compound with which they may be present in composition or formulation, non-interference with the functionality of the active, such as for example, the antimicrobial activity of the accompanying compound(s). In addition, such liposomes can detectably enhance the ability of the compounds of the invention to permeate, be retained by, or both permeate and be retained by the cornea. Accordingly, such liposomes should be understood to be suitable for the inclusion within the invention described herein and are hereby incorporated by reference.

In another aspect, the functional formulation is a microparticle formulation, such as a nano- or microparticle formulation. In aspects, the functional formulation is a nanoparticle formulation that is adapted so that an effective amount of the administered nanoparticles is not washed out of the eye during or following application. In aspects, microparticles or nanoparticles of a formulation comprise, primarily are, generally are (i.e., generally consist of), substantially are, or entirely are (i.e., consist of) charged microparticles or nanoparticles. In aspects, nanoparticles of a nanoparticle formulation, comprise, primarily comprise, generally consist of, substantially consist of, or consist of positively charged nanoparticles. In aspects, charged nanoparticles or microparticles of a formulation exhibit DOS improved affinity for the cornea than uncharged counterpart particles. In aspects, microparticles or nanoparticles of a functional formulation primarily comprise, generally are, substantially are, or consist of uncharged particles. For example, in an aspect a microparticle formulation is provided that primarily comprises, generally consists of, substantially consists of, or consists of uncharged microparticles.

In facets, a functional formulation is a microparticle formulation, e.g., in the form of microspheres (e.g., is a composition at least primarily comprising, generally consisting of, substantially consisting of particles of substantially spherical shape).

In one aspect, a formulation comprises microparticles above one micrometer in size, such as for example between ~one micrometer-~15 micrometers, such as between ~two-~15 micrometers, such as between ~four-~15 micrometers, such as between ~six-~15 micrometers, such as between ~eight-~15 micrometers, as in between ~10-~15 micrometers, or for example between ~one-~12 micrometers, between ~one-~10 micrometers, between ~one-~eight micrometers, or for example between ~one and ~six micrometers. In one aspect, the microparticles comprise, generally consist of, or consist of monolithic particles possessing a porous or a solid polymer matrix.

In certain aspects, compounds of the invention can be present in the core of microspheres in liquid form. In certain aspects, the compounds of the invention can be present in the core of microspheres in solid form. In alternative aspects, the compounds described herein can be adsorbed onto the surface of a microsphere. According to certain aspects, the particle size of the microspheres utilized herein do not exceed ~10 micrometers (such as for example no more than ~10 micrometers in average size in any single direction) so as to avoid ocular irritation which can occur in microsphere formulations comprising microspheres of larger size.

Functional formulations as described above or elsewhere herein can be a component of a larger formulation designed for pharmaceutical use in treating, for example, an external infection of the eye or its adnexa. In certain aspects, the formulation can comprise tobramycin and one or more amphophilic and optionally also lipophilic formulating agents. In certain facets, the formulating agent comprises liposomes. In certain alternative aspects, the formulation agent comprises microspheres. In certain aspects, both liposomes and microspheres can be present. In aspects, the presence of the liposomes, microspheres, or both liposomes and microspheres detectably enhances the permeation of, retention by, or both permeation of and retention by the cornea (e.g., corneal cells) of the tobramycin over a similar formulation comprising tobramycin without liposomes or microspheres. In aspects, the tobramycin can be present in the formulation in a concentration of between ~0.1-~10% by weight.

In certain aspects, a formulation for pharmaceutical use in treating, for example, an external infection of the eye or its adnexa can comprise a derivative of tobramycin and one or more amphophilic and optionally also lipophilic formulating agents. In certain facets, the formulating agent comprises liposomes. In certain alternative aspects, the formulation agent comprises microspheres. In certain aspects, both liposomes and microspheres can be present. In aspects, the presence of the liposomes, microspheres, or both liposomes and microspheres detectably enhance the permeation of, retention by, or both permeation of and retention by the cornea or corneal cells, of the tobramycin, over that of (compared to) a similar formulation comprising derivatized tobramycin alone or (formulations not comprising liposomes or microspheres). In aspects, tobramycin can be present in a formulation in a concentration of between ~0.1-~10% by weight.

According to certain aspects, a formulation for pharmaceutical use in treating, for example, an external infection of the eye or its adnexa, can comprise tobramycin or a tobramycin derivative complexed with a complexing agent and one or more amphophilic and optionally also lipophilic formulating agents. In certain facets, the formulating agent comprises liposomes. In certain alternative aspects, the formulation agent comprises microspheres. In certain aspects, both liposomes and microspheres can be present. In aspects, the presence of the liposomes, microspheres, or both liposomes and microspheres detectably or significantly enhance the permeation of, retention by, or both permeation of and retention by the cornea (e.g., corneal cells) of the tobramycin or tobramycin derivative over that of a similar formulation comprising non-complexed tobramycin or non-complexed derivatized tobramycin. In aspects, the tobramycin compound can be present in the formulation in a concentration of between ~0.1-~10% by weight (e.g., ~0.1-0.2% by weight or w/v, ~0.1-0.3% w/v, ~0.05%-0.25% w/v, ~0.6-6% w/v, ~0.9-3.6% w/v, or ~1-7.5% or 1-5% w/v). In aspects, the complexing agent can be present in the formulation in a concentration of between ~0.1-~10% by weight or in any of the other referenced amounts that the tobramycin compound can be present in, +/-~15%, ~10%, or ~5%.

Antimicrobial Activity of Compound/Compositions

Compositions of this invention (compositions comprising tobramycin derivatives, tobramycin compound complexes, and functional formulations of tobramycin compounds described herein) exhibit anti-bacterial properties and, accordingly, are useful as antibiotics.

In certain aspects, the compounds of the invention demonstrate antibiotic activity against one or more, in some aspects against several, gram-negative and/or gram-positive ophthalmic pathogens. In certain aspects, the compounds demonstrate strong activity against certain microorganisms, such as specifically for example *Staphylococcus aureus* and *Staphylococcus epidermidis* (e.g., both coagulase positive and coagulase negative *S. epidermidis*). In certain aspects, the compounds of the invention are active against some Streptococci, including some of the Group A -beta-hemolytic species, some nonhemolytic species, and some *Streptococcus pneumoniae* species. In certain facets, the compounds of the invention can demonstrate antibiotic activity against such microorganisms as, but not limited to, *Pseudomonas aeruginosa, Escherichia coli, Klebsiella pneumoniae, Enterobacter aerogenes, Proteus mirabillis, Morganella morganii*, most *Proteus vulgaris* strains, *Haemophilus influenzae* and *H. aegyptius, Moraxella lacunata, Acinetobacter calcoaceticus*, and some *Neisseria* species. In certain aspects, the compounds of the invention can demonstrate antimicrobial activity against penicillin-resistant strains of Staphylococci and also antimicrobial activity against microorganisms resistant to gentamicin.

In aspects, formulations comprising tobramycin and at least one complexing agent, at least one functional agent (such as liposomes or microspheres, or both, which enhance permeability or retention), at least one complexing agent, and also comprising a derivatized tobramycin demonstrate detectably (measurably) or significantly improved antimicrobial activity over a similar formulation comprising tobramycin alone (e.g., over that of TOBREX®). E.g., such formulations can in some aspects demonstrate a measurably greater ability (e.g., detectably or significantly greater ability) to inhibit bacterial growth as determined by one or more standard microbial inhibition assays such as, for example, the Kirby Bauer test.

Stability and Storage

According to certain aspects, the compounds described herein are chemically stable and suitable for pharmaceutical formulation, e.g., stability is supportive for use in traditional modes and methods of administration and traditionally accepted administration schedules.

According to some aspects of the invention, the compounds, compositions, and formulations disclosed herein are stable for extended periods of time when stored under standard conditions for pharmaceutical actives and, more specifically, for antibiotics in general. The compounds, compositions, and formulations disclosed herein should in aspects generally be stored at between about 2-25° C. (about 36-77° F.) and in aspects should generally be maintained in a safe environment in closed and/or sealed packaging so as to prevent contamination and/or non-prescribed use.

In some specific aspects, the compounds and compound complexes described herein retain at least 90% w/w, such as for example at least ~80%, at least ~85%, at least ~90%, at least ~92%, at least ~94%, at least ~96%, at least ~98%, or at least ~99% of the potency of the compound active when stored at 25° C. and about 60% relative humidity, or also when stored at 40° C. and 75% relative humidity for 3 months.

In specific embodiments, a formulation comprising a tobramycin-histidine complex, or also a tobramycin-polyvinyl caprolactam-polyvinyl acetate-polyethylene glycol graft copolymer complex can in some aspects maintain at least about 90% w/w, such as for example at least ~80%, at least ~85%, at least ~90%, at least ~92%, at least ~94%, at least ~96%, at least ~98%, at least ~99% of the potency of tobramycin when stored at 25° C. and about 60% relative humidity, or also when stored at 40° C. and 75% relative humidity for 3 months.

Pharmaceutical Formulations

In certain aspects, compositions described herein can be co-administered with one or more other agents (e.g., agents alone, agents within a composition, agents within a formulation, or any combination thereof). As used, herein, compositions of the invention "co-administered" with one or more other actives means the compositions herein are provided separately from such one or more other agents, such as, e.g., the one or more other agents are provided in an administration form separate from the compositions herein. "Co-administration" can mean two or more agents, compositions, or formulations administered at the same time as one another, e.g., the two or more agents, compositions, or formulations are administered together on the same administration schedule (e.g., three times per day, two times per day, or once per day), or also or alternatively "co-administration" can mean two or more agents, compositions, or formulations administered during the same course of treatment, e.g., the two or more agents, compositions, or formulations are administered to a recipient at the same or different times during a single time period, such as over the course of one day, one week, or one month.

In aspects, such a one or more other agents co-administered with the compositions herein can be any agent which addresses the primary indication target of the compositions herein, e.g., a microbial infection such as a bacterial infection of a mammalian eye or its adnexa, or one or more conditions related to the primary indication, such as, e.g., inflammation (or, e.g., itching, redness, or other exemplary conditions which can accompany an ocular microbial infection). In aspects, a co-administered agent can be any agent described as a second active described herein. In aspects, a co-administered agent can be an antimicrobial agent, e.g., an antibiotic agent. In aspects, a co-administered agent can comprise a compound according to Formula I, Formula II, or Formula III herein. In aspects, a co-administered agent can be an anti-inflammatory agent, such as an NSAID or a steroid, including any anti-inflammatory agent described herein. In aspects, such an anti-inflammatory agent can be a dexamethasone compound.

In aspects, compositions described herein can be combined with one or more other ingredients to form ophthalmologically suitable (e.g., ophthalmologically useful) formulations, e.g., single formulations, for administration to a mammalian eye. In aspects, tobramycin derivatives, tobramycin compound complexes, and functional compositions of tobramycin compounds (including tobramycin compound complexes) can be combined with one or more other ingredients to form ophthalmologically useful formulations for administration to subjects, such as human patients. In general, such formulations can comprise any suitable type of excipient or other agent, which can include in one aspect one or more additional APIs. As various types of formulations will have different properties, however, several groupings of such formulations and types of such formulations can each represent unique aspects of the invention. In aspects, such other excipients or APIs can be characterized as being "associated" with a primary compound, e.g., a complexed compound such as tobramycin or tobramycin derivative of the compositions described herein, in that the one or more other excipients or APIs are present in a formulation with a primary compound described herein. In aspects, an excipient or API associated with a primary compound is delivered within the same administration form, e.g., administered concurrently, with the primary compound.

In aspects, delivery agents that can be associated with a tobramycin derivative or tobramycin compound complex can generally include any pharmaceutically acceptable delivery agent suitable for ophthalmic delivery such as but not limited to specific emulsifiers to form emulsions, viscosity enhancers such as those used to form ointments, suspending agents, aqueous gels, nanomicelles, nanoparticles, dendrimers, implants, contact lenses, nanosuspensions, microneedles, niosomes, liposomes, microspheres, complexed delivery agents, etc.

In aspects, the compounds of the invention are capable of being added to a pharmaceutical formulation for delivery as a therapeutic drug product. In aspects, such a formulation comprises an effective amount of a compound of the invention, whether in derivatized or non-derivatized form, along with a complexing agent. In aspects, one or more additional delivery agents can be present. The delivery agent could be any delivery agent described herein. In aspects, the one or more additional delivery agents can comprise liposomes, microspheres, or both liposomes and microspheres. In certain facets, the one or more additional liposome(s), a microsphere(s), or both, are amphoteric. In aspects, the one or more additional liposome(s), microsphere(s), or both, are lipophilic. In aspects, any present delivery agent is suitable for ophthalmologic applications. In aspects, such formulations provide for the compound to be retained in at least about 15% greater, such as at least ~10%, at least ~12%, at least ~15%, at least ~17%, at least ~20%, at least ~22%, or at least ~25% greater amount in corneal cells after 15 minutes than a corresponding amount of the compound when no additional delivery agent is present.

In aspects, the presence of the one or more additional delivery agents significantly enhances the permeation, retention, or both permeation and retention of the compound across and/or within corneal cells compared to a similar formulation comprising no additional delivery agents.

In facets, the formulations of the invention can comprise one or more excipients. Such possible excipients are described in detail herein; however, in certain aspects of the invention, one or more excipients can be selected from a smaller group comprising one or more of a viscosity-enhancer, osmotic modification agent, surfactant, chelating agent, tonicity agent, buffer, pH-adjusting agent, a preservative, or water. In aspects, a formulation of the invention can comprise at least one viscosity enhancing excipient. In aspects, the viscosity enhancing agent can contribute to the viscosity of the formulation. In certain other aspects, the viscosity enhancing agent may not contribute to the final formulation viscosity but is present to serve an alternative purpose and its viscosity enhancing properties, which may be present in certain formulations, is not present in others. In aspects, the viscosity of a formulation of the invention is between about 10 cps and about 400 cps, such as for example between about 25 cps to about 300 cps. In aspects, the viscosity of a formulation comprising a compound in complex form is at least about 5% higher, such as at least ~1% higher, at least ~2% higher, at least ~3% higher, at least ~4% higher, at least ~5% higher, at least ~6% higher, at least ~7% higher, at least ~8% higher, at least ~9% higher, or at least ~10% higher or more than the viscosity of a similar composition comprising the compound in non-complexed form. In certain aspects, use of a viscosity enhancer can further contribute to the viscosity of the formulation beyond that contributed by the complexing of the compound with the complexing agent, such as for example the presence of a viscosity enhancing agent can increase the viscosity of a composition by at least about 1%, at least ~2%, at least ~3%, at least ~4%, at least ~5%, at least ~6%, at least ~7%, at least ~8%, at least ~9%, or at least ~10% or even higher, such as at least ~15%, at least ~20%, at least ~30%, at least ~40%, at least ~50%, at least ~75%, or even double, triple, or increase the viscosity of a formulation hundreds of times, e.g., 200, 400, 600, or 800 or more times over the viscosity of a similar formulation without a viscosity enhancing agent.

According to certain aspects, a pharmaceutical formulation of the invention can comprise a concentration of a compound described herein in a concentration of between about 0.1-about 10% w/v, such as between ~0.1-~8% w/v, ~0.1-~6% w/v, ~0.1-~4% w/v, ~0.1-~2% w/v, or ~0.1-~1% w/v, such as for example between ~0.3-~5% w/v, 0.3-~4% w/v, ~0.3-~2% w/v, or ~0.3-~1% w/v, as in for example ~0.6-~5% w/v, ~0.6-~4% w/v, ~0.6-~2% w/v, or ~0.6-~1% w/v, such as for example between ~1-~8% w/v, between ~1-~6% w/v, between ~1-~4% w/v, or, e.g., approximately 2.5% w/v.

According to certain aspects, a pharmaceutical formulation of the invention can comprise a concentration of a complexing agent described herein in a concentration of between ~0.1-~10% w/v, such as between ~0.1-~8% w/v, ~0.1-~6% w/v, ~0.1-~4% w/v, ~0.1-~2% w/v, or ~0.1-~1% w/v, such as for example between ~0.3-~5% w/v, 0.3-~4% w/v, ~0.3-~2% w/v, or ~0.3-~1% w/v, as in for example ~0.6-~5% w/v, 0.6-~4% w/v, ~0.6-~2% w/v, or ~0.6-~1% w/v, such as for example between ~1-~8% w/v, between ~1-~6% w/v, between ~1-~4% w/v, or, e.g., approximately 2.5% w/v.

According to certain aspects, tobramycin derivatives, in complexed or non-complexed forms, are combined with one or more delivery agents or other excipients. In certain aspects, the delivery agent can be any delivery agent disclosed herein. In some facets, the delivery agent can be a complexing agent, liposome, or microsphere. In aspects, such formulations provide for the compound to be retained in at least about 15% greater, such as at least ~10%, at least ~12%, at least ~15%, at least ~17%, at least ~20%, at least ~22%, or at least ~25% greater amount in corneal cells after 15 minutes than a corresponding amount of the compound when no additional delivery agent is present.

According to certain aspects, the presence of the one or more delivery agents detectably or significantly enhances the permeation, retention, or both permeation of retention of the compound across and/or within corneal cells compared to a similar formulation comprising no delivery agents. As discussed above, such formulations are considered "functional formulations" herein. Such functional formulations can be, e.g., a liposome formulation or a microsphere formulation. Such a functional formulation can comprise tobramycin, a tobramycin derivative, or a mixture of an effective amount of two or more APIs of either such type, in each case in either complexed or non-complexed form.

In certain aspects, a formulation comprising a derivatized or non-derivatized compound of the invention along with one or more delivery agents further comprises one or more excipients. Such possible excipients are described in detail herein; however, in certain aspects of the invention, one or more excipients can be selected from a smaller group comprising one or more of a viscosity-enhancer, osmotic modification agent, surfactant, chelating agent, tonicity agent, buffer, pH-adjusting agent, a preservative, or water. In certain aspects, a formulation of the invention can comprise at least one viscosity enhancing excipient. In certain aspects, the viscosity enhancing agent can contribute to the viscosity of the formulation. In certain other aspects, the viscosity enhancing agent may not contribute to the final formulation viscosity but is present to serve an alternative purpose and its viscosity enhancing properties, which may be present in certain formulations, is not present in other formulations. In certain aspects, the viscosity of a formulation of the invention is between about 10 cps and about 400 cps, such as for example between about 25 cps to about 300 cps. In aspects, the viscosity of a formulation comprising a derivatized API compound (e.g., a tobramycin derivative) is at least about 5% higher, such as at least about 1% higher, at least about 2% higher, at least about 3% higher, at least about 4% higher, at least about 5% higher, at least about 6% higher, at least about 7% higher, at least about 8% higher, at least about 9% higher or at least about 10% higher or more than the viscosity of a similar composition comprising a non-derivatized API compound (e.g., tobramycin). In certain aspects, the use of a viscosity enhancing excipient further contributes to the viscosity of a final formulation beyond that contributed by the derivatization of the compound, such as for example the presence of a viscosity enhancing agent can increase the viscosity of a composition by at least about 1%, at least ~2%, at least ~3%, at least ~4%, at least ~5%, at least ~6%, at least ~7%, at least ~8%, at least ~9%, or at least ~10% or even higher, such as at least ~15%, at least ~20%, at least ~30%, at least ~40%, at least ~50%, at least ~75%, or even double, triple, or increase the viscosity of a formulation hundreds of times, e.g., ~200, ~400, ~600, or ~800 or more times over the viscosity of a similar formulation without a viscosity enhancing agent.

According to certain aspects, a pharmaceutical formulation of the invention can comprise a concentration of a derivatized compound described herein in a concentration of between about 0.1-about 10% w/v, such as between ~0.1-~8% w/v, ~0.1-~6% w/v, ~0.1-~4% w/v, ~0.1-~2% w/v, or ~0.1-~1% w/v, such as for example between ~0.3-~5% w/v, 0.3-~4% w/v, ~0.3-~2% w/v, or ~0.3-~1% w/v, as in for example ~0.6-~5% w/v, 0.6-~4% w/v, ~0.6-~2% w/v, or ~0.6-~1% w/v, such as for example between ~1-~8% w/v, between ~1-~6% w/v, between ~1-~4% w/v, or for example approximately 2.5% w/v.

In aspects, the one or more additional delivery agents that can be combined with a tobramycin derivative or tobramycin compound complex can comprise liposomes, microspheres, or both liposomes and microspheres, even where such delivery agents do not result in a functional formulation. In certain facets, the one or more additional liposome(s), a microsphere(s), or both, are amphoteric. In certain aspects, the one or more additional liposome(s), microsphere(s), or both, are lipophilic. In aspects, any present delivery agent is suitable for ophthalmologic applications.

In aspects, formulations comprising liposomes, microspheres, or both liposomes and microspheres are functional formulations. Such formulations can provide for the compound to be, e.g., retained/taken up by in at least about 15% greater, such as at least ~10%, at least ~12%, at least ~15%, at least ~17%, at least ~20%, at least ~22%, or at least ~25% greater, amount in corneal cells after 15 minutes than a corresponding amount of the compound when the functional formulation is not combined with the API. In aspects, such functional formulations comprising a delivery agent conferring such functionality also provide for the compound to be retained in at least ~15%, such as for example at least ~10%, at least ~12%, at least ~15%, at least ~17%, at least ~20%, at least ~22%, or at least ~25% greater amount in corneal cells after 15 minutes than a corresponding amount of the compound when no such delivery agent is present.

According to certain facets, the formulations described in this section can comprise one or more excipients. Such possible excipients are described in detail herein; however, in certain aspects of the invention, one or more excipients can be selected from a smaller group comprising one or more of a viscosity-enhancer, osmotic modification agent, surfactant, chelating agent, tonicity agent, buffer, pH-adjusting agent, a preservative, or water. In certain aspects, a formulation of the invention can comprise at least one viscosity enhancing excipient. In certain aspects, the viscosity enhancing agent can contribute to the viscosity of the formulation. In certain other aspects, the viscosity enhancing agent may not contribute to the final formulation viscosity but is present to serve an alternative purpose and its viscosity enhancing properties, which may be present in certain formulations, is not present in other formulations. In certain aspects, the viscosity of a formulation of the invention is between about 10 cps and about 400 cps, such as for example between about 25 cps to about 300 cps. In aspects, the viscosity of a formulation comprising liposomes or microspheres is at least about 5%, such as at least ~1% higher, at least ~2% higher, at least ~3% higher, at least ~4% higher, at least ~5% higher, at least ~6% higher, at least ~7% higher, at least ~8% higher, at least ~9% higher, or at least ~10% higher or more than the viscosity of a similar composition comprising the compound without the presence of liposomes or microspheres. In certain aspects, the use of a viscosity enhancing excipient further increases the viscosity of the formulation, such as for example the presence of a viscosity enhancing agent can increase the viscosity of a composition by at least ~1%, at least ~2%, at least ~3%, at least ~4%, at least ~5%, at least ~6%, at least ~7%, at least ~8%, at least ~9%, or at least ~10% or even higher, such as at least ~15%, at least ~20%, at least ~30%, at least ~40%, at least ~50%, at least ~75%, or even double, triple, or increase the viscosity of a formulation hundreds of times, e.g., ~200, ~400, ~600, or ~800 or more times over the viscosity of a similar formulation without a viscosity enhancing agent.

According to certain aspects, a pharmaceutical formulation of the invention can comprise a concentration of a compound described herein in a concentration of between about 0.1-about 10% w/v, such as between ~0.1-~8% w/v, ~0.1-~6% w/v, ~0.1-~4% w/v, ~0.1-~2% w/v, or ~0.1-~1% w/v, such as for example between ~0.3-~5% w/v, 0.3-~4% w/v, ~0.3-~2% w/v, or ~0.3-~1% w/v, as in for example ~0.6-~5% w/v, 0.6-~4% w/v, ~0.6-~2% w/v, or ~0.6-~1% w/v, such as for example between ~1-~8% w/v, between ~1-~6% w/v, between ~1-~4% w/v, or for example approximately 2.5% w/v.

According to certain aspects, a pharmaceutical formulation of the invention can comprise a concentration of a complexing agent described herein in a concentration of between about 0.1-about 10% w/v, such as between ~0.1-~8% w/v, ~0.1-~6% w/v, ~0.1-~4% w/v, ~0.1-~2% w/v, or ~0.1-~1% w/v, such as for example between ~0.3-~5% w/v, 0.3-~4% w/v, ~0.3-~2% w/v, or ~0.3-~1% w/v, as in for example ~0.6-~5% w/v, 0.6-~4% w/v, ~0.6-~2% w/v, or ~0.6-~1% w/v, such as for example between ~1-~8% w/v, between ~1-~6% w/v, between ~1-~4% w/v, or for example approximately 2.5% w/v.

In aspects, excipients that can be incorporated into formulations of the invention can comprise any suitable excipient such as those commonly used in pharmaceutical formulation development, e.g., those used for stability, preservation, pH control and the like. In certain common aspects, one or more pharmaceutically acceptable excipients used in the ophthalmic compositions include but are not limited to a thickening agent or viscosity-enhancer, solubilizers, penetration enhancers, chelating agents, tonicity agents, buffers or pH-adjusting agents, preservatives, and water.

In aspects, the solubilizer and the penetration enhancer are the same component (e.g., the same compound serves both to solubilize and enhance penetration). In alternative aspects, separate compounds can serve each function. Exemplary solubilizers and penetration enhancers include, but are not limited to, polysorbate 80, tocopherol polyethylene glycol succinate (TPGS), polyoxyl 35 castor oil, polyarginine, polyserine, tromethamine (tris), and sesame seed oil. The solubilizer and the penetration enhancer can be present is in an amount of about 0.5% to 2% by weight, such as for example ~0.1-~5% by weight, ~0.2-4% by weight, ~0.3-~3% by weight, or for example ~0.5-~2% by weight.

In aspects, viscosity-enhancing agents are used in the ophthalmic compositions to improve the form of the formulation for convenient administration and to improve contact with the eye and thereby improve availability and/or bioavailability. Exemplary thickening agents include polymers containing hydrophilic groups such as monosaccharides and polysaccharides, ethylene oxide groups, hydroxyl groups, carboxylic acids, or other charged functional groups. While not intending to limit the scope of the invention, in aspects viscosity-enhancing agents such as hydroxypropyl methylcellulose (HPMC), sodium carboxymethylcellulose, povidone, polyvinyl alcohol, and polyethylene glycol can be used.

High viscosity forms of ophthalmological formulations and the agents for achieving the same are known. TOBREX®, discussed in the background of the present disclosure, is available in two forms, one being a (drop) form and the other being an ointment, ointments being a common formulation strategy for improving ocular drug delivery well known in the art. A key to topical ophthalmological active efficacy is the ability to maintain contact with the surface of the eye which is impeded by the eyes natural defense mechanism which include such things as nasolacrimal flushing. The eye can be more successful at flushing thinner solutions than thicker, more viscous solutions, hence many in the art have sought to improve ophthalmologic drug delivery using viscosity enhancers. Methylcellulose, hydroxy methyl cellulose, hydroxy ethyl cellulose, sodium carboxy methyl cellulose, hydroxypropyl methyl cellulose, polyalcohol, e.g., polyvinyl alcohol, and polyvinylpyrrolidone are just a few examples of commonly used viscosity enhancers. International Patent Publication Number PCT/US2010/039618 (Kabra) is an example of existing art wherein xanthan gum is described as a viscosity enhancing agent. The Kernt, European Journal of Ophthalmology publication referenced in the background section of this application also discloses viscosity-enhanced solutions (e.g., viscosity enhanced solutions of 0.3% tobramycin). Such art demonstrates that viscosity enhancement is known and as some of the viscosity enhancers of the prior art can be suitable for the formulations described herein (e.g., they are pharmacologically acceptable and ophthalmologically safe and do not cause interference with the eye); in aspects, such viscosity enhancers can be accordingly incorporated into formulations described here.

In aspects, viscosity-enhancing agents can be present from about 0.1% to about 2% by weight, such as for example 0.1-~5% by weight, about 0.2-4% by weight, ~0.3-~3% by weight, or for example about 0.5-~2% by weight. According to certain aspects, the viscosity enhancer can increase the viscosity of the formulation from about 1 to about 700 cps at a shear rate of 6 sec-1 and a temperature of 25° C.

In aspects, tonicity agents are used in the ophthalmic compositions to adjust the composition of the formulation to be within a desired isotonic range. Examples thereof include ionic isotonic agents, non-ionic isotonic agents, and the like. Examples of the ionic isotonic agents include inorganic salts and organic salts. Examples of the inorganic salts include sodium chloride, disodium phosphate, sodium dihydrogen phosphate, potassium dihydrogen phosphate, sodium hydrogen sulfite, sodium sulfite, sodium thiosulfate, magnesium sulfate, potassium chloride, calcium chloride, magnesium chloride, boric acid, borax, and the like. Examples of the organic salts include potassium acetate, sodium acetate, sodium hydrogen carbonate, sodium carbonate, and the like. Examples of the non-ionic isotonic agents include polyhydric alcohols having two or more alcoholic hydroxy groups in single molecules, and the like. Specific examples of the polyhydric alcohols include, for example, glycerol, propylene glycol, polyethylene glycol, glucose, trehalose, mannitol, dextrose, sucrose, xylitol, sorbitol, and the like.

In certain aspects, formulations of the invention can comprise one or more such tonicity agents. In aspects, one or more tonicity agents are present in a formulation in the amount of about 0.01% to 0.8% by weight, such as between ~0.01-~0.8% by weight, between ~0.01-~0.6% by weight, between ~0.01-~0.4% by weight, between ~0.01-~0.2% by weight, or between ~0.01-~0.1% by weight, as in for example between ~0.05-~0.8% by weight, 0.1-~0.7% by weight, 0.2-~0.6% by weight, or for example between ~0.3-0.5% by weight. In certain aspects, among these isotonic agents, the non-ionic isotonic agents are preferably polyhydric alcohols such as glycerin, propylene glycol, and polyethylene glycol; the ionic isotonic agents can in aspects preferably be inorganic salts such as boric acid and borax; in aspects glycerin and borax can be ore preferable; in aspects, one such agent can comprise or be glycerin.

According to certain aspects, the formulations described herein can have an osmolality of about 250 to about 350 mOsm/kg, such as ~200-~500 mOsm/kg, for example ~200-~400 mOsm/kg, ~200-~300 mOsm/kg, or for example ~300-~500 mOsm/kg. In aspects, the isotonic agents in the invention can be used alone, or two or more thereof can be used in any combination. In certain aspects, one tonicity agent is used. In certain aspects, more than one tonicity agents are used.

Chelating agents are used in ophthalmic compositions to enhance preservative effectiveness by forming stable water-soluble complexes (chelates) with alkaline earth and heavy metal ions. Exemplary chelating agents include, but are not limited to, ethylenediaminetetraacetic acid (EDTA), or salts thereof. In aspects, any one or more chelating agents are present in the formulation. In a typical aspect, the chelating agent is present in an amount from about 0.001-about 0.1% by weight, such as between ~0.005-~0.05% by weight, between ~0.01-~0.04% by weight, or e.g., between ~0.001-~0.05% by weight, or for example between ~0.05% and ~0.1% by weight.

Buffers or pH-adjusting agents in the ophthalmic compositions are used to adjust the pH to a desirable range. Exemplary buffers include, but are not limited to, phosphate buffer, citrate buffer, tris buffer, carbonate buffer, succinate buffer, maleate buffer and borate buffer alone or in combination thereof. According to certain aspects, the pH of the present solutions, compositions, and formulations described herein should be maintained within a pH range of 6.0 to 9.0. The amounts of buffers used in the composition ranges to aid in such pH maintenance can, in some aspects, range from between about 0.05% to about 2.5% by weight, such as for example between ~0.05%-~2% by weight, 0.05%-~1.5% by weight, or between ~0.05%-~1% by weight, or for example between ~0.1%-~20.5% by weight, between ~0.5%-~20.5% by weight, or between ~1%-~20.5% by weight.

Preservatives in the ophthalmic compositions are used to inhibit microbial growth. In aspects, suitable nontoxic preservatives include, but are not limited to, zinc chloride, sodium chlorite, sodium hydroxymethyl glycinate, polyquaternium compound such as polyquaternium-1, cationic compounds such as chlorhexidine gluconate, p-hydroxybenzoates such as methyl p-hydroxybenzoate, ethyl p-hydroxybenzoate, propyl p-hydroxybenzoate and butyl p hydroxybenzoate, alcohol compounds such as phenylethyl alcohol, benzyl alcohol and chlorobutanol, sodium dehydroacetate; amino acids such as cysteine and methionine, citric acid and sodium citrate and other preservatives such as thimerosal, octadecyldimethylbenzyl ammonium chloride, hexamethonium chloride, benzethonium chloride, phenol, catechol, resorcinol, cyclohexanol, 3-pentanol, m-cresol, phenylmercuric nitrate, phenylmercuric acetate or phenylmercuric borate, sodium perborate and the like either alone or in combination thereof. In certain aspects, the formulations described herein comprise one or more preservatives. In aspects, the amount of preservative used in the composition ranges from about 0.005% to about 0.3% by weight, such as ~0.007-~0.2% by weight, or for example between ~0.01%-~0.1% by weight.

In aspects, compositions/formulations described herein can comprise one or more agents which may provide antimicrobial activity beyond that which is provided by the primary active(s), provide preservative functionality, serve as a surfactant, or any combination thereof. In aspects, one or more such compounds can be a quaternary ammonium compound, such as benzalkonium chloride. In aspects, a quaternary ammonium compound can be present in a composition/formulation in an amount that detectably or significantly (DOS) extends the preservation of the composition/formulation (e.g., extend shelf life), DOS increase the antimicrobial activity beyond that of the primary active(s), to effectively serve as a surfactant, or any combination thereof. In aspects, compositions/formulations described herein comprise, e.g., between about 0.01-about 0.2 mg/mL of benzalkonium as a 10% solution, such as between ~0.02-~0.19 mg/mL, between ~0.03-0.18 mg/mL, between ~0.04-0.17 mg/mL, between ~0.05-0.16 mg/mL, between ~0.06-0.15 mg/mL, between ~0.07-0.14 mg/mL, between ~0.08-0.13 mg/mL, between ~0.09-0.12 mg/mL, or about 0.1 mg/mL of a 10% solution of benzalkonium chloride. According to certain aspects, compositions/formulations described herein comprise no benzalkonium chloride. That is, in aspects, compositions/formulations can be free of benzalkonium chloride.

According to certain aspects, compositions/formulations described herein comprise no additional pharmaceutically active ingredients.

In aspects, it can be beneficial to incorporate one or more additional agents into the compositions and formulations described herein. For example, in aspects, compositions described herein can comprise (1) an antibacterial component comprising (a) a complex comprising (i) an active pharmaceutical ingredient (API) (primary active) wherein the active pharmaceutical ingredient is tobramycin, a similar compound, or a derivative of either thereof and (ii) a complexing agent, or (b) a derivative of tobramycin or a similar compound comprising one or more conjugates/derivatizing groups, wherein the complexing agent or conjugate(s) cause a detectable increase in API permeation of corneal cells, retention in corneal cells, or both, as compared to the non-complexed or non-derivatized API, and (2) an effective amount of one or more additional active agents, e.g., an anti-inflammatory agent, such as an NSAID or steroid (e.g., dexamethasone or another dexamethasone compound).

In aspects, a single composition or a single formulation can comprise compositions comprising compounds of the invention described herein and can further comprise one or more additional agents within the same composition or formulation (e.g., a combination composition or combination product) as opposed to such one or more agents being co-administered as described elsewhere herein. In aspects, such an agent may not be a pharmaceutically active ingredient. In aspects, such an agent can be a supplement. In aspects, such an agent can be a pharmaceutically active ingredient. As used herein, a pharmaceutically active ingredient, or alternatively stated, an active pharmaceutical ingredient (API) is an ingredient which demonstrated biological activity and is regulated by the United States Food and Drug Administration (FDA) for use in the United States. While many ingredients can demonstrate biological activity, some ingredients may not require FDA approval for incorporation into such formulations as ophthalmologic formulations and hence, as used herein, such ingredients are not considered an API. In aspects, a non-API ingredient can still demonstrate biological activity. In certain aspects, the term "active", such as an "active" agent, can be any ingredient demonstrating biological activity. In certain aspects, any formulation described herein can further comprise one or more additional actives. Such an agent/active can be any pharmaceutically acceptable, ophthalmologically safe component which does not significantly impede the performance of any one or more other co-present actives. Any such agent/active, in aspects, is suitable for co-administration with the primary compounds of the compositions described herein. In aspects, such an additional agent or active can be any agent or active generally supportive of ocular health or supportive of treating a condition of the eye or its adnexa, such as, e.g., one or more ophthalmologically suitable forms of an antihistamine (e.g., ketotifen fumarate, alcaftadine, azelastine, bepotastine, cetirizine, emedastine, epinastine, ketotifen, olopatadine, and the like); a decongestant (e.g., naphazoline, phenylephrine, oxymetazoline, tetrahydrozoline, or the like); one or more ophthalmologically suitable lubrication agents (e.g., agents comprising one or more ingredients common in eye lubrication compositions such as but not limited to, e.g., glycerin, propylene glycol, polyvinyl alcohol, povidone, polyethylene glycol, dextran, methylcellulose, hydroxypropyl methylcellulose, a polysorbate (e.g., polysorbate 80), petrolatum, mineral oil, lanolin, chlorobutanol, sodium chloride, Hypromellose, phosphoric acid, sodium hydroxide, sodium perborate, carboxymethylcellulose, polyvinylpyrrolidone, boric acid, potassium chloride, sodium borate, sodium chlorite, sodium hyaluronate, retinyl palmitate, tocopheryl acetate, magnesium ascorbyl phosphate, phenoxyethanol, and glyceryl); or one or more ophthalmologically suitable supplements (e.g., but not limited to an antioxidant such as lutein or zeaxanthin, or a vitamin such as, e.g., vitamin A, vitamin C, or vitamin D). In certain aspects, such an active can be a prostaglandin, such as bimatoprost, latanoprost, or other prostaglandin compounds or derivatives of the same. In aspects, such an active can be included which supports the treatment of the indication for which the compounds of the invention are targeted. That is, for example, an active can be incorporated which further addresses an ocular infection, such as, for example, one or more additional antimicrobial agents. Also, one or more additional actives can be incorporated which address one or more conditions related to the primary indication. As an example, in one aspect, the formulations described herein can include one or more anti-inflammatory agents, as inflammation often accompanies infection or, also, can result from the application of foreign material such as a drug treatment to the eye. In aspects, such an additive can be a non-steroid anti-inflammatory drug (NSAID) (such as, e.g., bromfenac, indomethacin, diclofenac, flurbiprofen, ketolorac tremethamine, or nepafenac). In aspects, such an additive can be a steroid or corticosteroid, such as, e.g., difluprednate, fluocinolone, fluorometholone, triamcinolone, rimexolone, prednisolone, medrysone, dexamethasone, or loteprednol (e.g., loteprednol etabonate). In certain aspects, compositions can comprise an anti-inflammatory steroid such as dexamethasone.

In aspects, the concentration of one or more additional actives in a composition/formulation can be any concentration suitable to achieve a targeted result, such as a sufficient concentration to DOS inhibit growth of an infective agent (e.g., if the active exhibits antimicrobial activity), or e.g., a sufficient concentration to DOS reduce or eliminate inflammation). According to certain aspects, an additional active can be an ophthalmologically suitable antimicrobial agent, such as an antibacterial agent, according to Formula I, Formula II, or Formula III described herein. In aspects, the concentration of such an antimicrobial agent within a composition/formulation can be less than, the same as, or higher than the primary complexed active compound. In aspects, the concentration of such an antimicrobial agent within a composition/formulation can be, e.g., between about 0.01-about 10%, such as between ~0.01-~9% w/v, ~0.01-~8% w/v, ~0.01-~7% w/v, ~0.01-~6% w/v, ~0.01-~5% w/v, ~0.01-~4% w/v, ~0.01-~3% w/v, ~0.01-~2% w/v, ~0.01-~1% w/v, such as between about 0.2-about 6% w/v, or between about 0.3-about 5% w/v.

According to certain aspects, an additional active can be an anti-inflammatory agent, such as an ophthalmologically suitable non-steroidal anti-inflammatory (NSAID) agent or a steroid. In aspects the agent can be a steroid. In specific aspects, the agent can be dexamethasone or a dexamethasone compound. A "dexamethasone compound" is a compound that is a recognized or known analog of dexamethasone or an analog having a substantially similar structure and exhibiting substantially similar properties as dexamethasone, but excluding steroids recognized as distinct from dexamethasone in the art, a derivative of dexamethasone or a dexamethasone analog, an alternative form of dexamethasone (e.g., a salt form other than the commonly used disodium phosphate form of dexamethasone) or an alternative form of a known dexamethasone analog or derivative, or a complex comprising any one or more of such compounds, in any case which exhibits similar or improved pharmaceutical activity as dexamethasone in the context of the formulations and methods described herein. A dexamethasone compound can in aspects be a stereochemically isomeric form (an isomer) of dexamethasone or a tautomer of dexamethasone. In aspects, the dexamethasone or other dexamethasone compound can be present in any suitable form. Examples of dexamethasone analogs and derivatives are known in the art (see, e.g., Galassi F et al. Br J Ophthalmol. 2006 November; 90(11):1414-9. doi: 10.1136/bjo.2006.099838). In aspects, the steroid content of the formulation comprises dexamethasone, primarily comprises dexamethasone, consists essentially of dexamethasone, or consists of dexamethasone. In aspects, compositions herein can comprise one or more other active agents, such one or more other active agents present in any suitable form, such as any suitable derivatized form, any suitable salt form, any suitable isomer form, any suitable tautomeric form, or any other derivative thereof. For example, a second antimicrobial agent can be present in any suitable form such as a salt, or, also or alternatively, an anti-inflammatory agent such as an NSAID or a steroid can be present in any suitable form, such as a salt. In aspects, the composition(s) herein comprise(s) a salt of dexamethasone or a dexamethasone compound, such as a disodium phosphate salt. In aspects, the dexamethasone or dexamethasone compound is associated with a pharmaceutically acceptable salt other than a disodium phosphate salt. Pharmaceutical salts are known in the art, and, in aspects, alternative salts can be selected without undue experimentation. Examples of pharmaceutical salts are well known in the art (see, e.g., Berge, "Pharmaceutical Salts"; Journal of Pharmaceutical Sciences; Volume 66, Issue 1, January 1977; Pages 1-19).

In aspects, the concentration of an anti-inflammatory agent, e.g., an NSAID or steroid, such as, e.g., dexamethasone or a dexamethasone compound, within a composition can be, e.g., between about 0.01-about 1% w/v, such as between ~0.01-~0.9% w/v, between ~0.01-~0.8% w/v, between ~0.01-~0.7% w/v, between ~0.01-~0.6% w/v, between ~0.01-~0.5% w/v, between ~0.01-~0.4% w/v, between ~0.01-~0.3% w/v, between ~0.01-~0.2% w/v, between ~0.01-~0.1% w/v, or for example between about 0.02-about 0.3% w/v, such as between ~ 0.02-~0.25% w/v, ~0.02-~0.2% w/v, or between ~0.02-~0.15% w/v. In certain aspects, concentrations of an anti-inflammatory agent are the same as that in TOBRADEX® or other similar on-market products. In aspects, concentrations of an anti-inflammatory agent are about 1%, ~2%, ~3%, ~4%, ~5%, ~6%, ~7%, ~8%, ~9%, or about 10% or more less than that in TOBRADEX® or other similar on-market products. For example, in aspects, an anti-inflammatory agent such as dexamethasone or another dexamethasone compound is present in a concentration of between about 0.01-about 1% w/v, such as between ~0.02-~0.8% w/v, between ~0.04-~0.6% w/v, between ~0.06-~0.4% w/v, between ~0.08-~0.2% w/v, or in a concentration of about 0.1% w/v.

In aspects, compound or compound complexes of the invention can be present within a formulation comprising one or more additional active agents in a ratio of about 50:1, such as ~45:1, ~40:1,-35:1, ~30:1, or ~25:1, such as, e.g., ~20:1, ~15:1, ~10:1, ~5:1, or even ~1:1. E.g., in aspects a compound or compound complex of the invention can be present within a formulation comprising an additional antibacterial agent, wherein the ratio of the compound or compound complex of the invention is present with the antibacterial agent in a ratio of about 0.5:1, ~1:1, ~1:1.5, or, e.g., ~1:2 or more. In another example, a compound or compound complex of the invention can be present within a formulation comprising an anti-inflammatory agent, wherein the ratio of the compound or compound complex of the invention is present within the anti-inflammatory agent in a ratio of about 40:1, e.g., ~35:1, ~30:1, ~25:1, or, e.g., ~20:1. In one specific example, the invention is a formulation comprising ~2.5% w/v of a compound or compound complex described herein and ~0.1% w/v dexamethasone or dexamethasone compound, e.g., dexamethasone.

In a specific aspect, compositions of the invention can comprise (1) an ophthalmologically suitable complex, the complex comprising (a) an antimicrobial active pharmaceutical ingredient comprising an effective amount of a compound having a structure according to Formula I and (b) an ophthalmologically suitable lipophilic and amphoteric complexing agent, which forms a complex with the active pharmaceutical ingredient, and (2) a pharmaceutically effective amount of dexamethasone or another dexamethasone compound, wherein the complexing agent detectably promotes the uptake of the active pharmaceutical ingredient by corneal cells, the retention of the active pharmaceutical ingredient by corneal cells, or both, as compared to the free (non-complexed) active pharmaceutical ingredient alone. In aspects, the compound is tobramycin, the complexing agent is histidine, and the composition comprises dexamethasone.

Within the formulations described herein comprising a complexing agent, such complexes can be amenable for the replacement of the compounds described herein with other water soluble or hydrophobic active agents. In aspects, such other actives can be added to a formulation as described herein, such as for example to a formulation comprising one or more complexed compounds, one or more derivatized compounds, and either of such formulations with or without an additional delivery agent.

In one aspect, an additional additive can be complexed with a delivery agent as described herein. In an alternative aspect, such actives can be delivered by the presence of one or more delivery agents, such as a liposome or a microsphere. Hence, in certain aspects, the formulations previously described can also comprise one or more additional actives. The one or more additional actives can, in certain aspects, measurably enhance the ability of a compound of the invention to permeate, be retained by, or both permeate and be retained by the cornea of the eye when used in ophthalmic applications. In alternative aspects, the one or more additional actives may not significantly impact the ability of a compound of the invention to permeate, be retained by, or both permeate and be retained by the cornea when used in ophthalmic applications. In aspects, the use of a complexing agent or other delivery agent such as liposomes or microspheres can be used to delivery any of the actives disclosed herein in the absence of any of the compounds disclosed as an aspect of the invention.

In aspects, one or more other active agents can be beneficial for the treatment of an ocular condition. In certain aspects, such other actives can include but not be limited to i) anti-glaucoma drugs, such as the beta-blockers, e.g., timolol maleate, betaxolol, carteolol and metipranolol; epinephrine and prodrugs; such as dipivefrin; carbonic anhydrase inhibitors; such as dorzolamide, brinzolamide, acetazolamide, dichlorphenamide and methazolamide; dopaminergics, prostaglandins, docosanoids, alpha-2 agonists; angiotensin II antagonists; alpha-I antagonists; cannabinoids; endothelin antagonists; ii) miotics, e.g., pilocarpine, acetylcholine chloride, isoflurophate, demecarium bromide, echothiophate iodide, phospholine iodide, carbachol, and physostigmine; iii) drugs for treatment of macular degeneration, such as interferon, particularly α-interferon; transforming growth factor (TGF), e.g. TGF-P; iv) anti-cataract and anti-proliferative diabetic retinopathy (PDR) drugs, such as aldose reductase inhibitors: e.g. tolrestat, or angiotensin-converting enzyme inhibitors, e.g. lisinopril, enalapril; v) drugs for treatment of age-related exudative macular degeneration (AMD), e.g. ocular neovascular disease, such as staurosporines, phthalazine derivatives; vi) anti-clotting agents, such as tissue plasminogen activator, urokinase, and streptokinase; vii) drugs for treatment of ocular inflammatory diseases such as cortico-steroids; e.g. prednisolone, triamcinolone, dexamethasone, fluocinolone, cortisone, prednisolone, fluorometholone and the like, non-steroidal anti-inflammatory drugs, such as ketorolac tromethamine, didofenac sodium, indomethacin, flurbiprofen sodium, and suprofen; viii) antibiotics, such as cephaloridin, chloramphenicol, clindamycin, amikacin, gentamicin, methicillin, lincomycin, oxaciilin, penicillin, amphotericin B, polymyxin B, cephalosporin family, ampicillin, bacitracin, carbenicillin, cefalotin, colistin, erythromycin, streptomycin, neomycin, sulfacetamide, vancomycin, silver nitrate, sulfisoxazole diolamine, quinolones, and tetracycline; ix) anti-fungal or anti-viral agents, such as miconazole, ketoconazole, idoxuridine, trifluridine, vidarabine, acyclovir, gancyclovir, foscarnet sodium, cidofovir, valacyclovir, famciclovirtrisulfapyrimidine-2, nystatin, flucytosine, natamycin, aromatic diamidines e.g. dihydroxystilbamidine and piperazine derivatives, e.g. diethylcarbamazine; x) cycloplegics and mydriatic agents, such as atropine, cyclopentolate, scopolamine, homatropine tropicamide and phenylephrine; xi) drugs for the treatment of ocular neurodegenerative diseases such as isopropyl unoprostone, glutamate receptor antagonists, e.g. memantine, caspase inhibitors, calcium antagonists, sodium channel blockers, NOS-2 inhibitors or neurotrophic factors, e.g. glial derived neurotrophic factor (GDNF) or ciliary neurotrophic factor (CNTF); xii) peptide drugs such as calcitonin, lypressin or a somatostatin or analogues thereof, xiii) anti-VEGF drugs; xiv) phosphodiesterase inhibitors; xv) antisense drugs such as fomivirsen sodium; xvi) immunosuppressive agents; such as azathioprine, cyclosporin A, methotrexate, colchicine; xvii) drugs for the treatment of ocular angiogenesis such as angiostatic steroids, PKC inhibitors, VEGF antagonists, COX2 inhibitors, ACE inhibitors or angiotensin II antagonists; xviii) free radical scavengers, e.g. alpha tocopherol, carotenoids, sulfhydryl-containing compounds.

According to some aspects, the formulations of the invention can be delivered in any matrix suitable for the target condition. In certain aspects, the formulations described herein can be utilized to treat a non-ocular condition such as an infection of the skin, wherein a topical cream or ointment is a suitable method of administration. In certain common aspects, the formulations are developed for application to the eye. In aspects, matrices suitable for delivering active pharmaceutical agents to the eye include but may not be limited to ointments, solutions, emulsions, dispersions, and suspension.

In one aspect, formulations described herein can be delivered as a solution. In one embodiment, the formulations are delivered as a solution via drops administered to the eye. In certain alternative embodiments, the formulation is delivered as an ointment, wherein a strip of ointment is applied to the afflicted eye. As used herein, a description of a "drop" of a solution/formulation to the eye describes a drop size common in the art for ocular formulations designed to be delivered by liquid drop(s) to the eye or less, e.g., a volume of about 0.08 mL or less, such as ~0.07 mL, ~0.06 mL, ~0.05 mL, ~0.04 mL, ~0.03 mL, ~0.02 mL, or ~0.01 mL or less. As used herein, a description of a "strip of ointment" (or similar application of an ointment) is an amount of ointment typically used for such applications in the art or less, such as a strip of ¾" or less, such as an ~half-inch strip, ~one third-inch strip, ~one quarter inch strip, or less (e.g., ~3 cm, ~2 cm, ~1 cm, or -one-half cm or less).

According to certain aspects, the formulations described herein maintain the compounds of the invention in contact with the ocular surface (mucous membrane) of the eye for at least about 2 hours after application, such as for at least ~4 hours, at least ~8 hours, at least ~16 hours, at least ~20 hours, or for example at least about 24 hours after application. According to some facets, the formulations demonstrate at least about 5% higher, such as at least ~1% higher, at least ~2% higher, at least ~3% higher, at least ~4% higher, at least ~5% higher, at least ~6% higher, at least ~7% higher, at least ~8% higher, at least ~9% higher, or at least ~10% higher patient compliance as compared to TOBREX® as assessed by conducting two or more adequately powered and controlled as would be acceptable by a major regulatory authority, e.g., the United States FDA. In certain aspects, formulations described herein demonstrate at least 5% better, such as at least ~1% better, at least ~2% better, at least ~3% better, at least ~4% better, at least ~5% better, at least ~6% better, at least ~7% better, at least ~8% better, at least ~9% better, or at least ~10% better efficacy as compared to TOBREX® as assessed by conducting two or more adequately powered and controlled as would be acceptable by a major regulatory authority, e.g., the United States FDA. In certain other aspects, the formulations demonstrate at least 5% less, such as at least ~1% less, at least ~2% less, at least ~3% less, at least ~4% less, at least ~5% less, at least ~6% less, at least ~7% less, at least ~8% less, at least ~9% less, or at least ~10% less toxicity, e.g., surface toxicity, as compared to TOBREX® as assessed by conducting two or more adequately powered and controlled as would be acceptable by a major regulatory authority, e.g., the United States FDA. In aspects, the formulations demonstrate that on average fewer than 2 people in 100 treated with the formulation experience a hypersensitivity or localized ocular toxicity reaction such as lid itching and swelling, and conjunctival erythema as assessed by one or more physicians in an appropriately powered population of patients or by an appropriately powered clinical study.

Methods of Use

In aspects, the invention provides methods of treating conditions or disorders of a mammalian eye, e.g., an eye infected with an infective agent, comprising administering to the eye an ophthalmologically suitable pharmaceutical formulation, comprising an ophthalmologically suitable pharmaceutical composition which comprises an effective amount of an antimicrobial active pharmaceutical ingredient (API) which comprises an effective amount of a compound having a structure according to Formula I, Formula II, or Formula III described herein, wherein the compound is complexed with a lipophilic and amphoteric complexing agent, and further wherein the complexing agent detectably promotes the uptake of the composition by corneal cells, the retention of the complex by corneal cells, or both, as compared to the free compound. In aspects such formulations comprise one or more additional ophthalmologically suitable pharmaceutical ingredients. In aspects, the one or more additional active pharmaceutical ingredients is/are directed to further supporting the treatment of the primary indication for which the complexed compounds of the composition are directed (e.g., an infection of the eye or its adnexa), directed to addressing one or more conditions related to the primary indication (e.g., inflammation associated with an infection of the eye or its adnexa), or both. In aspects such an additional active can be an antimicrobial (e.g., antibacterial) agent. In aspects, such an additional active can be an anti-inflammatory agent.

According to certain aspects, the invention comprises a method of reducing the level of bacterial infection present in an eye comprising application of a formulation described herein. In aspects, described herein is a method of using a disclosed formulation to treat a patient suffering from an ocular disease or condition which may be sensitive to, e.g., susceptible to, or treated by, such a formulation. In some such applications, the disease or condition is an external infection of the eye, where in some aspects the external infection is caused by pathogen selected from a group comprising a gram positive or a gram-negative ophthalmic pathogen, e.g., Staphylococci, such as S. *Aureus* and S. *epidermis*. In aspects, infective agents treatable by formulations described herein can further include *Haemophilus influenza, Streptococcus pneumoniae, Pseudomonas aeruginosa*. In aspects, an infective agent treatable by the formulations described herein can be described as a coagulase-negative *staphylococcus*, a streptococci, or a gram-negative bacilli. In certain aspects, the pathogen is a penicillin resistant strain. In aspects, the formulations herein are capable of treating ocular infective agents which may not have responded to current-on market drugs, or which have not effectively responded to a previous treatment. Examples of organisms which may be treatable by formulations described herein and, in further aspects, which may be treatable by formulations herein after having previously been unresponsively treated with a prior treatment include but may not be limited to *Staphylococcus aureus, Streptococcus* (including *Streptococcus pneumoniae*), *Escherichia coli, Haemophilus influenzae, Klebsiella/Enterobacter* species, *Moraxella lacunata*, and, e.g., *Neisseria* species.

In certain aspects, formulations successful in such methods comprise one or more compounds of the invention in a concentration of between about 0.1-about 10% w/v, such as for example between ~0.1-~5% w/v, 0.1-~4% w/v, 0.1-~3% w/v, ~0.1-~2% w/v, ~0.1-~1% w/v, or for example between ~0.3-~5% w/v, as in for example between ~0.6-5% w/v, between ~1-3% w/v, or for example approximately 2.5% w/v. In certain aspects, wherein the formulation comprises a complexing agent, formulations successful in such methods comprise one or more complexing agents described herein in a concentration of between ~0.1-~10% w/v, such as for example between ~0.1-~5% w/v, 0.1-~4% w/v, 0.1-~3% w/v, ~0.1-~2% w/v, ~0.1-~1% w/v, or for example between ~0.3-~5% w/v, as in for example between ~0.6-5% w/v, between ~1-3% w/v, or for example approximately 2.5% w/v.

According to aspects, the formulations described herein can be administered four times per day or less and achieve efficacious results. In aspects, the formulations can be administered less frequently, such as, e.g., three times per day or less, twice per day or less, or in some instances the formulations can be administered once per day (e.g., once daily), such as, e.g., effective treatment can be attained by applying formulation(s) described herein to an infected eye no more than four times per 24-hour period (e.g., per day), 3 times per day, 2 times per day, or for example no more than once per day. In aspects, a single treatment is a single drop of formulation. In other aspects, a single treatment is two drops of formulation. Therefore, in facets, effective treatment of an ocular infection can be attained by applying a single drop of a formulation described herein to the infected eye 4×/24-hour period, 3×/24-hour period, 2×/24-hour period, or once/24-hour period. In aspects, two drops of a formulation described herein applied to the infected eye 2×-4×/24-hour period or once/24-hour period can effectively treat an ocular infection.

In embodiments, a formulation comprises a complexed compound in solution for administration via drops to the eye approximately twice daily for the treatment of an external infection of the eye.

In aspects wherein corneal permeation is statistically increased, the onset of symptom improvement following a standard administration protocol is detectably or significantly faster, such as for example at least ~2 hours faster, at least ~4 hours faster, at least ~6 hours faster, at least ~8 hours faster, at least ~12 hours faster, at least ~16 hours faster, at least ~20 hours faster, or, for example at least ~24 hours faster, than that of the non-complexed compound, as assessed by a qualified professional or as self-reported in an appropriately controlled study of a patient population. In certain facets, a single course of administration of a treatment comprising the composition resolves the condition for which the course of administration is prescribed at least about 1% more frequently, such as about 2%, ~3%, ~4%, ~5%, ~6%, ~7%, ~8%, ~9%, or ~10% more frequently or even higher success rates after a single course of administration comprising a complexed compound than a single course of administration of treatment comprising a similar composition comprising a non-complexed compound as assessed by conducting two or more adequately powered and controlled studies, as would be acceptable by a major regulatory authority, e.g., the United States FDA.

According to some aspects wherein corneal permeation is detectably or significantly, e.g., statistically increased, and administration of a composition comprising a complexed compound within a formulation requires an administration rate of no more than two thirds, such as no more than one halve and, in some cases no more than one third of the total number of doses required for a similar composition comprising a non-complexed compound over the same course of treatment.

According to certain facets wherein corneal cell retention/uptake is detectably or significantly increased, the onset of symptom improvement is at least detectably faster, such as for example at least ~2 hours faster, at least ~4 hours faster, at least ~6 hours faster, at least ~8 hours faster, at least ~12 hours faster, at least ~16 hours faster, at least ~20 hours faster, or, for example at least ~24 hours faster, in compositions and formulations comprising a complexed compound than that of a similar composition comprising a non-complexed compound, as assessed by a qualified professional or as self-reported in an appropriately controlled assessment of a patient population, or, for example, as assessed by conducting two or more adequately powered and controlled studies as would be acceptable by a major regulatory authority, e.g., the United States FDA. The terms "retention" and "uptake" in this and in any other aspect of this disclosure can be used interchangeably herein to describe the type of effect exemplified in the Examples below, in which a greater amount of API is in corneal cells after a period of administration.

In certain aspects wherein retention is increased, a single course of administration of a treatment comprising a composition and/or formulation comprising a complexed compound resolves the condition for which the course of administration is prescribed at least about 1% more frequently, such as at least ~1%, ~2%, ~3%, ~4%, ~5%, ~6%, ~7%, ~8%, ~9%, or at least ~10% more frequently than a single course of administration of a treatment comprising a similar composition with a non-complexed compound as assessed by conducting two or more adequately powered and controlled clinical studies ("studies") as would be acceptable by a major regulatory authority, e.g., the United States FDA.

In facets wherein retention is increased, a composition or formulation comprising a complexed compound requires an administration rate of no more than two thirds, e.g., no more than one half, and in facets no more than one third of the total number of doses required for a similar composition comprising a non-complexed compound over the same course of treatment.

According to some aspects wherein retention is increased, the rate of antibiotic resistance in a population receiving the composition comprising a complexed compound is significantly less than the rate of antibiotic resistance in a population having received a similar composition comprising a non-complexed compound.

According to certain facets wherein both corneal permeation and corneal retention is increased, the onset of symptom improvement is at least detectably faster, such as for example at least ~2 hours faster, at least ~4 hours faster, at least ~6 hours faster, at least ~8 hours faster, at least ~12 hours faster, at least ~16 hours faster, at least ~20 hours faster, or, for example at least ~24 hours faster, for a formulation comprising a complexed compound than that of a similar composition comprising a non-complexed compound, as assessed by a qualified professional or as self-reported in an appropriately controlled assessment of a patient population or as assessed by conducting two or more adequately powered and controlled studies as would be acceptable by a regulatory authority, e.g., the United States FDA.

In aspects wherein both corneal permeation and corneal retention is increased, a single course of administration of a treatment comprising a complexed compound resolves the condition for which the course of administration is prescribed at least about 1% more frequently, such as at least ~1%, at least ~2%, at least ~3%, at least ~4%, at least ~5%, at least ~6%, at least ~7%, at least ~8%, at least ~9%, or for example at least ~10% or even higher than a single course of administration of a treatment comprising a similar composition with a non-complexed compound as assessed by conducting two or more adequately powered and controlled studies as would be acceptable for demonstrating pharmaceutical efficacy by a major regulatory authority, e.g., the United States FDA.

In aspects wherein both corneal permeation and corneal retention are increased, the administration rate is no more than two thirds, such as no more than one half, and in certain facets no more than one third of the total number of doses required for a similar composition comprising a non-complexed compound over the same course of treatment.

In aspects, the rate of antibiotic resistance in a population receiving a composition or formula comprising a non-complexed compound is significantly less than in a population having received a similar composition comprising a non-complexed compound.

According to certain aspects, a formulation or composition comprising a derivatized compound which detectably increases the corneal permeation, corneal retention, or both the corneal permeation and corneal retention of a derivatized compound results in the onset of symptom improvement which is significantly faster, such as for example at least ~2 hours faster, at least ~4 hours faster, at least ~6 hours faster, at least ~8 hours faster, at least ~12 hours faster, at least ~16 hours faster, at least ~20 hours faster, or, for example at least ~24 hours faster, than that of a similar composition comprising tobramycin, as assessed by a qualified professional, as self-reported in an appropriately controlled assessment of a patient population, or as assessed by conducting two or more adequately powered and controlled clinical studies, as would be deemed acceptable to prove efficacy by a major regulatory authority, e.g., the United States FDA.

In certain aspects wherein a formulation or composition comprising a derivatized compound detectably increases the corneal permeation, corneal retention, or both the corneal permeation and corneal retention of a derivatized compound, a single course of administration of a treatment comprising the composition resolves the condition for which the course of administration is prescribed at least about 5% more frequently, such as at least ~6% more frequently, at least ~7% more frequently, at least ~8% more frequently, at least ~9% more frequently, or at least ~10% more frequently or more, than a single course of administration of a treatment comprising a similar composition with tobramycin as measured by an appropriately controlled clinical trial.

In some facets, the administration protocol of a formulation comprising a derivatized compound or composition comprising a derivatized compound requires an administration rate of no more than two thirds, such as no more than one half, such as no more than one third of the total number of doses required for a similar composition comprising tobramycin over the same course of treatment.

According to some aspects, the rate of antibiotic resistance in a population receiving a composition or formulation comprising a derivatized compound is significantly less than the rate of antibiotic resistance in a population having received a similar composition comprising tobramycin.

EXEMPLARY COMPLEXED COMPOUND PRODUCTION & FUNCTIONAL ASSESSMENT

To even further exemplify and illuminate aspects of the invention, the following description of illustrative applications of particular aspects of the invention is provided. These "Examples" are meant to exemplify particular facets of the invention but should not be used to limit the scope of the invention in any manner.

Example 1

A study was performed to examine the ability of tobramycin to form a complex with amphoteric, lipophilic materials suitable for ophthalmic use.

The following procedure was followed to form a tobramycin complex with histidine material to be used for evaluation. 5 g of tobramycin and 5 g of histidine were weighed and each dissolved in 50 mL of water, tobramycin being added first and completely dissolved prior to the addition and dissolution of histidine. The solution was then brought up to a final volume of 100 mL with water. The solution was then poured into open petri dishes and placed in an oven set at 40° C. and checked for complete drying. If plates were not completely dry after an initial check, they were allowed to dry for an additional 8 hours.

The following procedure was followed to form a tobramycin complex with the amphoteric polymer Soluplus® (polyvinyl caprolactam-polyvinyl acetate-polyethylene glycol graft copolymer (PCL-PVAc-PEG)) material to be used for evaluation. 5 g of tobramycin and 5 g of Soluplus® were weighed and dissolved in 50 mL of water, tobramycin being added first and allowed to completely dissolve prior to the addition and complete dissolution of Soluplus®. The solution was brought up to a final volume of 100 mL with water. The solution was then poured into open petri dishes and placed in an oven set at 40° C. and checked for complete drying. If plates were not completely dry, they were allowed to dry for an additional 8 hours.

After preparing the above dried compositions, the two products were analyzed in Differential Scanning Colorimeter (DSC) studies wherein the formation of a) a tobramycin complex with histidine and b) a tobramycin complex with the Soluplus® polymer were evaluated. The resulting DSC data is presented in FIGS. 1A-1D (tobramycin+histidine) and FIGS. 3A-3D (tobramycin+Soluplus®, and is summarized in Table 3, below.

TABLE 3

Summary of Differential Scanning Colorimeter (DSC) results of tobramycin complex with histidine and tobramycin complex with Soluplus ®.

| Sr. No | Sample Description | Sample Weight (mg) | Onset Temperature (° C.) | Peak Temperature (° C.) | Enthalpy (J/g) |
|---|---|---|---|---|---|
| 1 | Tobramycin, USP | 4.546 | First: 144.68 Second: 221.23 | First: 153.07 Second: 223.25 | First: 39.494 Second: 17.719 |
| 2 | Histidine USP | 4.864 | 284.75 | 287.56 | NA |
| 3 | Tobramycin + Histidine physical mixture | 6.309 | First: 142.57 Second: 219.29 Third: 255.07 | First: 149.70 Second: 220.43 Third: 260.86 | First: 44.146 Second: 29.296 Third: 118.01 |
| 4 | Tobramycin + Histidine complex ppt from solution | 7.225 | 260.04 | 276.32 | 314.96 |
| 5 | Tobramycin, USP | 4.546 | First: 144.68 Second: 221.23 | First: 153.07 Second: 223.25 | First: 39.494 Second: 17.719 |
| 6 | Soluplus in water | 6.46 | 247.03 | 250.68 | 10.3 |
| 7 | Tobramycin + Soluplus physical mixture | 6.16 | First: 145.35 Second: 231.64 | First: 151.65 Second: 223.33 | First: 38.733 Second: 30.463 |
| 8 | Tobramycin + Soluplus complex ppt from solution | 6.96 | First: 135.08 Second: 192.54 | First: 147.48 Second: 194.88 | First: 41.778 Second: 57.765 |

Figure 1C:
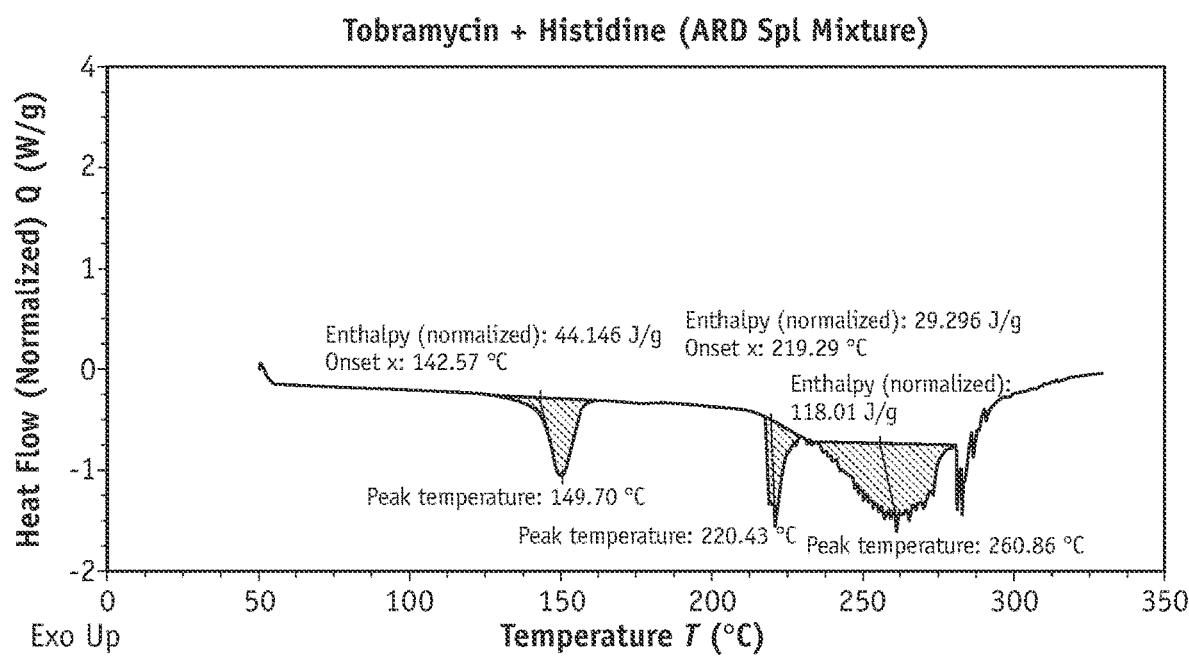
Figure 1D:
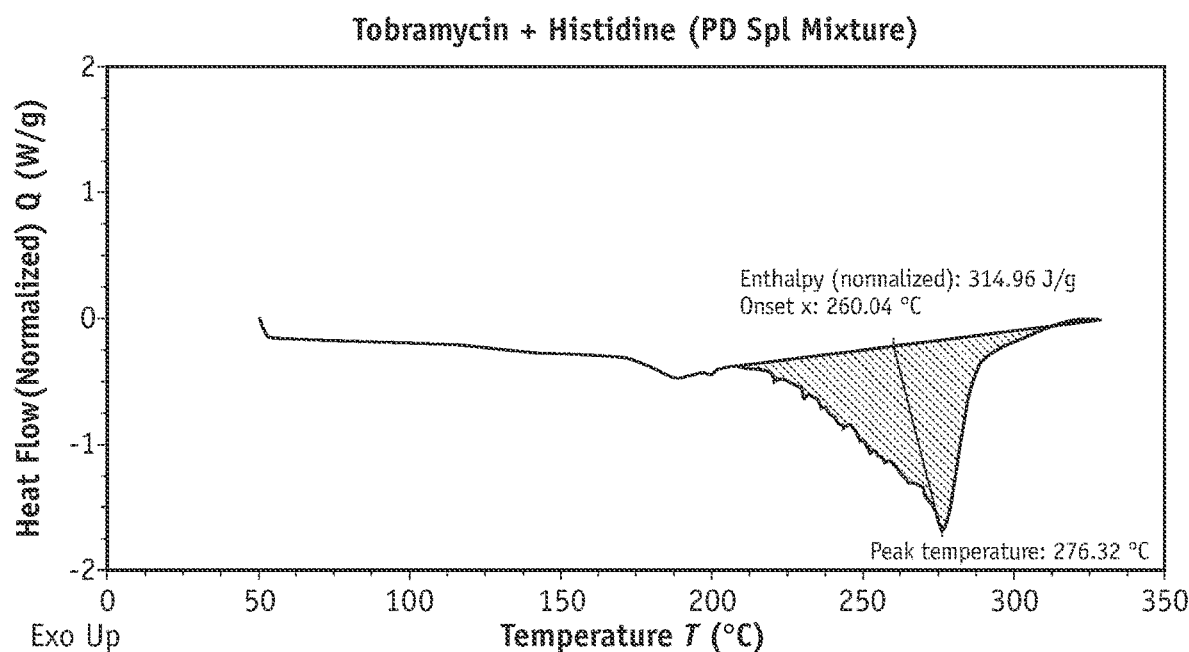

The results show that tobramycin forms a complex with both histidine and Soluplus® (again, chemically the amphoteric polymer polyvinyl caprolactam-polyvinyl acetate-polyethylene glycol graft copolymer). FIG. 1A shows the resulting DSC curve for tobramycin alone. FIG. 11B shows the resulting curve for histidine alone. As shown above, the tobramycin histidine complex precipitated from solution, forming a new peak at the onset temperature of 260.04° C. and having the peak at 276.32° C. FIG. 1C illustrates that while in the physical mixture of histidine and tobramycin, both peaks of tobramycin, one peak of histidine and one peak of complex are visible. FIG. 1D shows the resulting curve for the tobramycin+histidine complex.

Figure 3A:
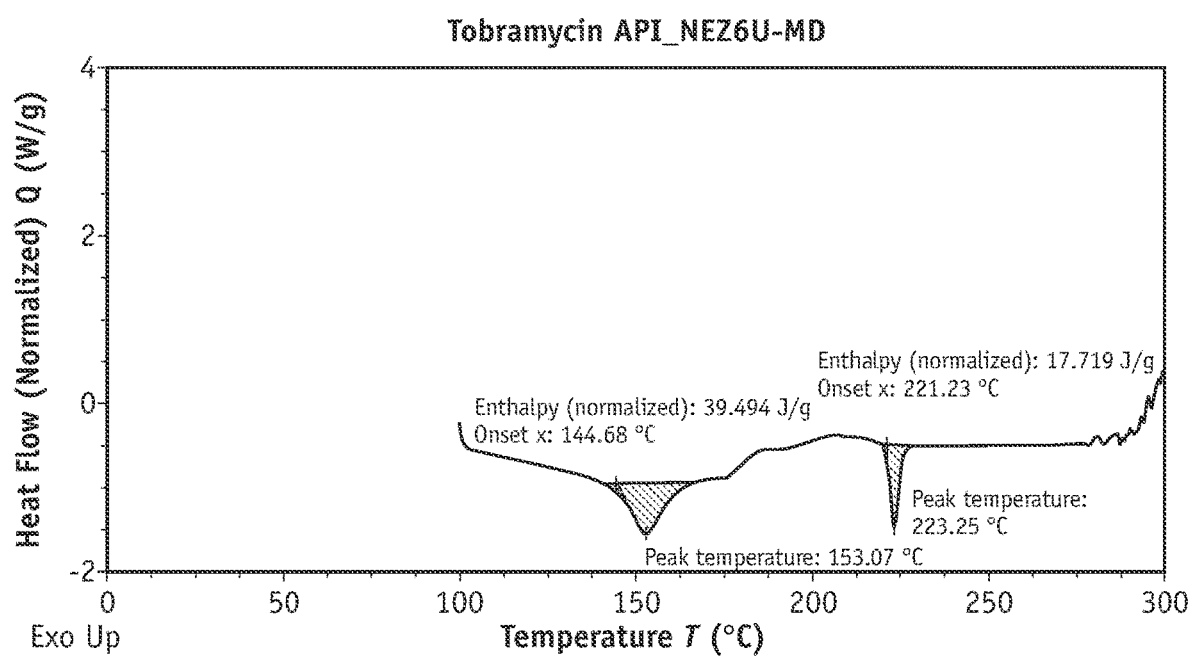
FIGS. 3A-3D are DSC spectra of tobramycin (FIG. 3A), Soluplus® (FIG. 3B), tobramycin+Soluplus® physical mixture (FIG. 3C), and a tobramycin+Soluplus® complex according to an aspect of the invention (FIG. 3D).
Figure 3B:
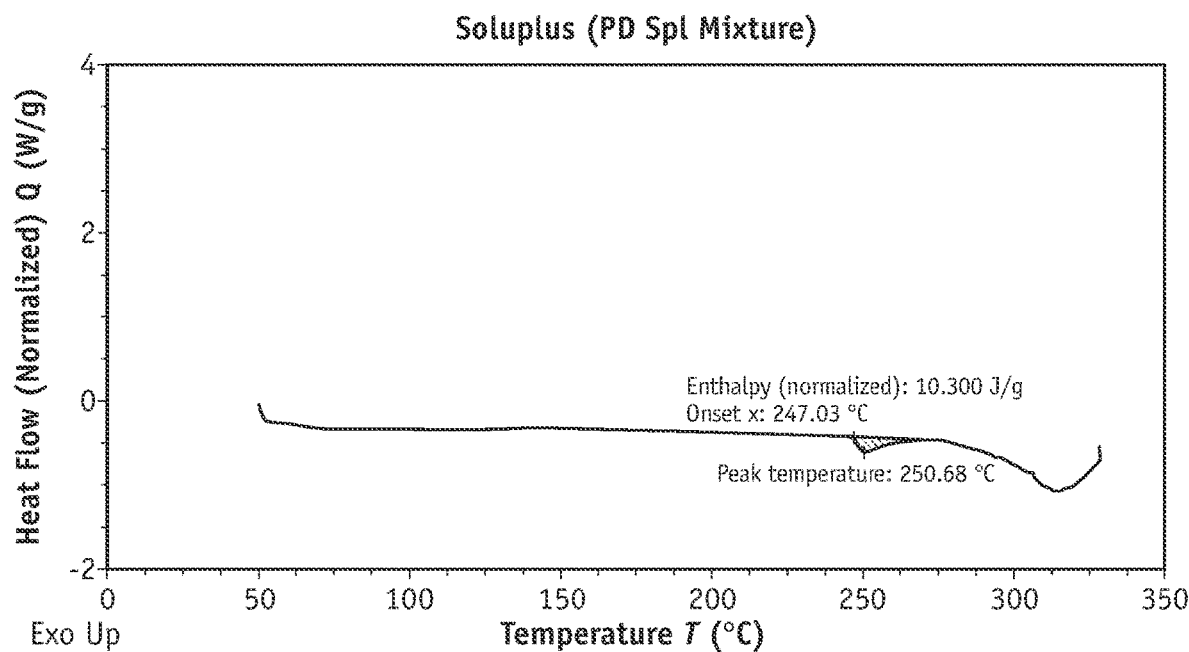
Figure 3C:
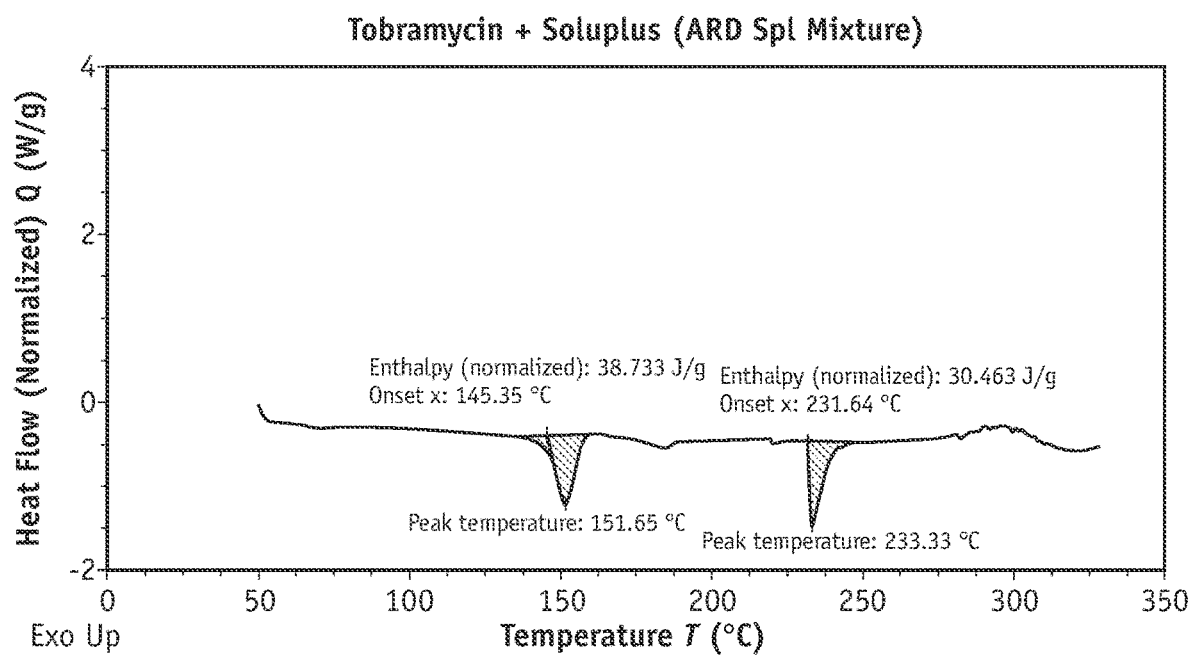
Figure 3D:
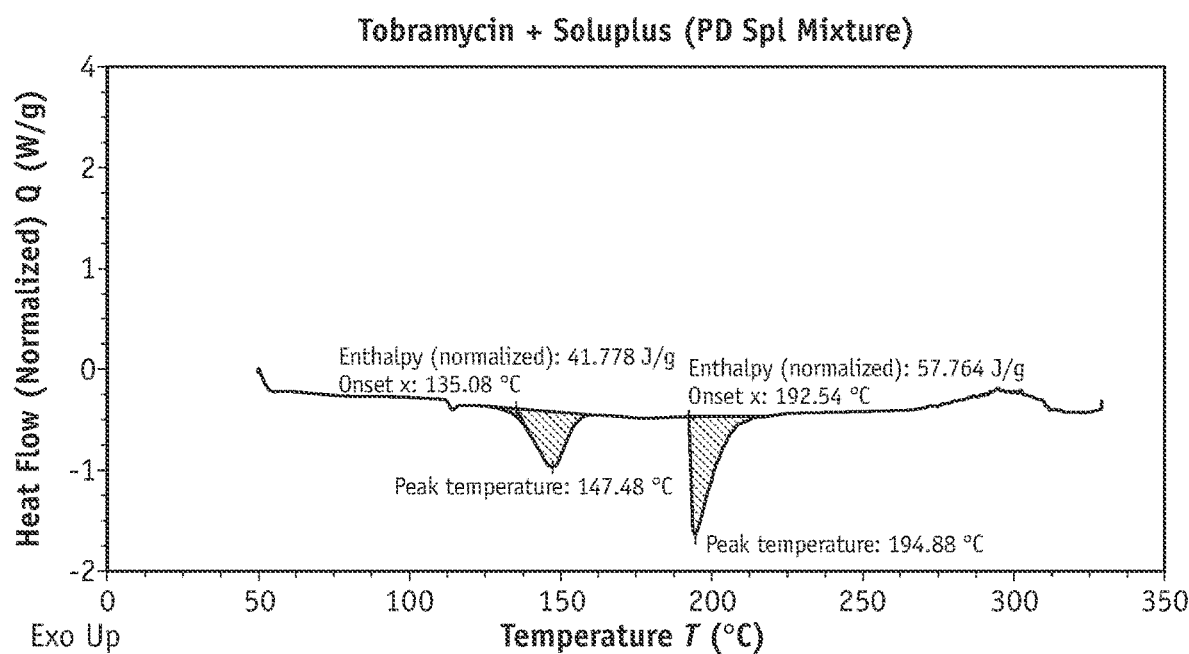

In case of Soluplus®, the DSC tobramycin peaks are shifted to lower temperatures (see FIGS. 3C and 3D). FIG. 3A shows the resulting peak of tobramycin alone. FIG. 3B shows the resulting peak of Soluplus® alone. The onset temperature of the first peak of tobramycin that starts at 144.68° C. is shifted to 135.08° C. and onset temperature of the second peak that starts at 221.23° C. is shifted to 192.54° C. in the mixture (see FIGS. 3C and 3D). Similarly, the peak temperatures also shifted to lower temperatures, from 153.07° C. to 147.48° C. and from 223.25° C. to 194.88° C. The change in the peak temperature of the second peak for tobramycin shows the formation of the complex.

Figure 2A:
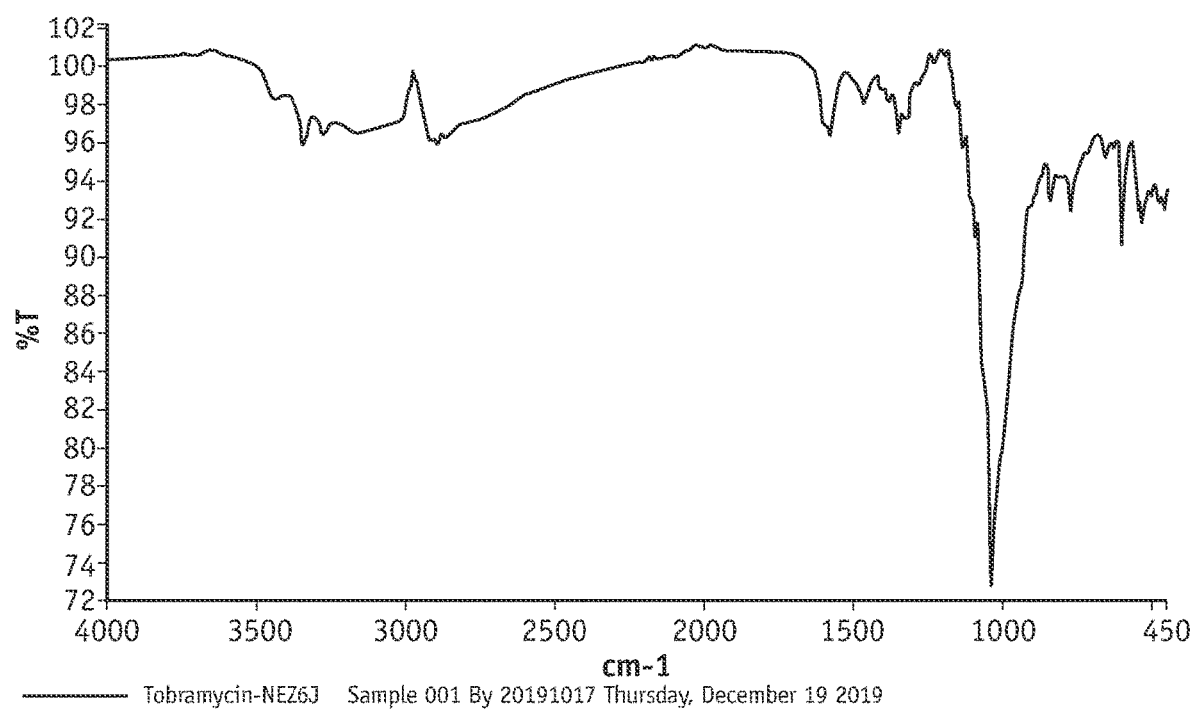
FIGS. 2A-2C are Fourier transform infrared (FTIR) spectra of tobramycin and histidine, each individually (FIGS. 2A and 2B), and a tobramycin+histidine complex of one aspect of the invention (FIG. 2C).
Figure 2B:
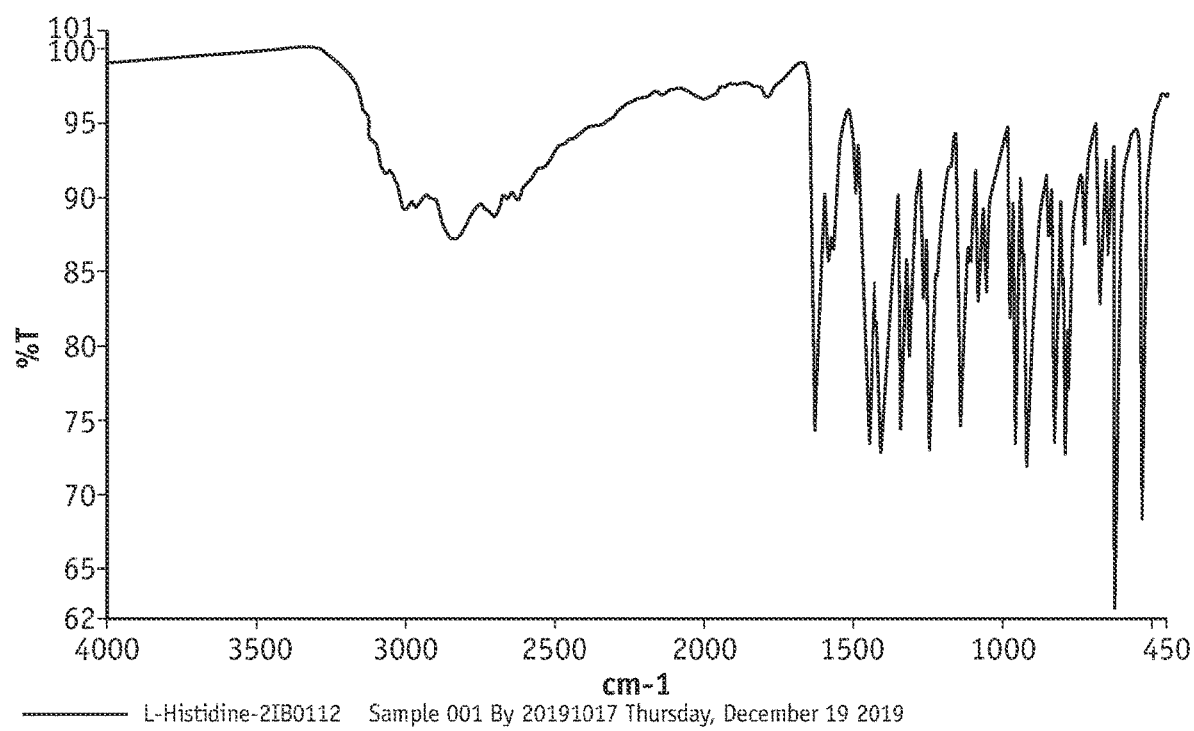
Figure 2C:
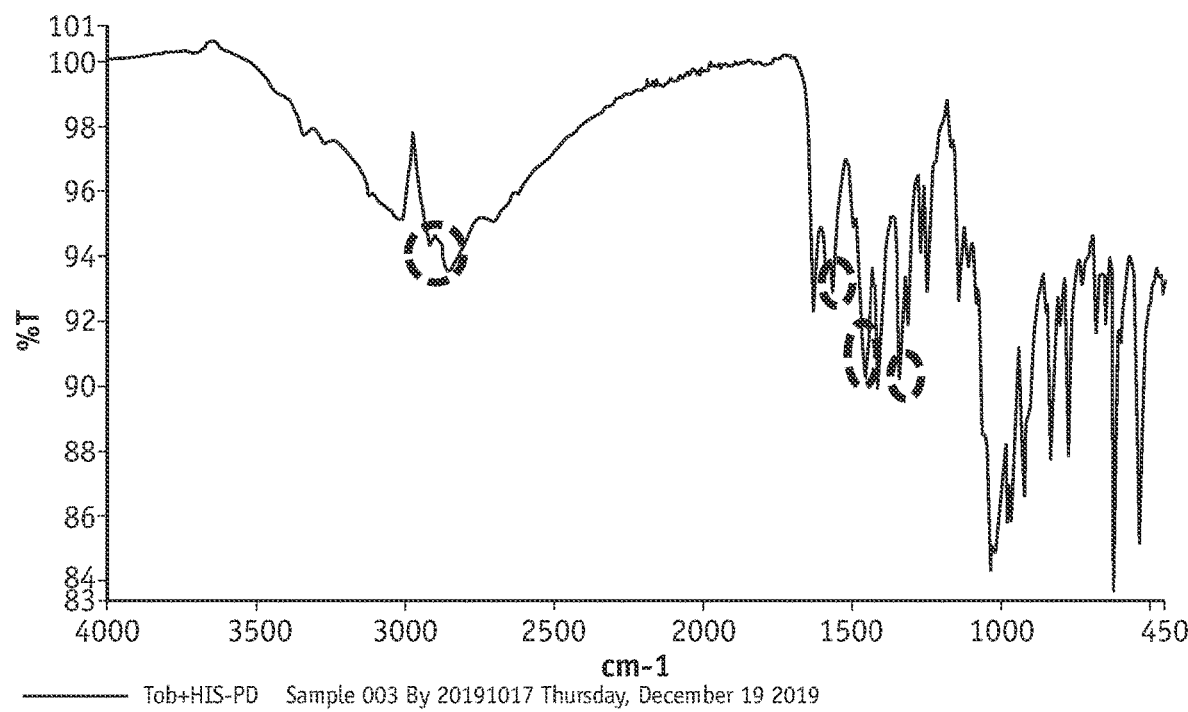
Figure 4A:
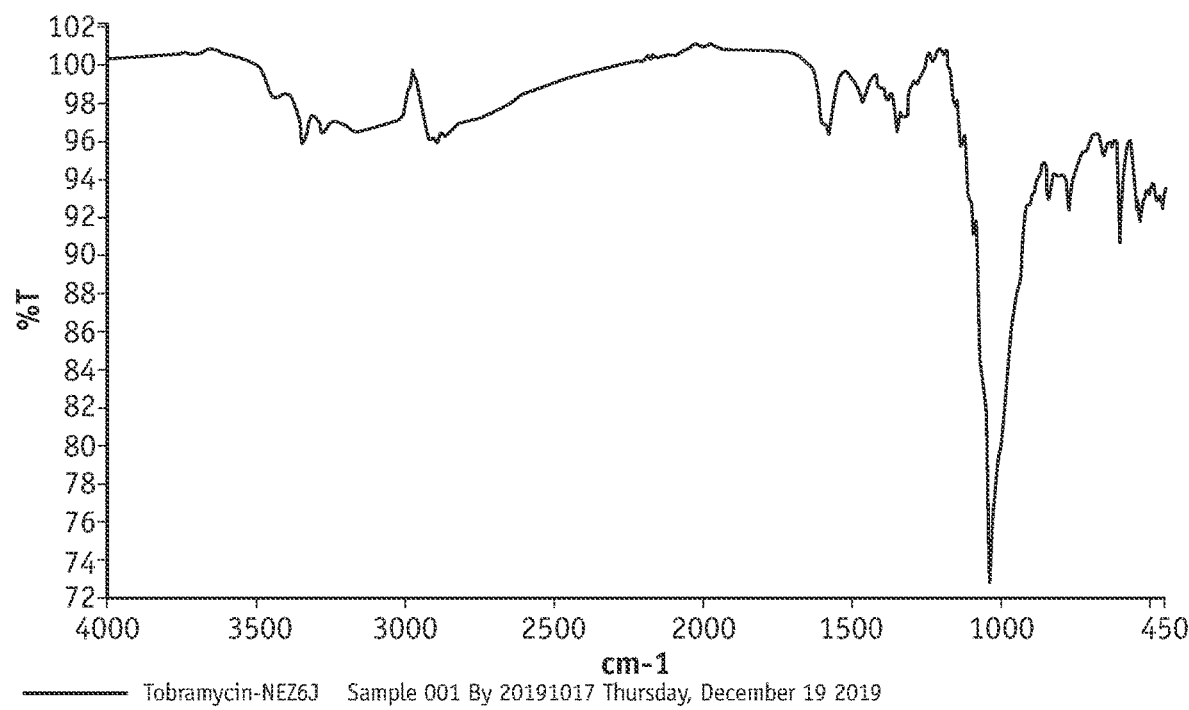
FIGS. 4A-4C are FTIR spectra of tobramycin and Soluplus® each individually (FIGS. 4A and 4B) and a tobramycin+Soluplus® complex.
Figure 4B:
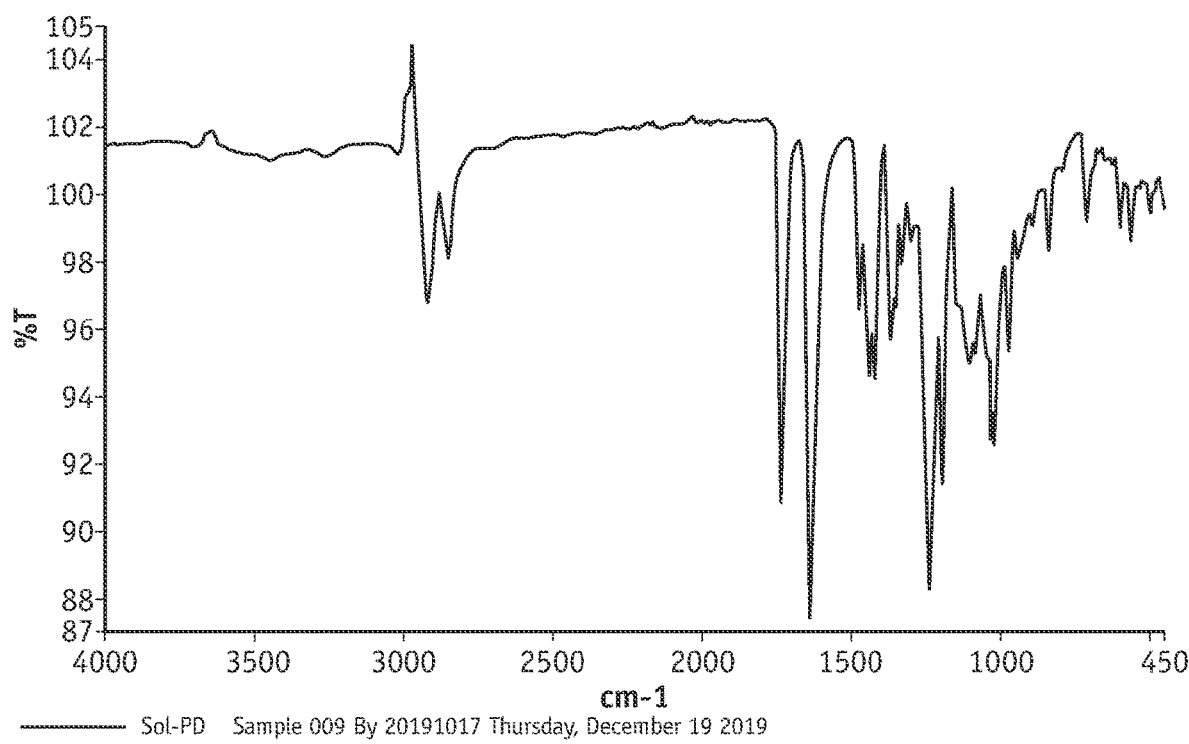
Figure 4C:
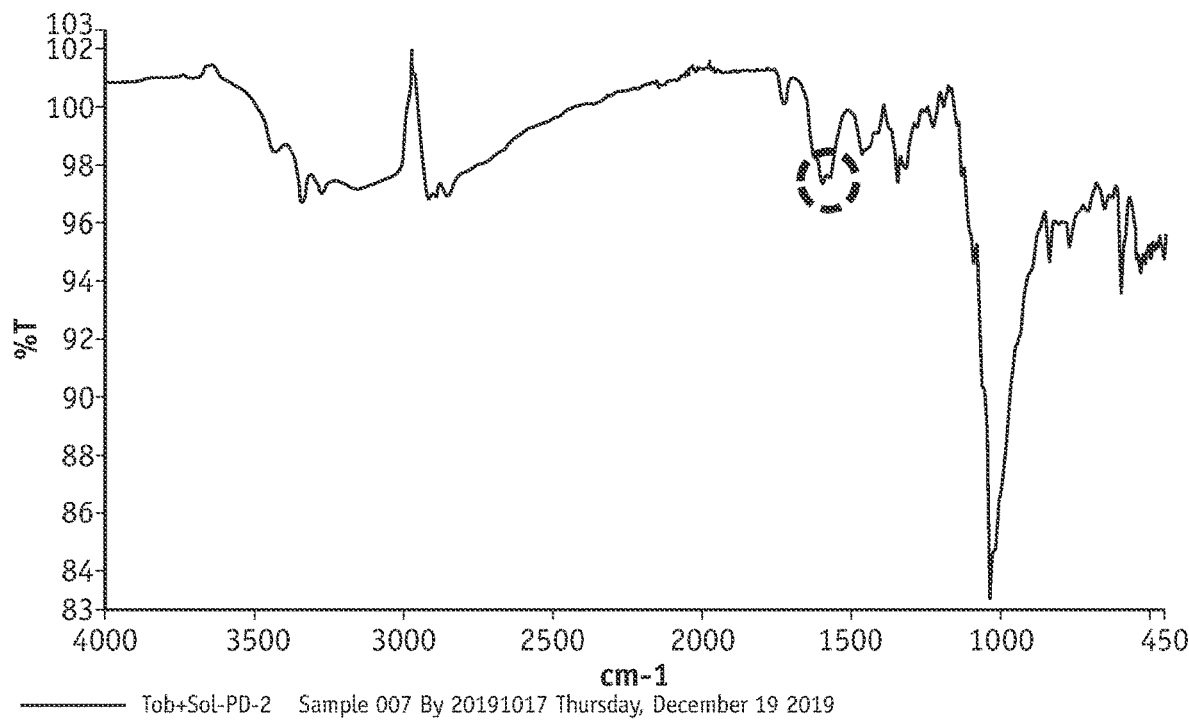

Tobramycin+histidine complexes and tobramycin+Soluplus® complexes were then analyzed by Fournier transform infrared (FTIR) to better understand the structure of the two complexes. This data is presented in FIGS. 2A and 2B (tobramycin alone and histidine alone, respectively) and 2C (tobramycin+histidine precipitated from solution), as well as FIGS. 4A and 4B (tobramycin alone and Soluplus® alone) and 4C (tobramycin+Soluplus® precipitated from solution).

The FTIR tobramycin and histidine complex analysis reveals that a new peak appears at 3016 cm-1. Further, N—H stretching in tobramycin is changed to 1567 cm-1. The peak for N—H and O—H bending is absent, while the C═O stretching for histidine is changed to 1632 cm-1, and the C═S stretching for histidine is changed to 1413 cm-1.

The FTIR tobramycin Soluplus® complex analysis results specifically reveal that a N—H stretching peak for tobramycin (1579 cm-1) is absent. The peak at 1633 cm-1 of Soluplus® changed to 1600 cm-1.

The FTIR and DSC data of this experiment combine to demonstrate the successful formation of both tobramycin+histidine and tobramycin+Soluplus® complexes. Generation of such complexes led to the planning of further experimentation to evaluate the ability of such complexes to increase the corneal permeability and retention of tobramycin, such an aim being indicative of the potential for successful development of a novel treatment for certain ophthalmic disorders such as infection having a reduced dosing frequency.

Example 2

A study was conducted to evaluate tobramycin+histidine and tobramycin+Soluplus® complexes for trans-corneal transport capability. The aim of this study was to determine whether the tobramycin in complex form was capable of increased corneal permeation and/or corneal retention over tobramycin alone.

The formulations as shown in table 4 were prepared for use in the trans-corneal transport evaluation experiment.

TABLE 4

Formulations of tobramycin and Soluplus ® for use in trans-corneal transport evaluation.

| Sr. No. | Tobramycin | Complexing Agent | NaCl conc. for osmolality adjustment | Osmolality (mOsm/Kg) | pH |
|---|---|---|---|---|---|
| 1 | 2.5% w/v | None | 0.47% w/v | 313 | 7.39 |
| 2 | 2.5% w/v | Histidine: 2.5% w/v | None | 325 | 7.4 |
| 3 | 2.5% w/v | Soluplus: 2.5% w/v | 0.40% w/v | 312 | 7.37 |

Steps for preparing the solutions described in Table 2 were as follows. To prepare the tobramycin 2.5% solution (used as a control), 2.5 g of tobramycin and 0.45 g of sodium chloride were weighed and dissolved in 50 mL of water, tobramycin being added and completely dissolved prior to the addition and complete dissolution of sodium chloride. The volume of the solution was then brought up to about 90 mL at which point the pH was adjusted to as close to 7.4 as possible using 0.1 N HCl or 0.1 N NaOH. The final solution volume was then brought up to 100 mL with water. To prepare the preparations of 2.5% tobramycin and 2.5% histidine or 2.5% Soluplus®, the same procedure was followed except 2.5 g of histidine or 2.5 g of Soluplus® was weighed in place of 0.45 g of sodium chloride. All other procedural steps remained the same.

The trans-corneal transport study of the tobramycin+histidine and tobramycin+Soluplus® complexes, with tobramycin alone as the control, was conducted across human corneal cells. The study was conducted in 24 well plates with N=6. The study comprised two parts: a first permeability assessment and a second retention assessment.

Results from the permeability assessment are shown in Table 5 below, with the permeability graphs of the three samples plotted and depicted in FIG. 5. In FIG. 5, tobramycin alone is shown in the graph with a square indicator; tobramycin+Histidine is shown with a circle-shaped indicator; and tobramycin+Soluplus® is shown with a triangular indicator.

TABLE 5

Transport of tobramycin across cultured human cornea from three different formulations including tobramycin + histidine and tobramycin + Soluplus ® complexes compared to non-complexed tobramycin.

| Time point (min) | Tobramycin (2.5%) + sodium chloride (0.47%) (ppm) | Tobramycin (2.5%) + Histidine (2.5%) (ppm) | Tobramycin (2.5%) + Soluplus (2.5%) (ppm) |
|---|---|---|---|
| 15 | 2.9 | 2.8 | 2.7 |
| 30 | 6.0 | 6.6 | 8.0 |
| 60 | 11.0 | 14.1 | 15.4 |
| 120 | 34.1 | 32.2 | 43.3 |
| 180 | 39.2 | 46.9 | 52.2 |
| 360 | 172.0 | 211.8 | 252.0 |

The above data demonstrate that the permeation across human corneal cells of tobramycin complex solutions with either histidine or Soluplus® are each faster than a non-complexed tobramycin product, such as a currently marketed tobramycin product, comparable formulation comprising non-complexed tobramycin, or both.

For the retention assessment, the concentration of tobramycin in donor chambers of the three solutions was measured, at the end of the experiment at time point 6 hours (360 minutes). The data collected is shown in graphical form as FIG. 6, with the raw data shown below in Table 6.

TABLE 6

Human corneal cell permeability of tobramycin + histidine and tobramycin + Soluplus ® complexes compared to non-complexed tobramycin.

| Formulation | Conc at 360 mins in donor (mg/mL) | Conc diff from initial (mg/mL) |
|---|---|---|
| Tobramycin (2.5%) + sodium chloride (0.47%) | 19.4 | 5.7 |
| Tobramycin (2.5%) + Histidine (2.5%) | 17.5 | 7.5 |

TABLE 6-continued

Human corneal cell permeability of tobramycin + histidine and tobramycin + Soluplus ® complexes compared to non-complexed tobramycin.

| Formulation | Conc at 360 mins in donor (mg/mL) | Conc diff from initial (mg/mL) |
|---|---|---|
| Tobramycin (2.5%) + Soluplus (2.5%) + Sodium chloride (0.40%) | 19.4 | 5.6 |

Based on the data depicted in FIG. 6, it is clear that the donor chamber concentration of the tobramycin+histidine complex is depleting rapidly and only a small amount appears in the receiving chamber. Most of the tobramycin taken up from the donor solution is being retained by cornea. This retention forms a depot of tobramycin in the cornea and is likely to get released in front of the eye over a period. This result is indicative of the ability to reduce the dosing frequency when utilizing a formulation comprising such a composition.

It should be understood that the above description and incorporated examples are intended to be illustrative and not restrictive. Many embodiments will be apparent to those of skill in the art upon reading the above description. The scope of the invention should, therefore, be determined with reference to the appended aspects and/or claims, along with the full scope of equivalents to which such claims are entitled. The disclosures of all articles and references, including patents, patent applications and publications, are incorporated herein by reference in their entirety and for all purposes.

Example 3

A study was conducted to evaluate tobramycin+histidine complexes in controlling infection of a mammalian eye, specifically a mammalian eye infected with *Staphylococcus Aureus* (S. Aureus).

Twelve healthy rabbits were selected using proper husbandry procedures. All rabbits were anesthetized by instilling proparacaine eye drops in both eyes. Rabbits were then injected with 50 µL suspension of *Staphylococcus Aureus* in trypticase soy broth (TSB) at a concentration of 10,000 CFU/mL, the injections being applied to each rabbit eye intra-stromally. The S. *Aureus* infection was allowed to grow in rabbit eyes for 12 hours.

After 12 hours, the rabbits were divided into two groups of six (6) rabbits. At 12 hours post administration of the infective agent, the first group of rabbits was dosed with a formulation ("reference") of tobramycin (similar to or the same as the marketed formulation TOBREX®) in their right eye. The second group of rabbits was dosed with the test formulation ("test") of Tobramycin 0.3% in their right eye. The left eye of each rabbit received a drop of saline. At 24 hours post first administration of the infective agent, a second dose of "reference" formulation, and a second dose of "test" formulation (tobramycin (0.3%)) were again administered to the right eye of each respective test group. The formulations of reference and test solutions are shown below in Table 7 and Table 8.

TABLE 7

Reference Formulation

| Sr. No. | Ingredients | Qty/mL |
|---|---|---|
| 1 | Tobramycin | 3.0 mg |
| 2 | BKC as 10% Soln. | 0.1 mg |
| 3 | Boric Acid | 12.4 mg |
| 4 | Sodium Sulfate | 1.52 mg |
| 5 | Tyloxapol | 1.0 mg |
| 6 | Sodium Chloride | 2.78 |
| 7 | Sodium Hydroxide | QS, pH adjust |
| 8 | Sulfuric acid | QS, pH adjust |
| 9 | Water of Injection | QS, 1 mL |

TABLE 8

Test Formulation Comprising 0.3% Tobramycin/0.3% Histidine

| Sr. No. | Ingredients | Qty/mL |
|---|---|---|
| 1 | Tobramycin | 3 mg |
| 2 | Histidine | 3 mg |
| 3 | Sodium Chloride | 7.48 mg |
| 4 | Sodium Hydroxide | QS, pH adjust |
| 5 | Sulfuric acid | QS, pH adjust |
| 6 | Water for Injection | QS, 1 mL |

At 25 hours post administration of the first dose of infective agent (1 hour post administration of the second dose of infective agent), tear samples were collected using sterile tear strips. Tear strips were then placed in 1.0 mL of TSB solution. 0.25 mL of the resulting solution was plated onto TS agar plates. Bacterial colonies were enumerated following overnight incubation at 37° C. Bacterial densities were estimated at $Log_{10}$ CFU/mL of tear.

Figure 7:
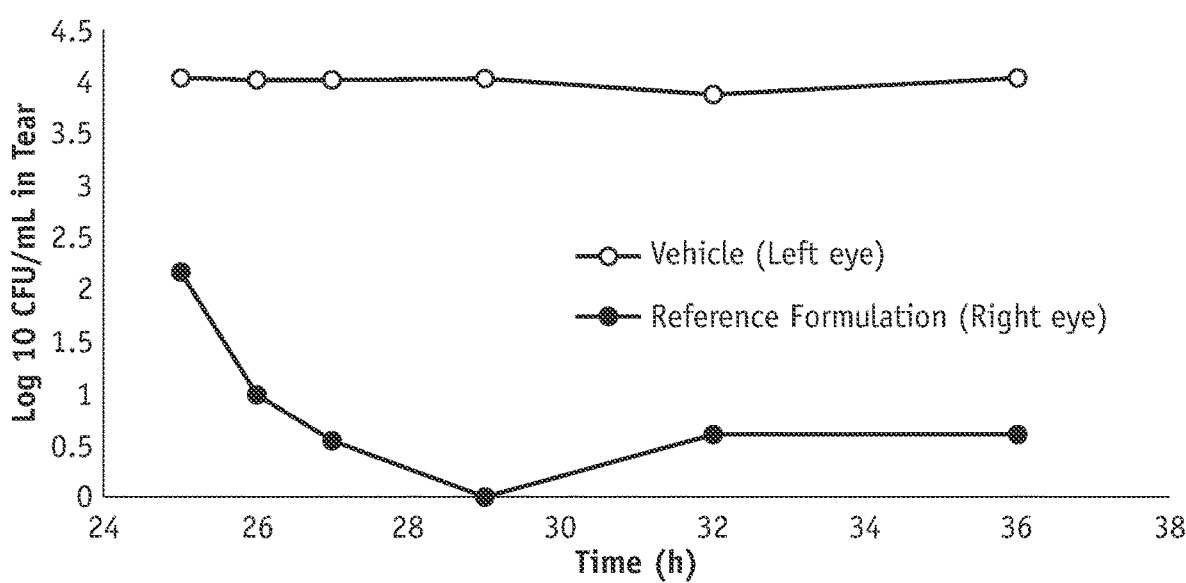
FIG. 7 is a graph of the number of S. *Aureus* colony forming units (CFUs) in tear sample(s) after 2 doses of a reference formulation versus vehicle.
Figure 8:
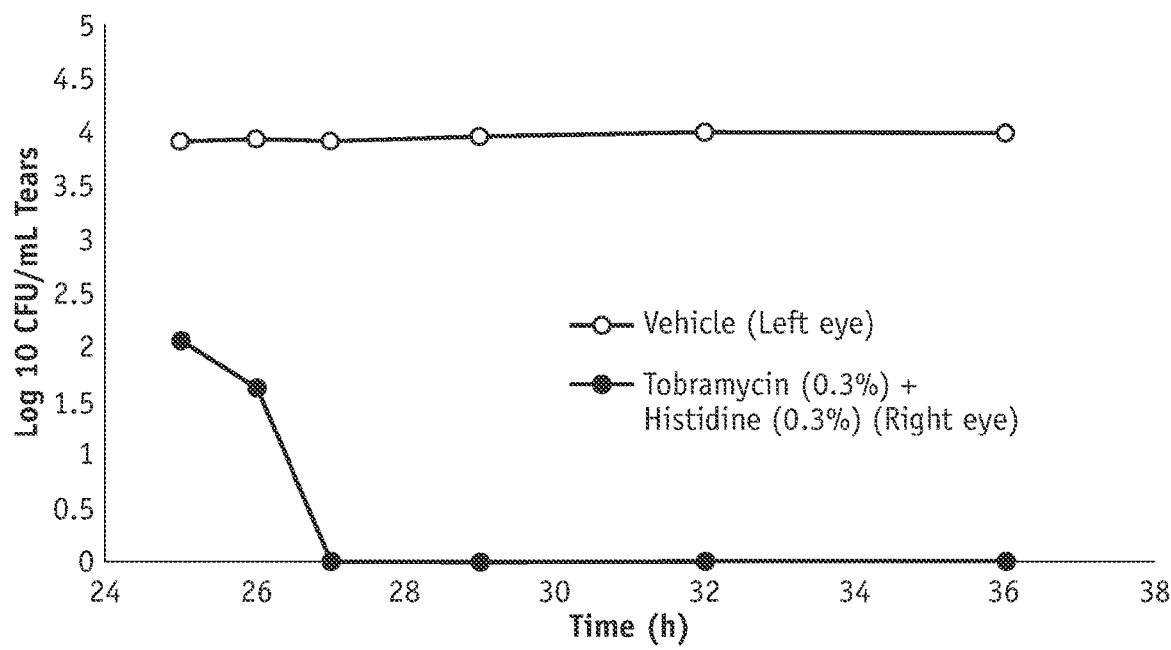
FIG. 8 is a graph of the number of S. *Aureus* colony forming units (CFUs) in tear sample(s) after 2 doses of tobramycin (0.3%)+histidine (0.3%) versus vehicle.

Colony forming unit (CFU) data is provided in FIG. 7. FIG. 7 shows colony forming units (CFU)s present in the tear sample(s) after 2 doses of reference formulation (again, similar TOBREX® (0.3%), marketed formulation) in the right eye compared to the vehicle (absent the API) in the left eye. Again, the first dose was given after 12 hours of initial infection of *Staphylococcus Aureus* and the second dose was given after 24 hours of the infection. The first tear sample was collected at 25 hours after the first dose (1 hour after the second dose). As shown, CFUs counts drop when reference formulation is instilled in the eye. However, notably, the bacterial count grows back (increases); see the upward trend line starting at between 28- and 30-hours post-administration in FIG. 7. In comparison, see FIG. 8. FIG. 8 illustrates CFUs present in tear sample after 2 doses of tobramycin (0.3%)+histidine (0.3%) formulation in the right eye compared to the vehicle (absent API) in the left eye. Again, the first dose was administered after 12 hours of initial infection of *Staphylococcus Aureus* and the second dose was administered at 24 hours post-infection. The first tear sample was collected at 25 hours post-initial infection, or 1 hour after the second dose. As shown in FIG. 8, when tobramycin (0.3%) formulation with histidine (test formulation) is instilled, the CFU count drops a bit more quickly. See the steeper trend from time point 24 hours to time point about 17 hours in FIG. 8 versus FIG. 7). Further, the CFU count does not then grow back (increase). This indicates that the histidine-containing formulation creates a small depot in the cornea, from which that active gets released, or is being released into the eye at a later time, in any case preventing further growth.

Of particular note is that the reference product contains benzalkonium chloride (BKC). Benzalkonium chloride is absent in the test formulation comprising histidine. It is well known in the art that BKC can aid in reducing bacterial load. In this study, the histidine containing formulation outperformed the formulation containing BKC.

Example 4

Similar studies to those exemplified in Example 3 were performed using different bacteria, *Pseudomonas Aeruginosa*. In this Example, the infection was allowed to grow for 24 hours prior to the first administration of reference product or test formulation. A first treatment was instilled at 24 hours post-infection and a second dose was administered at 36 hours post-infection. The reference formulation and first test formulation tested in this study were the same as those presented in Example 3. This study further included the testing of a second test formulation, this formulation comprising tobramycin+histidine in higher concentrations. This second test formulation is shown in Table 11 below. Other than requiring additional animals, the test protocol was otherwise similar to Example 3. The first tear samples were collected at 37 house post-infection, or 1 hour after administration of the second dose of treatment.

TABLE 11

Test Formulation Comprising 0.6% Tobramycin/0.6% Histidine

| Sr. No. | Ingredients | Qty/mL |
|---|---|---|
| 1 | Tobramycin | 6.0 mg |
| 2 | Histidine | 6.0 mg |
| 3 | Sodium Chloride | 6.24 mg |
| 4 | Sodium Hydroxide | QS, pH adjust |
| 5 | Sulfuric acid | QS, pH adjust |
| 6 | Water for Injection | QS, 1 mL |

Figure 9:
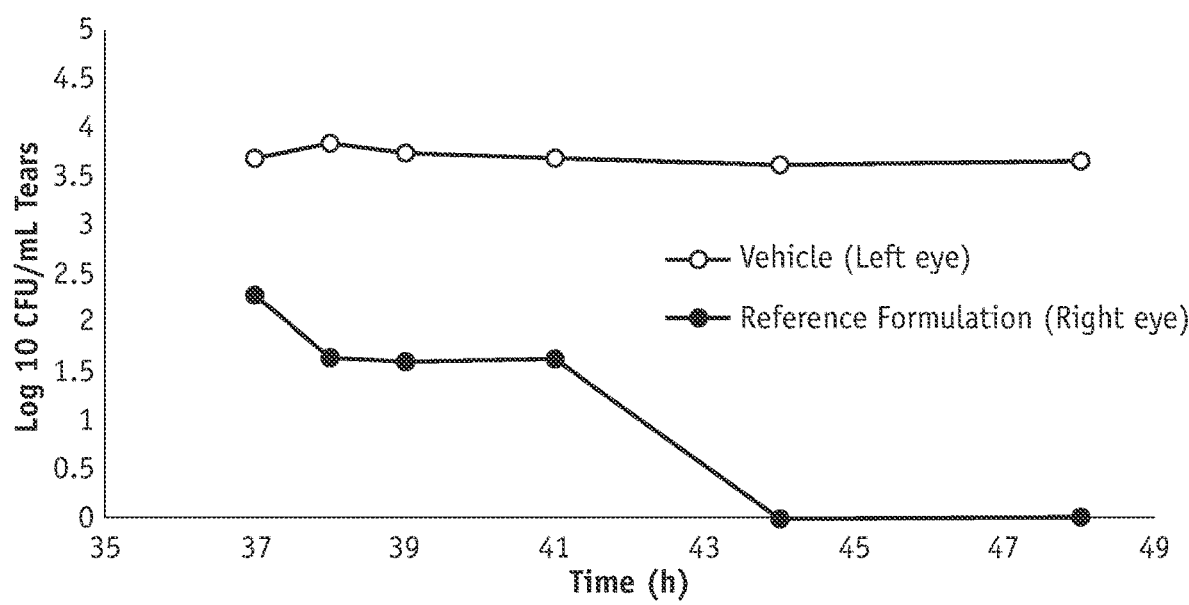
FIG. 9 is a graph of the number of P. *Aeruginosa* colony forming units (CFUs) in tear sample(s) after 2 doses of reference formulation versus vehicle.
Figure 10:
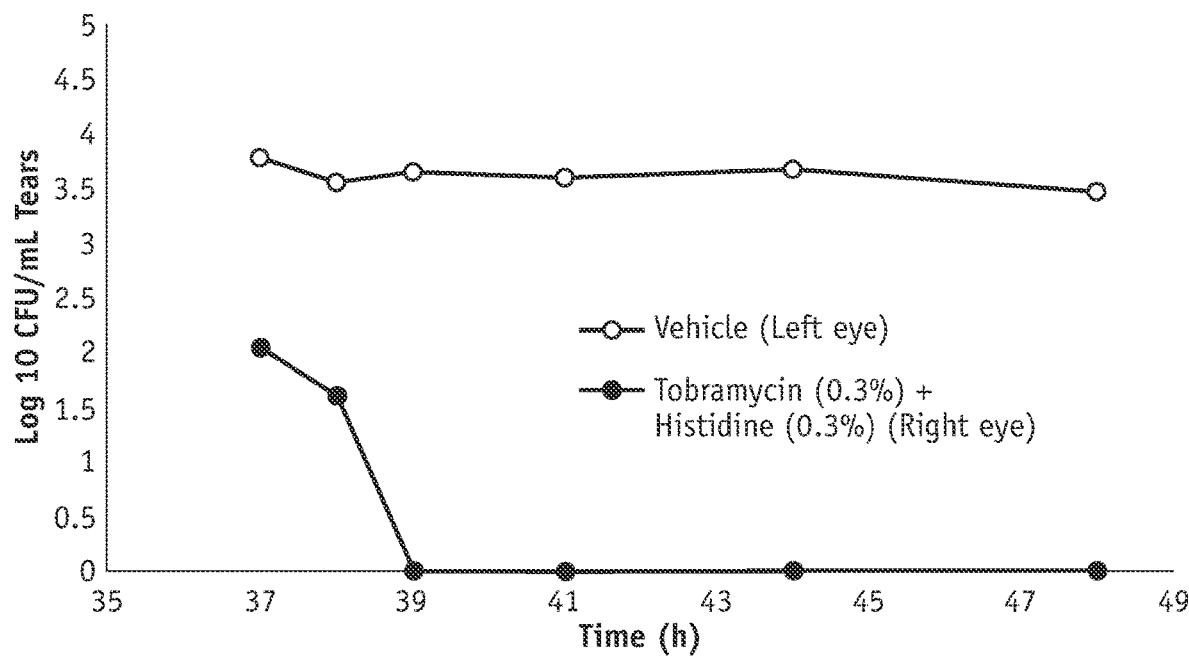
FIG. 10 is a graph of the number of P. *Aeruginosa* colony forming units (CFUs) in tear sample(s) after 2 doses of tobramycin (0.3%)+histidine (0.3%) versus vehicle.
Figure 11:
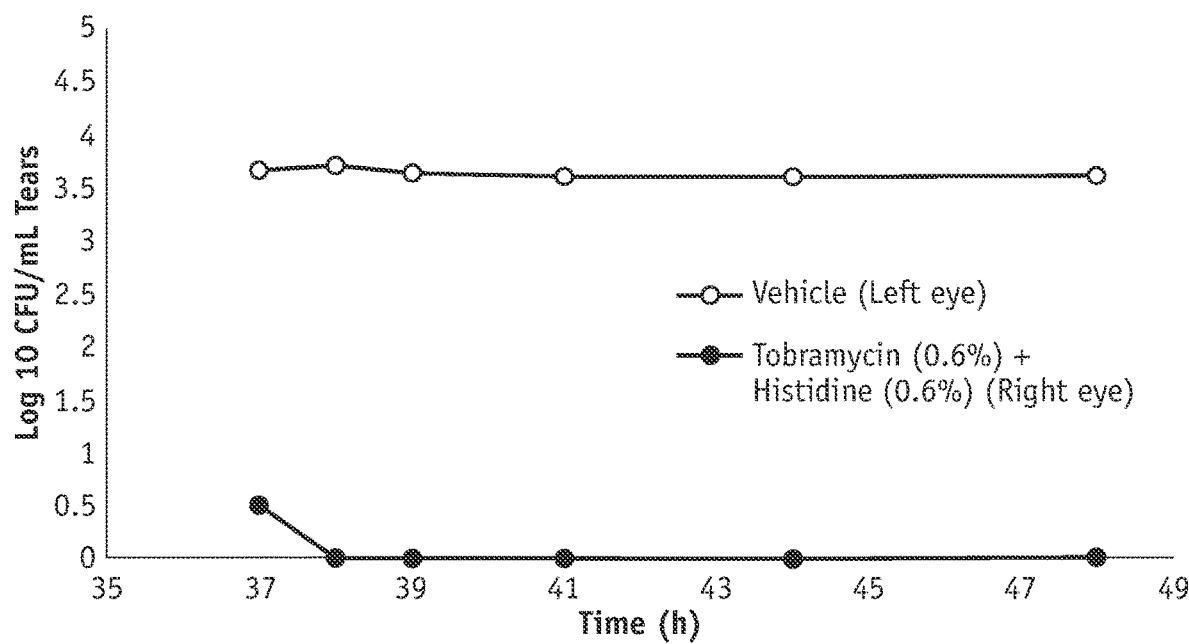
FIG. 11 is a graph of the number of P. *Aeruginosa* colony forming units (CFUs) in tear sample(s) after 2 doses of tobramycin (0.6%)+histidine (0.6%) versus vehicle.

FIG. 9 presents the CFUs present in the tear sample(s) after the 2 doses of reference formulation (once again, similar to the marketed formulation of TOBREX® (0.3%)) in the right eye compared to vehicle (formulation absent API) in the left eye. FIG. 10 presents the CFUs present in tear sample after 2 doses of tobramycin (0.3%)+histidine (0.3%) formulation in the right eye compared to the vehicle (formulation absent API) in the left eye. FIG. 11 presents the CFUs present in tear sample after 2 doses of tobramycin (0.6%)+histidine (0.6%) formulation in the right eye compared to the vehicle in the left eye.

As demonstrated by comparing FIGS. 9 and 10, the first test formulation (Tobramycin (0.3%)+Histidine (0.3%)) reduced the number of CFUs about 5 hours faster than that of the reference formulation. As demonstrated by comparing FIGS. 9 and 11, the second test formulation (Tobramycin (0.6%)+Histidine (0.6%)) reduced the number of CFUs about 6 hours faster than that of the reference formulation.

The results of this study demonstrate that both test formulations outperformed the reference formulation in the amount of time required to demonstrate a significant reduction (e.g., a reduction to 0 or non-detectable CFU/mL tears) in levels of infective agent present in collected tear solutions. Further, both test formulations were capable of maintaining the reduced level of infective agents through the time period studied.

Exemplary Aspects of the Invention

The following is a first set of non-limiting, exemplary aspects of the invention, which is intended to highlight some of the various embodiments of the invention.

In aspects, the invention comprises an ophthalmic tobramycin complex for instillation in the eye comprising tobramycin complexed with material that is suitable for ophthalmic use (aspect 1).

In aspects, the invention comprises the ophthalmic tobramycin complex of aspect 1, wherein the material suitable for ophthalmic use comprises histidine or polyvinyl caprolactam-polyvinyl acetate-polyethylene glycol graft copolymer (PCL-PVAc-PEG) or its derivatives (aspect 2).

In aspects, the invention comprises the ophthalmic tobramycin complex of aspect 1 or aspect 2, wherein the amount of tobramycin and material that is suitable for ophthalmic use in the complex is about 1.0% to about 10% by weight (aspect 3).

In aspects, the invention comprises the ophthalmic tobramycin complex of any one or more of aspects 1-3, wherein the tobramycin complex is formulated as solution, suspension, emulsion, or a dispersion (aspect 4).

In aspects, the invention comprises the ophthalmic tobramycin complex of aspect 4, wherein the tobramycin complex is formulated as an ophthalmic solution (aspect 5).

In aspects, the invention comprises the ophthalmic solution of aspect 5, wherein the solution is applied once, twice, or three times daily (aspect 6).

In aspects, the invention comprises the ophthalmic solution of aspect 5 or aspect 6, wherein the instillation of solution in the eye allows to reduce the daily dosage frequency, improves compliance, duration and effect of tobramycin for the treatment of external infections of the eye and its adnexa caused by susceptible bacteria (aspect 7).

In aspects, the invention is a method of treating an infection of the eye or its adnexa comprising topically administering to the eye a solution composition comprising tobramycin complexed with histidine or PCL-PVAc-PEG or its derivatives, wherein the solution composition allows for efficacy in treating the infection with a once, twice or three times per day dosing schedule (aspect 8).

In aspects, the invention comprises the method of treating infections of the eye or its adnexa of aspect 8, wherein the tobramycin is complexed with histidine (aspect 9).

In aspects, the invention comprises the method of treating infections of the eye or its adnexa of aspect 8, wherein the tobramycin is complexed with PCL-PVAc-PEG or its derivatives (aspect 10).

In aspects, the invention comprises the method of treating infections of the eye or its adnexa of any one or more of aspects 8-10, wherein the amount of tobramycin is about 0.3% to about 5.0% by weight (aspect 11).

In aspects, the invention comprises the method of treating infections of the eye or its adnexa of aspect 11, wherein the amount of tobramycin is about 2.5% to about 5.0% by weight (aspect 12).

In aspects, the invention comprises the method of treating infections of the eye or its adnexa of any one or more of aspects 8-12, wherein the amount of histidine or PCL-PVAc-PEG or its derivatives is about 1.0% to about 10% by weight (aspect 13).

In aspects, the invention comprises the method for treating infections of the eye or its adnexa of aspect 13, wherein the amount of histidine or PCL-PVAc-PEG or its derivatives is about 2.5% to about 5.0% by weight (aspect 14).

In aspects, the invention is an ophthalmic tobramycin formulation comprising tobramycin complexed with histidine or PCL-PVAc-PEG or its derivatives, wherein the dosage form of the ophthalmic tobramycin formulation retains at least 90% w/w of the potency of tobramycin when stored at 25° C. and 60% relative humidity or at 40° C. and 75% relative humidity for 3 months (aspect 15).

In aspects, the invention is a pharmaceutical composition comprising an antimicrobial active pharmaceutical ingredient (API) comprising an effective amount of a compound having a structure according to the formula

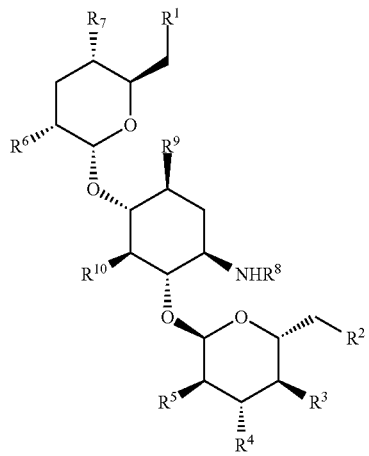

wherein (1) $R^1$ is —CH—$NH_2$ (i.e., Me—$NH_2$) or an optionally substituted alkyl, an optionally substituted aryl, an optionally substituted aralkyl, an optionally substituted cycloalkyl, an optionally substituted cycloalkylalkyl, an optionally substituted heterocyclyl, an optionally substituted heterocyclylalkyl, an optionally substituted heteroaryl, or an optionally substituted heteroarylalkyl; (2) $R^4$, $R^6$, $R^8$, and $R^9$ are —$NH_2$ or an optionally substituted alkyl, an optionally substituted aryl, an optionally substituted aralkyl, an optionally substituted cycloalkyl, an optionally substituted cycloalkylalkyl, an optionally substituted heterocyclyl, an optionally substituted heterocyclylalkyl, an optionally substituted heteroaryl, or an optionally substituted heteroarylalkyl; (3) $R^2$ is —Me—OH or an optionally substituted alkyl, an optionally substituted aryl, an optionally substituted aralkyl, an optionally substituted cycloalkyl, an optionally substituted cycloalkylalkyl, an optionally substituted heterocyclyl, an optionally substituted heterocyclylalkyl, an optionally substituted heteroaryl, or an optionally substituted heteroarylalkyl; and (4) $R^3$, $R^5$, $R^7$ and $R^{10}$ are —OH or an optionally substituted aryl, an optionally substituted aralkyl, an optionally substituted cycloalkyl, an optionally substituted cycloalkylalkyl, an optionally substituted heterocyclyl, an optionally substituted heterocyclylalkyl, an optionally substituted heteroaryl, or an optionally substituted heteroarylalkyl (Formula I); complexed with a lipophilic and amphoteric complexing agent, wherein the composition is ophthalmologically safe and the complexing agent detectably promotes the uptake of the composition by corneal cells, the retention of the complex by corneal cells, or both, as compared to the free compound (aspect 16).

In aspects, the invention is the pharmaceutical composition of aspect 16, wherein no more than three of $R^1$, $R^2$, $R^3$, $R^4$, $R^5$, $R^6$, $R^7$, $R^8$, $R^9$, and $R^{10}$ differ in composition from the corresponding position in tobramycin (aspect 17).

In aspects, the invention is the pharmaceutical composition of aspect 17, wherein no more than two of $R^1$, $R^2$, $R^3$, $R^4$, $R^5$, $R^6$, $R^7$, $R^8$, $R^9$, and $R^{10}$ differ from the corresponding position in tobramycin (aspect 18).

In aspects, the invention is the pharmaceutical composition of aspect 18, wherein no more than one of $R^1$, $R^2$, $R^3$, $R^4$, $R^5$, $R^6$, $R^7$, $R^8$, $R^9$, and $R^{10}$ differs from the corresponding position in tobramycin (aspect 19).

In aspects, the invention is the pharmaceutical composition of aspect 16, wherein the compound has a structure according to Formula II (aspect 20).

In aspects, the invention is the pharmaceutical composition of aspect 20, wherein no more than three of $R^1$, $R^2$, $R^3$, $R^4$, $R^5$, $R^6$, $R^7$, and $R^8$ differ from the corresponding position in tobramycin (aspect 21).

In aspects, the invention is the pharmaceutical composition of aspect 20, wherein no more than two of $R^1$, $R^2$, $R^3$, $R^4$, $R^5$, $R^6$, $R^7$, and $R^8$ differ from the corresponding position in tobramycin (aspect 22).

In aspects, the invention is the pharmaceutical composition of aspect 22, wherein no more than one of $R^1$, $R^2$, $R^3$, $R^4$, $R^5$, $R^6$, $R^7$, and $R^8$ differ from the corresponding position in tobramycin (aspect 23).

In aspects, the invention is the pharmaceutical composition of any one or more of aspects 20-22, wherein $R^2$, $R^7$, or both are the same as the corresponding positions in tobramycin (aspect 24).

In aspects, the invention is the pharmaceutical composition of aspect 24, wherein $R^2$ is a —Me—Oh and $R^7$ is an —OH (i.e., these positions have the same composition as the corresponding positions in tobramycin) (aspect 25).

In aspects, the invention is the pharmaceutical composition of aspect 20, wherein the compound has a structure according to Formula III (aspect 26).

In aspects, the invention is the pharmaceutical composition of any one or more of aspects 16-26, wherein any R group that differs from tobramycin includes an optionally derivatized 2-20 atom backbone alkyl or heteroalkyl group, optionally attached through an ester or amide bond at a position corresponding to an —OH or —NH$_2$ group in tobramycin (aspect 27).

In aspects, the invention is the pharmaceutical composition of aspect 27, wherein the alkyl or heteroalkyl group is a linear alkyl or heteroalkyl compound (aspect 28).

In aspects, the invention is the pharmaceutical composition of aspect 28, wherein the group is or generally consists of a fatty acid, fatty acid derivative, short fatty acid, or short fatty acid derivative (aspect 29).

In aspects, the invention is the pharmaceutical composition of aspect 29, wherein the group is or generally consists of an acetic acid, acetic acid derivative, palmitic acid, or palmitic acid derivative (aspect 30).

In aspects, the invention is the pharmaceutical composition of aspect 30, wherein the alkyl or heteroalkyl group comprises one or more —C═O or —NH$_2$ derivative groups bound to the backbone (aspect 31).

In aspects, the invention is the pharmaceutical composition of aspect 31, wherein the group comprises at least one —C═O group and at least one —NH$_2$ group bound to the backbone (aspect 32).

In aspects, the invention is the pharmaceutical composition of aspect 28, wherein the group comprises no —C═O groups (aspect 33).

In aspects, the invention is the pharmaceutical composition of any one or more of aspects 31-33, wherein the group comprises at least two —NH$_2$ groups bound to the backbone (aspect 34).

In aspects, the invention is the pharmaceutical composition of any one or more of aspects 27-34, wherein the backbone of the group is a heteroalkyl structure comprising at least one nitrogen, at least one thiol/sulfur, or both (aspect 35).

In aspects, the invention is the pharmaceutical composition of any one or more of aspects 27-35, wherein at least about 90% of the atoms of the backbone are carbons (aspect 36).

In aspects, the invention is the pharmaceutical composition of any one or more of aspects 27-36, wherein the backbone comprises or is bound to an optionally derivatized 3-9-membered cycloalkyl or heterocycloalkyl ring (aspect 37).

In aspects, the invention is the pharmaceutical composition of aspect 37, wherein the backbone comprises or is bound to a 3-6 membered ring wherein the ring comprises one or more nitro groups, is bound to one or more nitro groups, or is bound to one or more side chains bound to one or more nitro groups (aspect 38).

In aspects, the invention is the pharmaceutical composition of aspect 37 or aspect 38, wherein the group comprises only one ring (aspect 39).

In aspects, the invention is the pharmaceutical composition of any one or more of aspects 16-39, wherein the compound is a tobramycin derivative (aspect 40).

In aspects, the invention is the pharmaceutical composition of aspect 40, wherein the tobramycin derivative exhibits detectably faster penetration of corneal cells than tobramycin, detectably better retention in corneal cells than tobramycin, or both (aspect 41).

In aspects, the invention is the pharmaceutical composition of aspect 26, wherein the compound is tobramycin (aspect 42).

In aspects, the invention is the pharmaceutical composition of any one or more of aspects 16-42, wherein the complexing agent is a heterocyclic compound comprising at least one five to seven-member nitrogenous ring comprising an attached chain of at least 3 carbons and at least one carboxylic acid group (aspect 43).

In aspects, the invention is the pharmaceutical composition of aspect 43, wherein the complexing agent is an amino acid (aspect 44).

In aspects, the invention is the pharmaceutical composition of aspect 44, wherein the complexing agent is histidine (aspect 45).

In aspects, the invention is the pharmaceutical composition of aspect 44, wherein the complexing agent is an ophthalmologically acceptable derivative of histidine (aspect 46).

In aspects, the invention is the pharmaceutical composition of aspect 43, wherein the complexing agent is an ophthalmologically safe copolymer (aspect 47).

In aspects, the invention is the pharmaceutical composition of aspect 47, wherein the complexing agent is polyvinyl caprolactam-polyvinyl acetate-polyethylene glycol graft co-polymer (PCL-PVAc-PEG) (aspect 48).

In aspects, the invention is the pharmaceutical composition of aspect 47, wherein the complexing agent is a derivative of PCL-PVAc-PEG (aspect 49).

In aspects, the invention is the pharmaceutical composition of any one or more of aspects 16-49, wherein the composition is present within a formulation, and the compound is present in a concentration of between about 0.1-about 10% w/v (aspect 50).

In aspects, the invention is the pharmaceutical composition of aspect 50, wherein the composition is present within the formulation, and the compound is present in a concentration of between about 0.3-about 5% w/v (aspect 51).

In aspects, the invention is the pharmaceutical composition of aspect 51, wherein the composition is present within the formulation, and the compound is present in a concentration of between about 0.6-about 5% w/v (aspect 52).

In aspects, the invention is the pharmaceutical composition of aspect 52, wherein the composition is present within the formulation, and the compound is present in a concentration of between about 1 and about 3% w/v (aspect 53).

In aspects, the invention is the pharmaceutical composition of aspect 53, wherein the composition is present within the formulation, and the compound is present in a concentration of approximately 2.5% w/v (aspect 54).

In aspects, the invention is the pharmaceutical composition of any one or more of aspects 50-54, wherein the complexing agent is present within the formulation at a concentration of between about 0.1% and about 10% w/v (aspect 55).

In aspects, the invention is the pharmaceutical composition of aspect 55, wherein the complexing agent is present within the formulation at a concentration of between about 0.3-5% w/v (aspect 56).

In aspects, the invention is the pharmaceutical composition of aspect 56, wherein the complexing agent is present within the formulation at a concentration of between about 0.6-5% w/v (aspect 57).

In aspects, the invention is the pharmaceutical composition of aspect 57, wherein the complexing agent is present within the formulation at a concentration of between about 1-3% (aspect 58).

In aspects, the invention is the pharmaceutical composition of aspect 58, wherein the complexing agent is present within the formulation at a concentration of approximately 2.5% (aspect 59).

In aspects, the invention is the pharmaceutical composition of any one or more of aspects 16-59, wherein the rate of cornea cell permeation is faster for the compound in complexed form than the non-complexed compound, such that the amount of compound in the cornea increases by at least about 15% or more after a period of 60 minutes from administration (aspect 60).

In aspects, the invention is the pharmaceutical composition of aspect 60, wherein the concentration of compound permeating the surface of the cornea is at least 17% greater when in complexed form than in non-complexed form when measured at 360 minutes of an industry-standard corneal permeability assay (aspect 61).

In aspects, the invention is the pharmaceutical composition of aspect 61, wherein the concentration of compound permeating the surface of the cornea is at least 20% greater when in complexed form than in non-complexed form when measured at 360 minutes of an industry-standard corneal permeability assay (aspect 62).

In aspects, the invention is the pharmaceutical composition of aspect 62, wherein the concentration of compound permeating the surface of the cornea is at least 25% greater when in complexed form than in non-complexed form when measured at 360 minutes of an industry-standard corneal permeability assay (aspect 63).

In aspects, the invention is the pharmaceutical composition of aspect 63, wherein the concentration of compound permeating the surface of the cornea is at least 40% greater when in complexed form than in non-complexed form when measured at 360 minutes of an industry-standard corneal permeability assay (aspect 64).

In aspects, the invention is the pharmaceutical composition of aspect 64, wherein the concentration of compound permeating the surface of the cornea is at least 45% greater when in complexed form than in non-complexed form when measured at 360 minutes of an industry-standard corneal permeability assay (aspect 65).

In aspects, the invention is the pharmaceutical composition of any one or more of aspects 60-65, wherein the concentration of compound permeating the surface of the cornea is at least about 15% or greater after 15 minutes from application than a corresponding amount of the API in TOBREX® (aspect 66).

In aspects, the invention is the pharmaceutical composition of any one or more of aspects 60-66, wherein the complexing agent is histidine (aspect 67).

In aspects, the invention is the pharmaceutical composition of any one or more of aspects 60-66, wherein the complexing agent is PCL-PVAc-PEG (aspect 68).

In aspects, the invention is the pharmaceutical composition of any one or more of aspects 60-68, wherein the onset of symptom improvement is detectably faster than that of the non-complexed compound, as assessed by a qualified professional or as self-reported in an appropriately controlled study of a patient population (aspect 69).

In aspects, the invention is the pharmaceutical composition of any one or more of aspects 60-69, wherein a single course of administration of a treatment comprising the composition resolves the condition for which the course of administration is prescribed at least about 5% more frequently than a single course of administration of a treatment comprising a similar composition comprising a non-complexed compound as measured by an appropriately controlled clinical trial or by post-market monitoring and reporting (aspect 70).

In aspects, the invention is the pharmaceutical composition of any one or more of aspects 60-70, wherein the composition requires an administration rate of no more than two-thirds of the total number of doses required for a similar composition comprising a non-complexed compound over the same course of treatment (aspect 71).

In aspects, the invention is the pharmaceutical composition of aspect 71, wherein the composition requires an administration rate of no more than one-half of the total number of doses required for a similar composition comprising a non-complexed compound over the same course of treatment (aspect 72).

In aspects, the invention is the pharmaceutical composition of aspect 72, wherein the composition requires an administration rate of no more than one-third of the total number of doses required for a similar composition comprising a non-complexed compound over the same course of treatment (aspect 73).

In aspects, the invention is the pharmaceutical composition of any one or more of aspects 16-73, wherein the level of retention of the complexed compound in the cornea is retained after 6 hours from administration when measured by an industry-standard corneal retention assay (aspect 74).

In aspects, the invention is the pharmaceutical composition of any one or more of aspects 16-74, wherein the retention of the complexed compound within the cornea is at least 15% higher than the retention of the non-complexed compound when measured at 360 minutes as measured by a standard corneal retention assay (aspect 75).

In aspects, the invention is the pharmaceutical composition of aspect 75, wherein the retention of the complexed compound within the cornea is at least 20% higher than the retention of the non-complexed compound when measured at 360 minutes as measured by a standard corneal retention assay (aspect 76).

In aspects, the invention is the pharmaceutical composition of aspect 76, wherein the retention of the complexed compound within the cornea is at least 25% higher than the retention of the non-complexed compound when measured at 360 minutes as measured by a standard corneal retention assay (aspect 77).

In aspects, the invention is the pharmaceutical composition of aspect 77, wherein the retention of the complexed compound within the cornea is at least 30% higher than the retention of the non-complexed compound when measured at 360 minutes as measured by a standard corneal retention assay (aspect 78).

In aspects, the invention is the pharmaceutical composition of any one or more of aspects 74-78, wherein the compound is retained in at least about 15% or greater amount in corneal cells after 15 minutes than a corresponding amount of the API in TOBREX® (aspect 79).

In aspects, the invention is the pharmaceutical composition of any one or more of aspects 74-79, wherein the complexing agent is histidine (aspect 80).

In aspects, the invention is the pharmaceutical composition of any one or more of aspects 74-80, wherein the onset of symptom improvement is at least detectably faster than that of a similar composition comprising a non-complexed compound, as assessed by a qualified professional or as self-reported in an appropriately controlled assessment of a patient population (aspect 81).

In aspects, the invention is the pharmaceutical composition of any one or more of aspects 74-81, wherein a single course of administration of a treatment comprising the composition resolves the condition for which the course of administration is prescribed at least 5% more frequently than a single course of administration of a treatment comprising a similar composition with a non-complexed compound as measured by an appropriately controlled clinical trial (aspect 82).

In aspects, the invention is the pharmaceutical composition of any one or more of aspects 74-82, wherein the composition requires an administration rate of no more than two-thirds of the total number of doses required for a similar composition comprising a non-complexed compound over the same course of treatment (aspect 83).

In aspects, the invention is the pharmaceutical composition of aspect 83, wherein the composition requires an administration rate of no more than one half of the total number of doses required for a similar composition comprising a non-complexed compound over the same course of treatment (aspect 84).

In aspects, the invention is the pharmaceutical composition of aspect 84, wherein the composition requires an administration rate of no more than one-third of the total number of doses required for a similar composition comprising a non-complexed compound over the same course of treatment (aspect 85).

In aspects, the invention is the pharmaceutical composition of any one or more of aspects 74-85, wherein the rate of antibiotic resistance in a population receiving the composition is significantly less than the rate of antibiotic resistance in a population having received a similar composition comprising a non-complexed compound (aspect 86).

In aspects, the invention is the pharmaceutical composition of any one or more of aspects 16-86, wherein both the concentration of compound permeating the surface of the cornea is at least 17% greater when in complexed form than in non-complexed form when measured at 360 minutes of an industry-standard corneal permeability assay, and the retention of the complexed compound within the cornea as measured by a standard corneal retention assay is at least 25% higher than the retention of the compound in non-complexed form (aspect 87).

In aspects, the invention is the pharmaceutical composition of aspect 87, wherein the complexing agent is a heterocyclic compound comprising at least one five-to-seven-member nitrogenous ring comprising an attached chain of at least 3 carbons and at least one carboxylic acid group (aspect 88).

In aspects, the invention is the pharmaceutical composition of aspect 88, wherein the complexing agent is an amino acid (aspect 89).

In aspects, the invention is the pharmaceutical composition of aspect 89, wherein the complexing agent is histidine (aspect 90).

In aspects, the invention is the pharmaceutical composition of any one or more of aspects 87-90, wherein the onset of symptom improvement is at least detectably faster than that of a similar composition comprising a non-complexed compound, as assessed by a qualified professional or as self-reported in an appropriately controlled assessment of a patient population (aspect 91).

In aspects, the invention is the pharmaceutical composition of any one or more of aspects 87-91, wherein a single course of administration of a treatment comprising the composition resolves the condition for which the course of administration is prescribed at least 5% more frequently than a single course of administration of a treatment comprising a similar composition with a non-complexed compound as measured by an appropriately controlled clinical trial (aspect 92).

In aspects, the invention is the pharmaceutical composition of any one or more of aspects 87-92, wherein the composition requires an administration rate of no more than two-thirds of the total number of doses required for a similar composition comprising a non-complexed compound over the same course of treatment (aspect 93).

In aspects, the invention is the pharmaceutical composition of aspect 93, wherein the composition requires an administration rate of no more than one half of the total number of doses required for a similar composition comprising a non-complexed compound over the same course of treatment (aspect 94).

In aspects, the invention is the pharmaceutical composition of aspect 94, wherein the composition requires an administration rate of no more than one-third of the total number of doses required for a similar composition comprising a non-complexed compound over the same course of treatment (aspect 95).

In aspects, the invention is the pharmaceutical composition of any one or more of aspects 87-95, wherein the rate of antibiotic resistance in a population receiving the composition is significantly less than in a population having received a similar composition comprising a non-complexed compound (aspect 96).

In aspects, the invention is the pharmaceutical composition of any one or more of paragraphs aspects 60-67; aspects 69-79; aspects 81-89; and aspects 91-96, wherein the complexing agent is an ophthalmologically safe derivative of histidine having both a lipophilic and amphoteric nature (aspect 97).

In aspects, the invention is the pharmaceutical composition of any one or more of aspects 60-87 or aspects 91-97, wherein the complexing agent is an ophthalmologically safe derivative of PCL-PVAc-PEG having both a lipophilic and amphoteric nature (aspect 98).

In aspects, the invention is a method of treating an ocular disease or condition with a composition comprising a pharmaceutically active ingredient (API) comprising a compound having a structure according to:

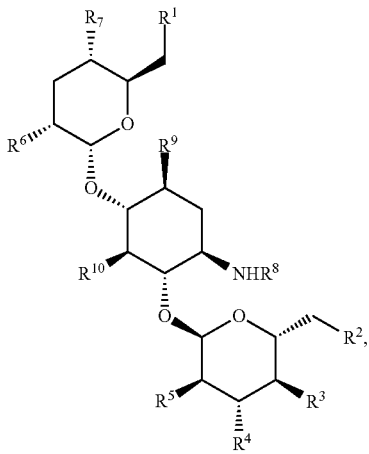

wherein (1) $R^1$ is —CH—$NH_2$ (i.e., Me—$NH_2$) or an optionally substituted alkyl, an optionally substituted aryl, an optionally substituted aralkyl, an optionally substituted cycloalkyl, an optionally substituted cycloalkylalkyl, an optionally substituted heterocyclyl, an optionally substituted heterocyclylalkyl, an optionally substituted heteroaryl, or an optionally substituted heteroarylalkyl; (2) $R^4$, $R^6$, $R^8$, and $R^9$ are —$NH_2$ or an optionally substituted alkyl, an optionally substituted aryl, an optionally substituted aralkyl, an optionally substituted cycloalkyl, an optionally substituted cycloalkylalkyl, an optionally substituted heterocyclyl, an optionally substituted heterocyclylalkyl, an optionally substituted heteroaryl, or an optionally substituted heteroarylalkyl; (3) $R^2$ is —Me—OH or an optionally substituted alkyl, an optionally substituted aryl, an optionally substituted aralkyl, an optionally substituted cycloalkyl, an optionally substituted cycloalkylalkyl, an optionally substituted heterocyclyl, an optionally substituted heterocyclylalkyl, an optionally substituted heteroaryl, or an optionally substituted heteroarylalkyl; and (4) $R^3$, $R^5$, $R^7$ and $R^{10}$ are —OH or an optionally substituted aryl, an optionally substituted aralkyl, an optionally substituted cycloalkyl, an optionally substituted cycloalkylalkyl, an optionally substituted heterocyclyl, an optionally substituted heterocyclylalkyl, an optionally substituted heteroaryl, or an optionally substituted heteroarylalkyl (Formula I); wherein the compound is not tobramycin and wherein the compound is lipophilic and amphoteric in nature and further wherein the composition is ophthalmologically safe detectably and wherein the presence of any of the R groups of (1)-(4) promotes the uptake of the composition by corneal cells, the retention of the composition by corneal cells, or both, as compared to tobramycin (aspect 99).

In aspects, the invention is the method of aspects 99, wherein the compound is a derivative of tobramycin (aspect 100).

In aspects, the invention is the method of aspect 100, wherein the derivatization of tobramycin occurs by (alternatively stated, any R group that differs from tobramycin is different from tobramycin by) substituting a 2-20 atom backbone alkyl or heteroalkyl group, through an ester or amide bond at a position corresponding to an —OH or —$NH_2$ group in tobramycin (aspect 101).

In aspects, the invention is the method of aspect 101, wherein the alkyl or heteroalkyl group is a linear alkyl or heteroalkyl compound (aspect 102).

In aspects, the invention is the method of aspect 102, wherein the group generally consists of a fatty acid, a fatty acid derivative, a short fatty acid, or a short fatty acid derivative (aspect 103).

In aspects, the invention is the method of aspect 103, wherein the group generally consists of acetic acid, an acetic acid derivative, palmitic acid, or a palmitic acid derivative (aspect 104).

In aspects, the invention is the method of aspect 102, wherein the alkyl or heteroalkyl group comprises one or more —C=O or —$NH_2$ derivative groups bound to the backbone (aspect 105).

In aspects, the invention is the method of aspect 105, wherein the group comprises at least one —C=O group and at least one —$NH_2$ group bound to the backbone (aspect 106).

In aspects, the invention is the method of aspect 102, wherein the group comprises no —C=O groups (aspect 107).

In aspects, the invention is the method of any one or more of aspects 105-107, wherein the group comprises at least two —$NH_2$ groups bound to the backbone (aspect 108).

In aspects, the invention is the method of any one or more of aspects 101-108, wherein the backbone of the group is a heteroalkyl structure comprising at least one nitrogen, at least one thiol/sulfur, or both (aspect 109).

In aspects, the invention is the method of any one or more of aspects 101-109, wherein at least about 90% of the atoms of the backbone are carbons (aspect 110).

In aspects, the invention is the method of any one or more of aspects 101-110, wherein the backbone comprises or is bound to an optionally derivatized 3-9-membered cycloalkyl or heterocycloalkyl ring (aspect 111).

In aspects, the invention is the method of aspect 111, wherein the backbone comprises or is bound to a 3-6 membered ring wherein the ring comprises one or more nitro groups, is bound to one or more nitro groups, or is bound to one or more side chains bound to one or more nitro groups (aspect 112).

In aspects, the invention is the method of aspect 111 or aspect 112, wherein the group comprises only one ring (aspect 113).

In aspects, the invention is the method of aspect 113, wherein the tobramycin derivative exhibits detectably faster penetration of corneal cells than tobramycin, detectably better retention in corneal cells than tobramycin, or both (aspect 114).

In aspects, the invention is the method of any one or more of aspects 99-114, wherein the compound is complexed with a lipophilic and amphoteric, complexing agent (aspect 115).

In aspects, the invention is the method of aspect 115, wherein the complexing agent detectably increases the permeability, retention, or both permeability and retention of the compound across and/or within corneal cells (aspect 116).

In aspects, the invention is the method of aspect 115 or aspect 116, wherein the complexing agent is a heterocyclic compound comprising at least one five-to-seven-member nitrogenous ring comprising an attached chain of at least 3 carbons and at least one carboxylic acid group (aspect 117).

In aspects, the invention is the method of aspect 117, wherein the complexing agent is an amino acid (aspect 118).

In aspects, the invention is the method of aspect 118, wherein the complexing agent is histidine (aspect 119).

In aspects, the invention is the method of aspect 118, wherein the complexing agent is an ophthalmologically acceptable derivative of histidine having both a lipophilic and amphoteric nature (aspect 120).

In aspects, the invention is the method of aspect 117, wherein the complexing agent is a copolymer (aspect 121).

In aspects, the invention is the method of aspect 121, wherein the complexing agent is PCL-PVAc-PEG (aspect 122).

In aspects, the invention is the method of aspect 121, wherein the complexing agent is an ophthalmologically safe derivative of PCL-PVAc-PEG having both a lipophilic and amphoteric nature (aspect 123).

In aspects, the invention is the method of any one or more of aspects 99-123, wherein the composition is present within a formulation, and the concentration of the compound in the formulation is between about 0.1-about 10% w/v (aspect 124).

In aspects, the invention is the method of aspect 124, wherein the composition is present within a formulation, and the concentration of the compound in the formulation is between about 0.3-about 5% w/v (aspect 125).

In aspects, the invention is the method of aspect 125, wherein the composition is present within a formulation, and the concentration of the compound in the formulation is between about 0.6-about 5% w/v (aspect 126).

In aspects, the invention is the method of aspect 126, wherein the composition is present within a formulation, and the concentration of the compound in the formulation is between about 1 and about 3% w/v (aspect 127).

In aspects, the invention is the method of aspect 127, wherein the composition is present within a formulation and the concentration of the compound in the formulation approximately 2.5% w/v (aspect 128).

In aspects, the invention is the method of any one or more of aspects 124-128, wherein if the formulation comprises a complexing agent, the complexing agent is present in the formulation in a concentration ranging from 0.1-10% w/v (aspect 129).

In aspects, the invention is the method of any one or more of aspects 99-129, wherein the rate of cornea cell penetration of the compound is faster than that of tobramycin such that the amount of compound in the cornea increases by at least about 15% or more after a period of 360 minutes from administration of a similar composition comprising tobramycin (aspect 130).

In aspects, the invention is the method of aspect 130, wherein the concentration of compound permeating the surface of the cornea is at least 17% greater than tobramycin when measured at 360 minutes of an industry-standard corneal permeability assay (aspect 131).

In aspects, the invention is the method of aspect 131, wherein the concentration of compound permeating the surface of the cornea is at least 20% greater than tobramycin when measured at 360 minutes of an industry-standard corneal permeability assay (aspect 132).

In aspects, the invention is the method of aspect 132, wherein the concentration of compound permeating the surface of the cornea is at least 25% greater than tobramycin when measured at 360 minutes of an industry-standard corneal permeability assay (aspect 133).

In aspects, the invention is the method of aspect 133, wherein the concentration of compound permeating the surface of the cornea is at least 40% greater than tobramycin when measured at 360 minutes of an industry-standard corneal permeability assay (aspect 134).

In aspects, the invention is the method of aspect 134, wherein the concentration of compound permeating the surface of the cornea is at least 45% greater than tobramycin when measured at 360 minutes of an industry-standard corneal permeability assay (aspect 135).

In aspects, the invention is the method of any one or more of aspects 99-135, wherein the level of retention of the compound within the cornea is retained after 6 hours from administration when measured at 360 minutes as measured by a standard corneal retention assay (aspect 136).

In aspects, the invention is the method of any one or more of aspects 99-136, wherein the compound is retained in at least about 15% or greater amount in corneal cells after 15 minutes than a corresponding amount of the API in TOBREX® (aspect 137).

In aspects, the invention is the method aspect 137, wherein the retention of the compound within the cornea as measured by a standard corneal retention assay is at least 15% higher than the retention of tobramycin (aspect 138).

In aspects, the invention is the method of aspect 138, wherein the retention of the compound within the cornea is at least 17% higher than the retention of tobramycin when measured at 360 minutes as measured by a standard corneal retention assay (aspect 139).

In aspects, the invention is the method of aspect 139, wherein the retention of the compound within the cornea is at least 20% higher than the retention of tobramycin when measured at 360 minutes as measured by a standard corneal retention assay (aspect 140).

In aspects, the invention is the method of aspect 140, wherein the retention of the compound within the cornea is at least 25% higher than the retention of tobramycin when measured at 360 minutes as measured by a standard corneal retention assay (aspect 141).

In aspects, the invention is the method of aspect 141, wherein the retention of the compound within the cornea is at least 30% higher than the retention of tobramycin when measured at 360 minutes as measured by a standard corneal retention assay (aspect 142).

In aspects, the invention is the method of aspect 142, wherein the retention of the derivatized compound within the cornea is at least 32% higher than the retention of tobramycin when measured at 360 minutes as measured by a standard corneal retention assay (aspect 143).

In aspects, the invention is the method of any one or more of aspects 99-143, wherein administration of a formulation comprising the composition results in the onset of symptom improvement is significantly faster than that of a similar composition comprising tobramycin, as assessed by a qualified professional or as self-reported in an appropriately controlled assessment of a patient population (aspect 144).

In aspects, the invention is the method of any one or more of aspects 99-144, wherein a single course of administration of a treatment comprising the composition resolves the condition for which the course of administration is prescribed at least 5% more frequently than a single course of administration of a treatment comprising a similar composition with tobramycin as measured by an appropriately controlled clinical trial (aspect 145).

In aspects, the invention is the method of any one or more of aspects 99-145, wherein the administration protocol of a formulation comprising the composition requires an administration rate of no more than two-thirds of the total number of doses required for a similar composition comprising tobramycin over the same course of treatment (aspect 146).

In aspects, the invention is the method of aspect 146, wherein the administration protocol of a formulation comprising the composition requires an administration rate of no more than one-half of the total number of doses required for a similar composition comprising tobramycin over the same course of treatment (aspect 147).

In aspects, the invention is the method of aspect 147, wherein the administration protocol of a formulation comprising the composition requires an administration rate of no more than one-third of the total number of doses required for a similar composition comprising tobramycin over the same course of treatment (aspect 148).

In aspects, the invention is the method of any one or more of aspects 99-148, wherein the rate of antibiotic resistance in a population receiving the composition is significantly less than the rate of antibiotic resistance in a population having received a similar composition comprising tobramycin (aspect 149).

In aspects, the invention is a pharmaceutical formulation comprising an active pharmaceutical agent according to any one or more of aspects 16-49, wherein the compound is tobramycin, and wherein the formulation comprises an effective amount of one or additional delivery agents selected from a liposome(s), a microsphere(s), or both, which is amphoteric, lipophilic, and suitable for ophthalmologic applications, wherein the compound is retained in at least about 15% greater amount in corneal cells after 15 minutes than a corresponding amount of the compound when no additional delivery agent is present (aspect 150).

In aspects, the invention is the pharmaceutical formulation of aspect 150, wherein the presence of the one or more additional delivery agents significantly enhances the permeation, retention, or both permeation of retention of the compound across and/or within corneal cells compared to a similar formulation comprising no additional delivery agents (aspect 151).

In aspects, the invention is the pharmaceutical formulation of any one or more of aspects 150-151, wherein the formulation further comprises one or more excipients (aspect 152).

In aspects, the invention is the pharmaceutical formulation of aspect 152, wherein the one or more excipients is selected from the group comprising one or more of a viscosity-enhancer, osmotic modification agent, surfactant, chelating agent, tonicity agent, buffer, pH-adjusting agent, a preservative, or water (aspect 153).

In aspects, the invention is the pharmaceutical formulation of aspect 153, wherein at least one excipient is a viscosity-enhancing excipient (aspect 154).

In aspects, the invention is the pharmaceutical formulation of aspect 154, wherein the viscosity of the formulation is between about 10 cps and about 400 cps (aspect 155).

In aspects, the invention is the pharmaceutical formulation of aspect 155, wherein the formulation has a viscosity of about 25 cps to about 300 cps (aspect 156).

In aspects, the invention is the pharmaceutical formulation of any one or more of aspects 154-156, wherein the viscosity is at least 5% higher than the viscosity of a similar composition which does not comprise a viscosity-enhancing agent (aspect 157).

In aspects, the invention is the pharmaceutical formulation of any one or more of aspects 150-157, wherein the compound is present in the formulation in a concentration of between about 0.1-about 10% w/v (aspect 158).

In aspects, the invention is the pharmaceutical formulation of aspect 158, wherein the compound is present within the formulation in a concentration of between about 0.3-about 5% w/v (aspect 159).

In aspects, the invention is the pharmaceutical formulation of aspect 159, wherein the compound is present within the formulation in a concentration of between about 0.6-about 5% w/v (aspect 160).

In aspects, the invention is the pharmaceutical formulation of aspect 160, wherein the compound is present within the formulation in a concentration of between about 1 and about 3% w/v (aspect 161).

In aspects, the invention is the pharmaceutical formulation of aspect 161, wherein the compound is present within the formulation in a concentration of approximately 2.5% w/v (aspect 162).

In aspects, the invention is the pharmaceutical formulation of any one or more of aspects 158-162, wherein the complexing agent is present within the formulation in a concentration of between about 0.1-about 10% w/v (aspect 163).

In aspects, the invention is the pharmaceutical formulation of aspect 163, wherein the complexing agent is present within the formulation in a concentration of between about 0.3-5% w/v (aspect 164).

In aspects, the invention is the pharmaceutical formulation of aspect 164, wherein the complexing agent is present within the formulation in a concentration of between about 1-5% w/v (aspect 165).

In aspects, the invention is the pharmaceutical formulation of aspect 165, wherein the complexing agent is present within the formulation in a concentration of approximately 2.5% w/v (aspect 166).

In aspects, the invention is a pharmaceutical formulation comprising a composition comprising a pharmaceutically active ingredient (API) comprising a compound having a structure according to

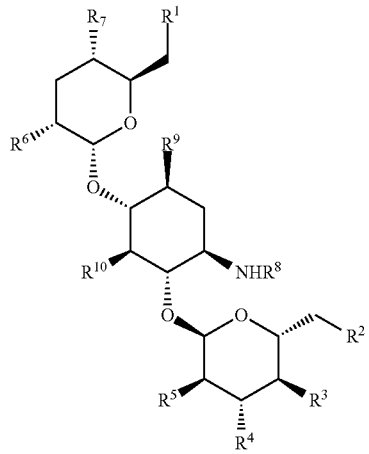

wherein (1) $R^1$ is —CH—$NH_2$ (i.e., Me—$NH_2$) or an optionally substituted alkyl, an optionally substituted aryl, an optionally substituted aralkyl, an optionally substituted cycloalkyl, an optionally substituted cycloalkylalkyl, an optionally substituted heterocyclyl, an optionally substituted heterocyclylalkyl, an optionally substituted heteroaryl, or an optionally substituted heteroarylalkyl; (2) $R^4$, $R^6$, $R^8$, and $R^9$ are —$NH_2$ or an optionally substituted alkyl, an optionally substituted aryl, an optionally substituted aralkyl, an optionally substituted cycloalkyl, an optionally substituted cycloalkylalkyl, an optionally substituted heterocyclyl, an optionally substituted heterocyclylalkyl, an optionally substituted heteroaryl, or an optionally substituted heteroarylalkyl; (3) $R^2$ is —Me—OH or an optionally substituted alkyl, an optionally substituted aryl, an optionally substituted aralkyl, an optionally substituted cycloalkyl, an optionally substituted cycloalkylalkyl, an optionally substituted heterocyclyl, an optionally substituted heterocyclylalkyl, an optionally substituted heteroaryl, or an optionally substituted heteroarylalkyl; and (4) $R^3$, $R^5$, $R^7$ and $R^{10}$ are —OH or an optionally substituted aryl, an optionally substituted aralkyl, an optionally substituted cycloalkyl, an optionally substituted cycloalkylalkyl, an optionally substituted heterocyclyl, an optionally substituted heterocyclylalkyl, an optionally substituted heteroaryl, or an optionally substituted heteroarylalkyl (Formula I); wherein the compound is not tobramycin and wherein the compound is lipophilic and amphoteric in nature and further wherein the composition is ophthalmologically safe detectably and wherein the presence of any of the R groups of (1)-(4) promotes the uptake of the composition by corneal cells, the retention of the composition by corneal cells, or both, as compared to tobramycin, and further wherein the formulation comprises an effective amount of one or additional delivery agents selected from a liposome(s), a microsphere(s), or both, which is amphoteric, lipophilic, and suitable for ophthalmologic applications, wherein the compound is retained in at least about 15% greater amount in corneal cells after 15 minutes than a corresponding amount of the compound when no additional delivery agent is present (aspect 167).

In aspects, the invention is the pharmaceutical formulation of aspect 167, wherein the derivatization of tobramycin occurs by (alternatively stated, any R group that differs from tobramycin is different from tobramycin by) substituting a 2-20 atom backbone alkyl or heteroalkyl group, through an ester or amide bond at a position corresponding to an —OH or —$NH_2$ group in tobramycin (aspect 168).

In aspects, the invention is the pharmaceutical formulation of aspect 168, wherein the alkyl or heteroalkyl group is a linear alkyl or heteroalkyl compound (aspect 169).

In aspects, the invention is the pharmaceutical formulation of aspect 169, wherein the group generally consists of a fatty acid, a fatty acid derivative, a short fatty acid, or a short fatty acid derivative (aspect 170).

In aspects, the invention is the pharmaceutical formulation of aspect 170, wherein the group generally consists of acetic acid, an acetic acid derivative, palmitic acid, or a palmitic acid derivative (aspect 171).

In aspects, the invention is the pharmaceutical formulation of aspect 171, wherein the alkyl or heteroalkyl group comprises one or more —C=O or —$NH_2$ derivative groups bound to the backbone (aspect 172).

In aspects, the invention is the pharmaceutical formulation of aspect 172, wherein the group comprises at least one —C=O group and at least one —$NH_2$ group bound to the backbone (aspect 173).

In aspects, the invention is the pharmaceutical formulation of aspect 173, wherein the group comprises no —C=O groups (aspect 174).

In aspects, the invention is the pharmaceutical formulation of any one or more of aspects 172-174, wherein the group comprises at least two —$NH_2$ groups bound to the backbone (aspect 175).

In aspects, the invention is the pharmaceutical formulation of any one or more of aspects 168-175, wherein the backbone of the group is a heteroalkyl structure comprising at least one nitrogen, at least one thiol/sulfur, or both (aspect 176).

In aspects, the invention is the pharmaceutical formulation of any one or more of aspects 170-176, wherein at least about 90% of the atoms of the backbone are carbons (aspect 177).

In aspects, the invention is the pharmaceutical formulation of any one or more of aspects 169-177, wherein the backbone comprises or is bound to an optionally derivatized 3-9-membered cycloalkyl or heterocycloalkyl ring (aspect 178).

In aspects, the invention is the pharmaceutical formulation of aspect 178, wherein the backbone comprises or is bound to a 3-6 membered ring wherein the ring comprises one or more nitro groups, is bound to one or more nitro groups, or is bound to one or more side chains bound to one or more nitro groups (aspect 179).

In aspects, the invention is the pharmaceutical formulation of aspect 178 or aspect 179, wherein the group comprises only one ring (aspect 180).

In aspects, the invention is the pharmaceutical formulation of aspect 180, wherein the tobramycin derivative exhibits detectably faster penetration of corneal cells than tobramycin, detectably better retention in corneal cells than tobramycin, or both (aspect 181).

In aspects, the invention is the pharmaceutical formulation of any one or more of aspects 167-181, wherein the compound is complexed with a lipophilic and amphoteric, complexing agent (aspect 182).

In aspects, the invention is the pharmaceutical formulation of aspect 182, wherein the complexing agent detectably increases the permeability, retention, or both permeability and retention of the compound across and/or within corneal cells (aspect 183).

In aspects, the invention is the pharmaceutical formulation of any one or more of aspects 182-183, wherein the complexing agent is a heterocyclic compound comprising at least one five to seven member nitrogenous ring comprising an attached chain of at least 3 carbons and at least one carboxylic acid group (aspect 184).

In aspects, the invention is the pharmaceutical formulation of aspect 184, wherein the complexing agent is an amino acid (aspect 185).

In aspects, the invention is the pharmaceutical formulation of aspect 185, wherein the complexing agent is histidine (aspect 186).

In aspects, the invention is the pharmaceutical formulation of aspect 185, wherein the complexing agent is an ophthalmologically acceptable derivative of histidine having both a lipophilic and amphoteric nature (aspect 187).

In aspects, the invention is the pharmaceutical formulation of aspect 184, wherein the complexing agent is a copolymer (aspect 188).

In aspects, the invention is the pharmaceutical formulation of aspect 188, wherein the complexing agent is PCL-PVAc-PEG (aspect 189).

In aspects, the invention is the pharmaceutical formulation of aspect 188, wherein the complexing agent is an ophthalmologically safe derivative of PCL-PVAc-PEG having both a lipophilic and amphoteric nature (aspect 190).

In aspects, the invention is the pharmaceutical formulation of any one or more of aspects 167-190, wherein the presence of the one or more additional delivery agents significantly enhances the permeation, retention, or both permeation of retention of the compound across and/or within corneal cells compared to a similar formulation comprising no additional delivery agents (aspect 191).

In aspects, the invention is the pharmaceutical formulation of any one or more of aspects 167-191, wherein the formulation further comprises one or more excipients (aspect 192).

In aspects, the invention is the pharmaceutical formulation of aspect 192, wherein the one or more excipients is selected from the group comprising one or more of a viscosity-enhancer, osmotic modification agent, surfactant, chelating agent, tonicity agent, buffer, pH-adjusting agent, a preservative, or water (aspect 193).

In aspects, the invention is the pharmaceutical formulation of aspect 193, wherein at least one excipient is a viscosity-enhancing excipient (aspect 194).

In aspects, the invention is the pharmaceutical formulation of aspect 194, wherein the viscosity of the formulation is between about 10 cps and about 400 cps (aspect 195).

In aspects, the invention is the pharmaceutical formulation of aspect 195, wherein the formulation has a viscosity of about 25 cps to about 300 cps (aspect 196).

In aspects, the invention is the pharmaceutical formulation of any one or more of aspects 194-196, wherein the viscosity is at least 5% higher than the viscosity of a similar composition comprising the compound without the viscosity-enhancing agent (aspect 197).

In aspects, the invention is the pharmaceutical formulation of any one or more of aspects 167-197, wherein the compound is present in the formulation in a concentration of between about 0.1-about 10% w/v (aspect 198).

The pharmaceutical formulation of aspect 198, wherein the compound is present within the formulation in a concentration of between about 0.3-about 5% w/v (aspect 199).

In aspects, the invention is the pharmaceutical formulation of aspect 199, wherein the compound is present within the formulation in a concentration of between about 0.6-about 5% w/v (aspect 200).

In aspects, the invention is the pharmaceutical formulation of aspect 200, wherein the compound is present within the formulation in a concentration of between about 1 and about 3% w/v (aspect 201).

In aspects, the invention is the pharmaceutical formulation of aspect 201, wherein the compound is present within the formulation in a concentration of approximately 2.5% w/v (aspect 202).

In aspects, the invention is the pharmaceutical formulation of any one or more of aspects 198-202, wherein the complexing agent, when present, is present in the formulation in a concentration of between about 0.1-10% w/v (aspect 203).

In aspects, the invention is a pharmaceutical formulation comprising an antimicrobial active pharmaceutical ingredient (API) comprising an effective amount of a compound having a structure according to Formula I wherein (1) $R^1$ is —CH—$NH_2$ (i.e., Me—$NH_2$) or an optionally substituted alkyl, an optionally substituted aryl, an optionally substituted aralkyl, an optionally substituted cycloalkyl, an optionally substituted cycloalkylalkyl, an optionally substituted heterocyclyl, an optionally substituted heterocyclylalkyl, an optionally substituted heteroaryl, or an optionally substituted heteroarylalkyl; (2) $R^4$, $R^6$, $R^8$, and $R^9$ are —$NH_2$ or an optionally substituted alkyl, an optionally substituted aryl, an optionally substituted aralkyl, an optionally substituted cycloalkyl, an optionally substituted cycloalkylalkyl, an optionally substituted heterocyclyl, an optionally substituted heterocyclylalkyl, an optionally substituted heteroaryl, or an optionally substituted heteroarylalkyl; (3) $R^2$ is —Me—OH or an optionally substituted alkyl, an optionally substituted aryl, an optionally substituted aralkyl, an optionally substituted cycloalkyl, an optionally substituted cycloalkylalkyl, an optionally substituted heterocyclyl, an optionally substituted heterocyclylalkyl, an optionally substituted heteroaryl, or an optionally substituted heteroarylalkyl; and (4) $R^3$, $R^5$, $R^7$ and $R^{10}$ are —OH or an optionally substituted aryl, an optionally substituted aralkyl, an optionally substituted cycloalkyl, an optionally substituted cycloalkylalkyl, an optionally substituted heterocyclyl, an optionally substituted heterocyclylalkyl, an optionally substituted heteroaryl, or an optionally substituted heteroarylalkyl, and an effective amount of a liposome or microsphere delivery agent, which is amphoteric, lipophilic, and suitable for ophthalmologic applications, wherein the compound is retained in at least about 15% greater amount in corneal cells after 15 minutes than a corresponding amount of the compound when not present with the liposome or microsphere delivery agent (aspect 204).

In aspects, the invention is the pharmaceutical formulation of aspect 204, wherein the compound is not tobramycin (aspect 205).

In aspects, the invention is the pharmaceutical formulation of aspect 204, wherein the compound is tobramycin (aspect 206).

In aspects, the invention is the pharmaceutical formulation of any one or more of aspects 204-206, wherein the compound is complexed with a complexing agent comprising a heterocyclic compound comprising at least one five- to-seven-member nitrogenous ring comprising an attached chain of at least 3 carbons and at least one carboxylic acid group (aspect 207).

In aspects, the invention is the pharmaceutical formulation of aspect 207, wherein the complexing agent is an amino acid (aspect 208).

In aspects, the invention is the pharmaceutical formulation of aspect 208, wherein the complexing agent is histidine (aspect 209).

In aspects, the invention is the pharmaceutical formulation of aspect 208, wherein the complexing agent is an ophthalmologically acceptable derivative of histidine having both a lipophilic and amphoteric nature (aspect 210).

In aspects, the invention is the pharmaceutical formulation of aspect 207, wherein the complexing agent is a copolymer (aspect 211).

In aspects, the invention is the pharmaceutical formulation of aspect 211, wherein the complexing agent is PCL-PVAc-PEG (aspect 212).

In aspects, the invention is the pharmaceutical formulation of aspect 211, wherein the complexing agent is an ophthalmologically safe derivative of PCL-PVAc-PEG having both a lipophilic and amphoteric nature (aspect 213).

In aspects, the invention is the pharmaceutical formulation of any one or more of aspects 207-213, wherein the presence of the complexing agent significantly enhances the permeation, retention, or both permeation of retention of the compound across, within, or both across and/or within corneal cells compared to a similar formulation comprising no complexing agent (aspect 214).

In aspects, the invention is the pharmaceutical formulation of any one or more of aspects 202-214, wherein the formulation further comprises one or more excipients (aspect 215).

In aspects, the invention is the pharmaceutical formulation of aspect 215, wherein the one or more excipients is selected from the group comprising one or more of a viscosity-enhancer, osmotic modification agent, surfactant, chelating agent, tonicity agent, buffer, pH-adjusting agent, a preservative, or water (aspect 216).

In aspects, the invention is the pharmaceutical formulation of aspect 216, wherein at least one excipient is a viscosity-enhancing excipient (aspect 217).

In aspects, the invention is the pharmaceutical formulation of aspect 217, wherein the viscosity of the formulation is between about 10 cps and about 400 cps (aspect 218).

In aspects, the invention is the pharmaceutical formulation of aspect 218, wherein the formulation has a viscosity of about 25 cps to about 300 cps (aspect 219).

In aspects, the invention is the pharmaceutical formulation of any one or more of aspects 217-219, wherein the viscosity is at least 5% higher than the viscosity of a similar composition comprising no viscosity-enhancing agent (aspect 220).

In aspects, the invention is the pharmaceutical formulation of any one or more of aspects 204-220, wherein the compound is present in the formulation in a concentration of between about 0.1-about 10% w/v (aspect 221).

In aspects, the invention is the pharmaceutical formulation of aspect 221, wherein the compound is present within the formulation in a concentration of between about 0.3-about 5% w/v (aspect 222).

In aspects, the invention is the pharmaceutical formulation of aspect 222, wherein the compound is present within the formulation in a concentration of between about 0.6-about 5% w/v (aspect 223).

In aspects, the invention is the pharmaceutical formulation of aspect 223, wherein the compound is present within the formulation in a concentration of between about 1 and about 3% w/v (aspect 224).

In aspects, the invention is the pharmaceutical formulation of aspect 224, wherein the compound is present within the formulation in a concentration of approximately 2.5% w/v (aspect 225).

In aspects, the invention is the pharmaceutical formulation of any one or more of aspects 221-225, wherein the complexing agent, when present, is present in the formulation in a concentration of between about 0.1-10% w/v (aspect 226).

In aspects, the invention is the pharmaceutical formulation according to any one or more of aspects 150-226, wherein the compound is retained in at least about a 15% greater amount in corneal cells after 15 minutes than the API in TOBREX® as measured by a standard corneal cell retention assay (aspect 227).

In aspects, the invention is the pharmaceutical formulation of any one or more of aspects 150-227, wherein the formulation is delivered as a solution, emulsion, dispersion, or suspension (aspect 228).

In aspects, the invention is the pharmaceutical formulation of aspect 228, wherein the formulation is delivered as a solution (aspect 229).

In aspects, the invention is the pharmaceutical formulation of aspect 229, wherein the formulation is administered via drops to the eye (aspect 230).

In aspects, the invention is the pharmaceutical formulation of aspect 228, wherein the formulation is delivered as an ointment (aspect 231).

In aspects, the invention is the pharmaceutical formulation of aspect 231, wherein the formulation is administered by applying a strip of the ointment to the eye (aspect 232).

In aspects, the invention is the pharmaceutical formulation of any one or more of aspects 150-232, wherein the formulation maintains the compound in contact with the ocular surface (mucous membrane) of the eye for at least 2 hours after application (aspect 233).

In aspects, the invention is the pharmaceutical formulation of aspect 233, wherein the formulation maintains the active in contact with the ocular surface (mucous membrane) of the eye after applying for at least approximately 4 hours after application (aspect 234).

In aspects, the invention is the pharmaceutical formulation of aspect 234, wherein the formulation maintains the active in contact with the ocular surface (mucous membrane) of the eye after applying for at least approximately 8 hours after application (aspect 235).

In aspects, the invention is the pharmaceutical formulation of aspect 235, wherein the formulation maintains the active in contact with the ocular surface (mucous membrane) of the eye after applying for at least approximately 16 hours after application (aspect 236).

In aspects, the invention is the pharmaceutical formulation of aspect 236, wherein the formulation maintains the active in contact with the ocular surface (mucous membrane) of the eye after applying for at least approximately 20 hours after application (aspect 237).

In aspects, the invention is the pharmaceutical formulation of aspect 237, wherein the formulation maintains the active in contact with the ocular surface (mucous membrane) of the eye after applying for at least approximately 24 hours after application (aspect 238).

In aspects, the invention is the pharmaceutical formulation of any one or more of aspects 150-238, wherein the formulations demonstrate at least 5% higher patient compliance as compared to TOBREX® as assessed by one or more physicians in an appropriately powered population of patients, by self-reported patient survey in an appropriately powered study, or by an appropriately powered clinical study (aspect 239).

In aspects, the invention is the pharmaceutical formulation of any one or more of aspects 150-239, wherein the formulations demonstrate at least 5% better efficacy as compared to TOBREX® as assessed by one or more physicians in an appropriately powered population of patients or by an appropriately powered clinical study (aspect 240).

In aspects, the invention is the pharmaceutical formulation of any one or more of aspects 150-240, wherein the formulations demonstrate at least 5% less surface toxicity as compared to TOBREX® as assessed by one or more physicians in an appropriately powered population of patients or by an appropriately powered clinical study (aspect 241).

In aspects, the invention is the pharmaceutical formulation of any one or more of aspects 150-241, wherein the formulations demonstrate that on average fewer than 2 people in 100 treated with the formulation experience a hypersensitivity or localized ocular toxicity reaction such as lid itching and swelling, and conjunctival erythema as assessed by one or more physicians in an appropriately powered population of patients or by an appropriately powered clinical study (aspect 242).

In aspects, the invention is the pharmaceutical formulation of any or more of aspects 150-242, wherein the formulation further comprises one or more additional actives (aspect 243).

In aspects, the invention is the pharmaceutical formulation of aspect 243, wherein the active is an anti-inflammatory (aspect 244).

In aspects, the invention is the pharmaceutical formulation of aspect 243, wherein the active is a steroid (aspect 245).

In aspects, the invention is the pharmaceutical formulation of aspect 245, wherein the active is dexamethasone (aspect 246).

In aspects, the invention is a method of reducing the level of bacterial infection present in an eye comprising application of a formulation according to any one or more of aspects 150-246 (aspect 247).

In aspects, the invention is a method of using a formulation according to any one or more of aspects 150-247 to treat a patient suffering from an ocular disease or condition which may be sensitive to such a formulation (aspect 248).

In aspects, the invention is the method of aspect 248, wherein the disease or condition is an external infection of the eye (aspect 249).

In aspects, the invention is the method of aspect 249, wherein the external infection is caused by a pathogen selected from a group comprising a gram-positive or a gram-negative ophthalmic pathogen (aspect 250).

In aspects, the invention is the method of aspect 250, wherein the pathogen is a Staphylococci, such as *S. Aureus* and *S. epidermis* (aspect 251).

In aspects, the invention is the method of any one or more of aspects 250-251, wherein the pathogen is a penicillin-resistant strain (aspect 252).

In aspects, the invention is the method of any one or more of aspects 247-252, wherein the concentration of the compound is between about 0.1-about 10% w/v (aspect 253).

In aspects, the invention is the method of aspect 253, wherein the concentration of the compound is between about 0.3-5% w/v (aspect 254).

In aspects, the invention is the method of aspect 254, wherein the concentration of the compound is between about 0.6-5% w/v (aspect 255).

In aspects, the invention is the method of aspect 255, wherein the concentration of the compound is between about 1-3% w/v (aspect 256).

In aspects, the invention is the method of aspect 256, wherein the concentration of the compound is approximately 2.5% w/v (aspect 257).

In aspects, the invention is the method of any one or more of aspects 253-257, wherein the concentration of the complexing agent, when present in the formulation, is present in a concentration of between about 0.1-10% w/v (aspect 258).

In aspects, the invention is the method of aspect 258, wherein the concentration of the complexing agent, when present in the formulation, is present in a concentration of between about 0.3-5% w/v (aspect 259).

In aspects, the invention is the method of aspect 259, wherein the concentration of the complexing agent, when present in the formulation, is present in a concentration of between about 0.6-5% w/v (aspect 260).

In aspects, the invention is the method of aspect 260, wherein the concentration of the complexing agent, when present in the formulation, is present in a concentration of between about 1-3% w/v (aspect 261).

In aspects, the invention is the method of aspect 261, wherein the concentration of the complexing agent, when present in the formulation, is present in a concentration of approximately 2.5% w/v (aspect 262).

In aspects, the invention is the method of any one or more of aspects 247-262, wherein the formulation is administered four times per day or less (aspect 263).

In aspects, the invention is the method of aspect 263, wherein the formulation is administered three times per day or less (aspect 264).

In aspects, the invention is the method of aspect 264, wherein the formulation is administered twice per day or less (aspect 265).

In aspects, the invention is the method of aspect 265, wherein the formulation is administered once daily (aspect 266).

The invention claimed is:

1. A pharmaceutical formulation comprising:
   (1) an ophthalmologically suitable complex, the complex comprising
      (a) tobramycin or a derivative thereof; and
      (b) histidine, which forms a complex with the tobramycin or a derivative thereof,
   (2) a pharmaceutically effective amount of dexamethasone or a pharmaceutically acceptable derivative thereof,
   wherein the histidine detectably promotes the uptake of the tobramycin or derivative thereof by corneal cells, the retention of the tobramycin or derivative thereof by corneal cells, or both, as compared to the free (non-complexed) tobramycin or derivative thereof.

2. The pharmaceutical composition of claim 1, wherein the dexamethasone or the pharmaceutically suitable derivative thereof is present in a concentration of about 0.02-about 0.15% w/v.

3. The pharmaceutical composition of claim 2, wherein the dexamethasone or the pharmaceutically suitable derivative thereof is dexamethasone.

4. The pharmaceutical composition of claim 3, wherein the complex is present in an amount of about 0.3-about 5% w/v.

5. The pharmaceutical composition of claim 1, wherein the complex is present in an amount of about 0.3-about 5% w/v.

6. The pharmaceutical composition of claim 1, wherein the concentration of compound permeating the surface of the cornea is at least about 15% greater after 15 minutes from application than a corresponding amount of tobramycin in a composition consisting of tobramycin at 0.3% w/v, benzalkonium chloride at 0.01% w/v, boric acid at 1.24% w/v, sodium sulfate at 0.152% w/v, sodium chloride at 0.278% w/v, tyloxapol at 0.1% w/v, sodium hydroxide and/or sulfuric acid, and purified water.

7. The pharmaceutical composition of claim 2, wherein an effective amount of the composition prevents detectable or significant growth of a bacterial infective agent for a period of at least 6 hours after administration.

8. The pharmaceutical composition of claim 1, wherein an effective amount of the composition prevents detectable or significant growth of a bacterial infective agent for a period of at least 6 hours after administration.

9. The pharmaceutical composition of claim 4, wherein an effective amount of the composition prevents detectable or significant growth of a bacterial infective agent for a period of at least 6 hours after administration.

10. The pharmaceutical composition of claim 1, wherein the histidine and the tobramycin or derivative thereof are present in a weight/weight ratio of about 0.5:1 to about 2:1.

* * * * *

UNITED STATES PATENT AND TRADEMARK OFFICE
CERTIFICATE OF CORRECTION

| | |
|---|---|
| PATENT NO. | : 11,395,831 B2 |
| APPLICATION NO. | : 17/327703 |
| DATED | : July 26, 2022 |
| INVENTOR(S) | : Shah et al. |

It is certified that error appears in the above-identified patent and that said Letters Patent is hereby corrected as shown below:

On the Title Page

Item (54) and in the Specification, Column 1, Lines 1-3, Should read:
COMBINATION PRODUCTS OF TOBRAMYCIN COMPOUNDS AND DEXAMETHASONE COMPOUNDS Signed and Sealed this
Thirty-first Day of October, 2023

Katherine Kelly Vidal
*Director of the United States Patent and Trademark Office*